(12) United States Patent
Nguyen et al.

(10) Patent No.: US 9,044,236 B2
(45) Date of Patent: Jun. 2, 2015

(54) CORING KNIFE

(75) Inventors: John Duc Nguyen, San Ramon, CA (US); Donald Curtis, Berkeley, CA (US); Carine Hoarau, Lafayette, CA (US)

(73) Assignee: Thoratec Corporation, Pleasanton, CA (US)

( * ) Notice: Subject to any disclaimer, the term of this patent is extended or adjusted under 35 U.S.C. 154(b) by 85 days.

(21) Appl. No.: 13/474,096

(22) Filed: May 17, 2012

(65) Prior Publication Data

US 2012/0296358 A1 Nov. 22, 2012

Related U.S. Application Data

(60) Provisional application No. 61/487,658, filed on May 18, 2011.

(51) Int. Cl.
*A61B 17/32* (2006.01)
*A61B 17/11* (2006.01)
(Continued)

(52) U.S. Cl.
CPC ........... *A61B 17/11* (2013.01); *A61B 17/32002* (2013.01); *A61B 17/32053* (2013.01); *A61B 17/3462* (2013.01); *A61B 2017/00252* (2013.01); *A61B 2017/1135* (2013.01); *A61B 2017/3425* (2013.01); *A61B 17/1204* (2013.01); *A61B 17/12109* (2013.01); *A61B 17/12136* (2013.01); *A61B 2017/00243* (2013.01); *A61B 2017/00526* (2013.01); *A61B 2017/1107* (2013.01); *A61B 2017/1125* (2013.01); *A61B 2017/12004* (2013.01); *A61M 1/1008* (2014.02)

(58) Field of Classification Search
CPC ................. A61B 17/32053; A61B 2017/1107; A61B 2017/00247; A61B 2017/00252
USPC ...................... 606/167–170, 184, 185; 83/683
See application file for complete search history.

(56) References Cited

U.S. PATENT DOCUMENTS 3,512,519 A * 5/1970 Hall ............................... 600/567
5,129,913 A * 7/1992 Ruppert ........................ 606/184
(Continued)

FOREIGN PATENT DOCUMENTS

EP 1 691 884 B1 3/2011
EP 1 628 702 B1 5/2013
(Continued)

OTHER PUBLICATIONS

International Search Report and Written Opinion for PCT/US2012/038354, mailed Dec. 26, 2012, 11 pgs.
(Continued)

*Primary Examiner* — Tuan V Nguyen
*Assistant Examiner* — Chima Igboko
(74) *Attorney, Agent, or Firm* — Squire Patton Boggs (US) LLP

(57) ABSTRACT

A coring knife can be used to make a circular incision. The coring knife includes an abutment that is inserted into an initial slit through the heart wall. The abutment can be inserted into the slit while oriented in a direction that minimizes its insertion profile. After insertion, the abutment is reoriented by turning a key so that its abutment surface faces toward a circular cutting edge of the coring knife on the other side of the heart wall. The circular incision through the heart wall is made by pressing the circular cutting edge of the coring knife against the abutment.

21 Claims, 45 Drawing Sheets

(51) Int. Cl.
*A61B 17/3205* (2006.01)
*A61B 17/34* (2006.01)
*A61M 1/10* (2006.01)
A61B 17/00 (2006.01)
A61B 17/12 (2006.01)

(56) References Cited

U.S. PATENT DOCUMENTS

| | | | |
|---|---|---|---|
| 5,158,563 A | 10/1992 | Cosman | |
| 5,291,179 A | 3/1994 | Ooe et al. | |
| 5,403,338 A * | 4/1995 | Milo | 606/184 |
| 5,531,756 A * | 7/1996 | Larose | 606/184 |
| 5,582,616 A | 12/1996 | Bolduc et al. | |
| 5,814,005 A | 9/1998 | Barra et al. | |
| 5,827,316 A * | 10/1998 | Young et al. | 606/185 |
| 5,893,369 A * | 4/1999 | LeMole | 606/184 |
| 5,906,630 A * | 5/1999 | Anderhub et al. | 606/205 |
| 5,910,153 A * | 6/1999 | Mayenberger | 606/184 |
| 6,022,324 A * | 2/2000 | Skinner | 600/566 |
| 6,033,419 A * | 3/2000 | Hamblin et al. | 606/184 |
| 6,036,710 A * | 3/2000 | McGarry et al. | 606/184 |
| 6,039,748 A * | 3/2000 | Savage et al. | 606/180 |
| 6,079,414 A | 6/2000 | Roth | |
| 6,080,173 A * | 6/2000 | Williamson et al. | 606/184 |
| 6,080,176 A * | 6/2000 | Young | 606/185 |
| 6,267,732 B1 * | 7/2001 | Heneveld et al. | 600/564 |
| 6,346,071 B1 | 2/2002 | Mussivand | |
| 6,537,300 B2 | 3/2003 | Girton | |
| 6,551,332 B1 | 4/2003 | Nguyen et al. | |
| 6,607,541 B1 | 8/2003 | Gardiner et al. | |
| 6,669,708 B1 | 12/2003 | Nissenbaum et al. | |
| 6,676,678 B2 * | 1/2004 | Gifford et al. | 606/184 |
| 6,689,147 B1 * | 2/2004 | Koster, Jr. | 606/184 |
| 6,695,859 B1 | 2/2004 | Golden et al. | |
| 6,699,256 B1 | 3/2004 | Logan et al. | |
| 6,726,648 B2 | 4/2004 | Kaplon et al. | |
| 6,732,501 B2 | 5/2004 | Yu et al. | |
| 6,776,787 B2 * | 8/2004 | Phung et al. | 606/185 |
| 6,802,806 B2 | 10/2004 | McCarthy et al. | |
| 6,824,071 B1 | 11/2004 | McMichael | |
| 6,863,677 B2 | 3/2005 | Breznock | |
| 6,942,672 B2 | 9/2005 | Heilman et al. | |
| 7,077,801 B2 | 7/2006 | Haverich | |
| 7,258,694 B1 * | 8/2007 | Choi et al. | 606/184 |
| 7,309,343 B2 | 12/2007 | Vargas et al. | |
| 7,510,561 B2 | 3/2009 | Beane et al. | |
| 7,717,844 B2 | 5/2010 | Cohn | |
| 7,744,527 B2 | 6/2010 | Cohn | |
| 7,846,123 B2 | 12/2010 | Vassiliades et al. | |
| 7,931,581 B2 | 4/2011 | Cohn | |
| 7,942,805 B2 | 5/2011 | Shambaugh, Jr. | |
| 7,993,392 B2 | 8/2011 | Righini et al. | |
| 8,226,670 B2 * | 7/2012 | Beane et al. | 606/153 |
| 8,556,930 B2 | 10/2013 | Ellingwood | |
| 2002/0038127 A1 * | 3/2002 | Blatter et al. | 606/153 |
| 2002/0045846 A1 | 4/2002 | Kaplon et al. | |
| 2002/0058958 A1 * | 5/2002 | Walen | 606/170 |
| 2002/0177865 A1 * | 11/2002 | McIntosh | 606/184 |
| 2003/0040765 A1 | 2/2003 | Breznock | 606/184 |
| 2003/0045834 A1 * | 3/2003 | Wing et al. | 604/161 |
| 2003/0130668 A1 * | 7/2003 | Nieman et al. | 606/108 |
| 2004/0049223 A1 * | 3/2004 | Nishtala et al. | 606/198 |
| 2004/0082963 A1 * | 4/2004 | Gannoe et al. | 606/153 |
| 2004/0092974 A1 * | 5/2004 | Gannoe et al. | 606/153 |
| 2004/0098011 A1 * | 5/2004 | Vargas et al. | 606/184 |
| 2005/0101983 A1 * | 5/2005 | Loshakove et al. | 606/185 |
| 2005/0154411 A1 * | 7/2005 | Breznock et al. | 606/184 |
| 2006/0036313 A1 | 2/2006 | Vassiliades et al. | |
| 2006/0041243 A1 * | 2/2006 | Nayak et al. | 604/506 |
| 2006/0074484 A1 | 4/2006 | Huber | |
| 2006/0089707 A1 | 4/2006 | Vassiliades et al. | |
| 2006/0167333 A1 | 7/2006 | Moore et al. | |
| 2007/0055357 A1 | 3/2007 | Pokorney et al. | |
| 2007/0066943 A1 | 3/2007 | Prasad et al. | |
| 2007/0167968 A1 * | 7/2007 | Pandey | 606/185 |
| 2007/0167969 A1 | 7/2007 | Pandey | |
| 2007/0197856 A1 | 8/2007 | Gellman et al. | |
| 2007/0265643 A1 | 11/2007 | Beane et al. | |
| 2008/0039883 A1 * | 2/2008 | Nohilly | 606/180 |
| 2008/0058846 A1 * | 3/2008 | Vosough | 606/180 |
| 2008/0255597 A1 * | 10/2008 | Pravong et al. | 606/169 |
| 2009/0082778 A1 | 3/2009 | Beane et al. | |
| 2009/0112062 A1 | 4/2009 | Bakos | |
| 2009/0171136 A1 | 7/2009 | Shambaugh, Jr. | |
| 2009/0204206 A1 | 8/2009 | Parquet et al. | |
| 2010/0010500 A1 | 1/2010 | Beane et al. | |
| 2010/0161040 A1 | 6/2010 | Braido et al. | |
| 2010/0168778 A1 | 7/2010 | Braido | |
| 2011/0144680 A1 | 6/2011 | Nguyen et al. | |
| 2012/0089181 A1 | 4/2012 | Shanley et al. | |

FOREIGN PATENT DOCUMENTS

| | | |
|---|---|---|
| WO | WO 03/001980 | 1/2003 |
| WO | WO 2006/019755 | 2/2006 |
| WO | WO 2007/038109 | 4/2007 |
| WO | WO 2008/153872 A2 | 12/2008 |
| WO | WO 2009/100198 | 8/2009 |
| WO | WO 2013/064529 A1 | 5/2013 |

OTHER PUBLICATIONS

International Search Report for PCT/US2010/056751, mailed Oct. 7, 2011, 22 pgs.

\* cited by examiner

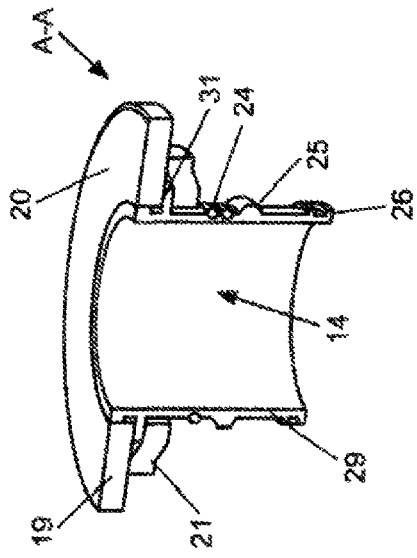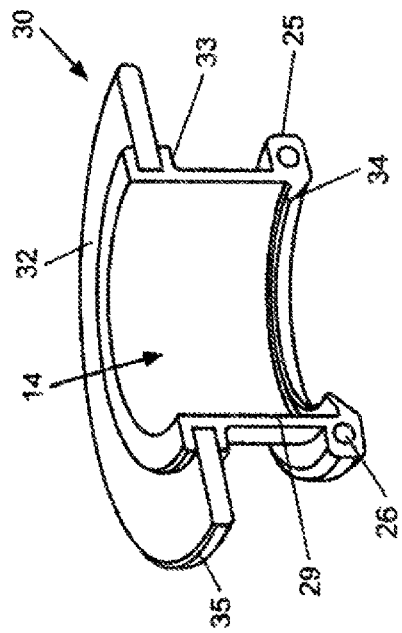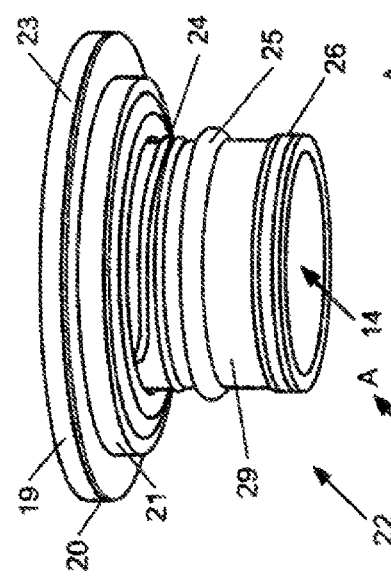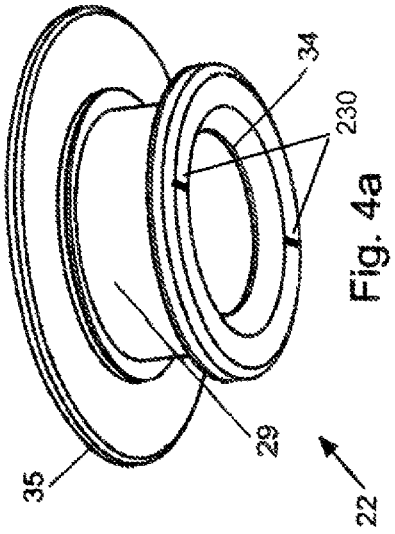

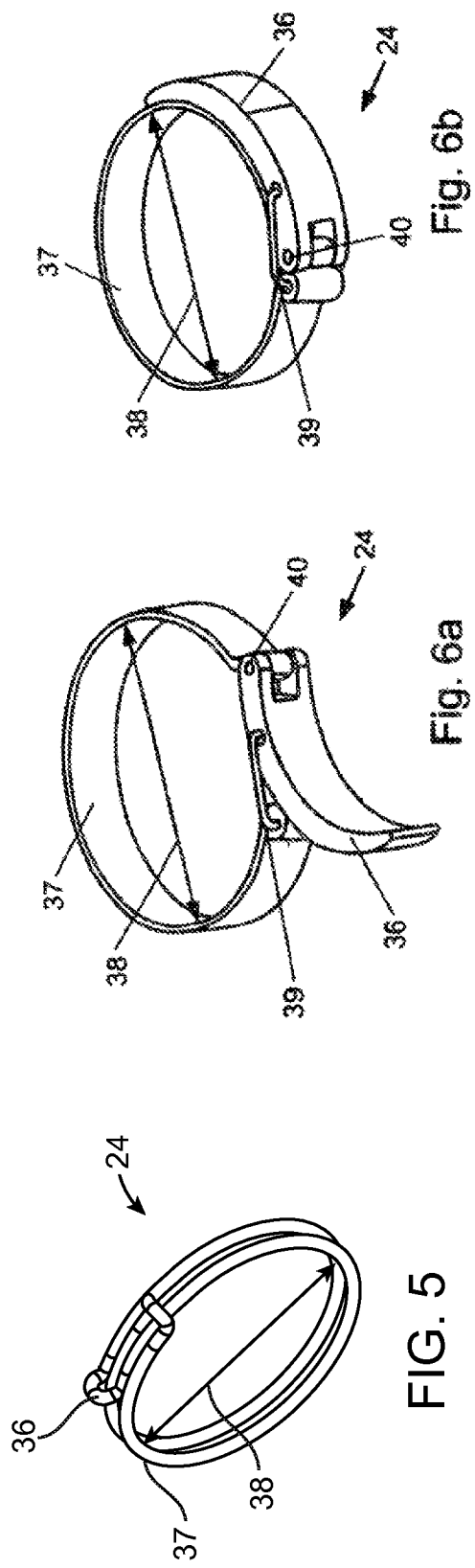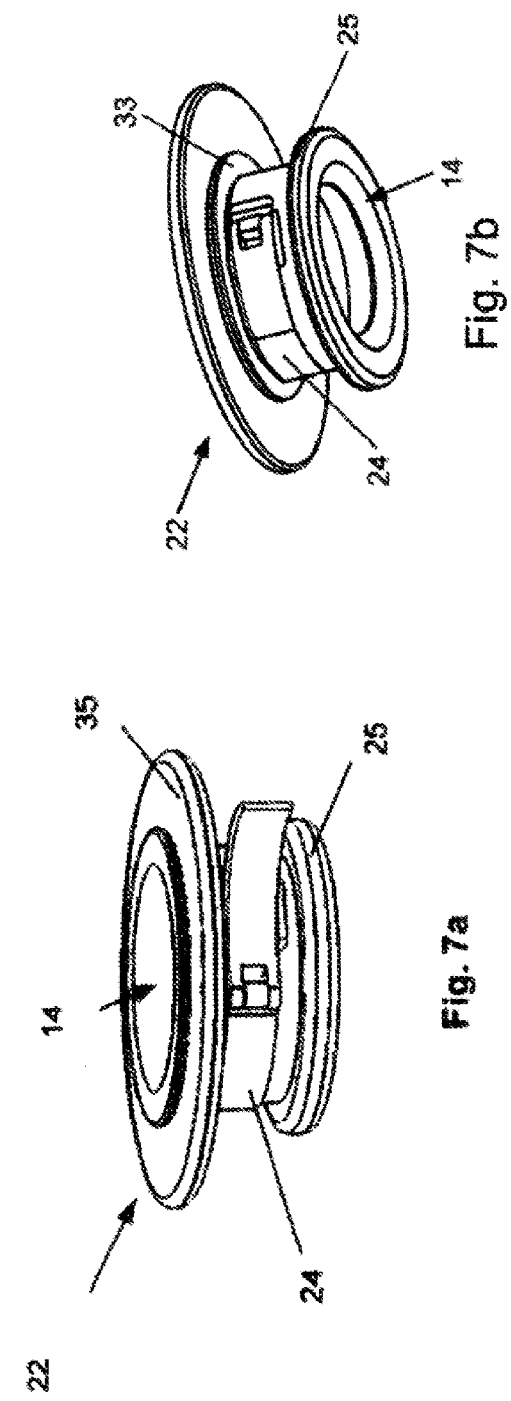

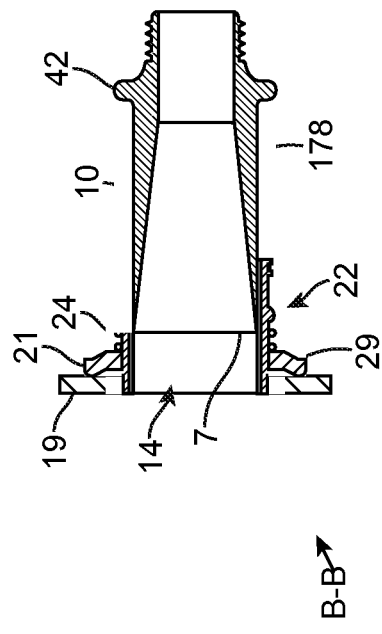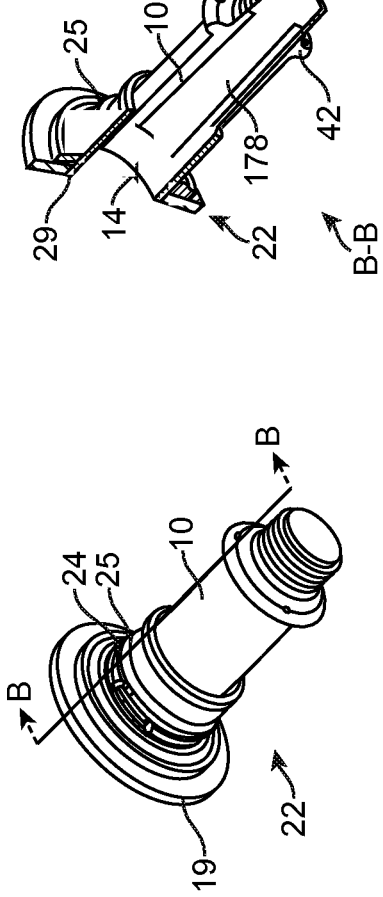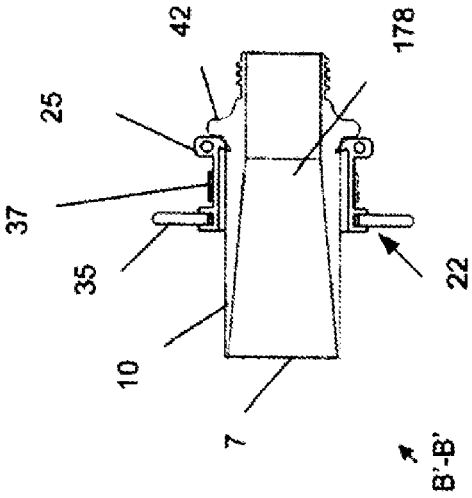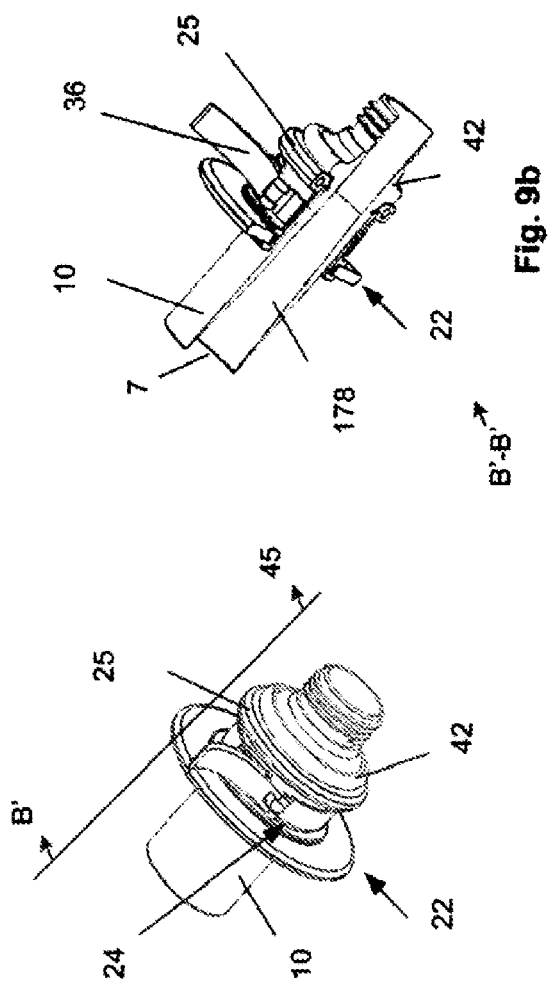

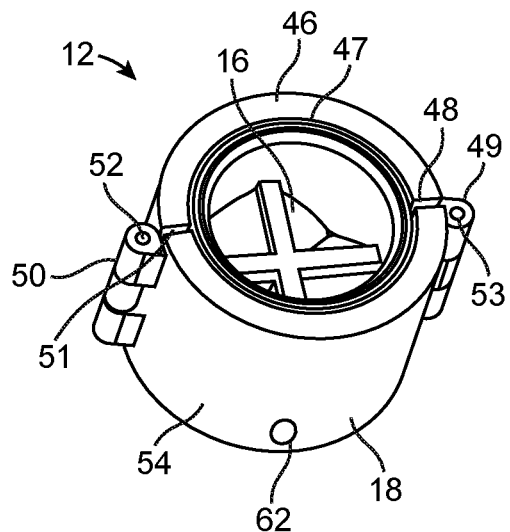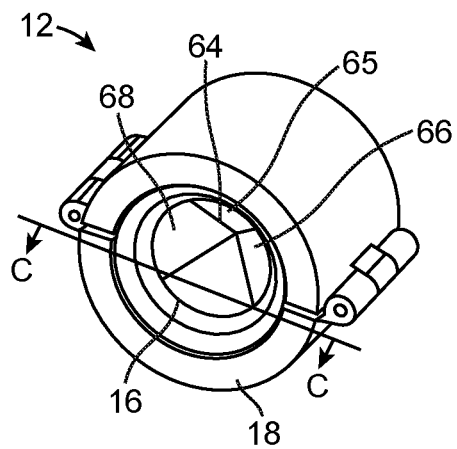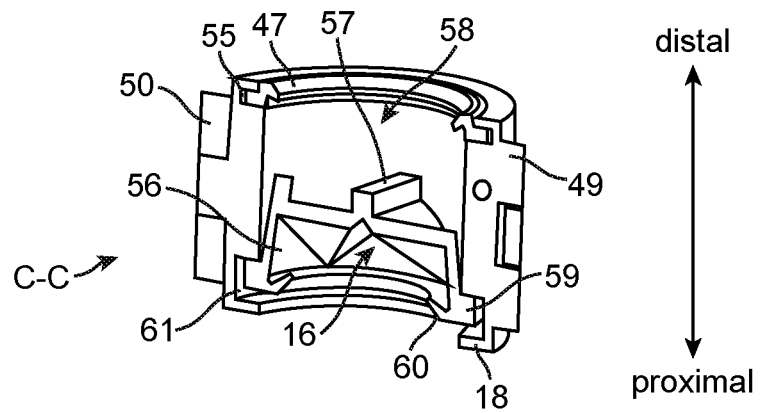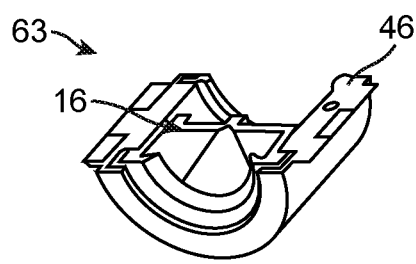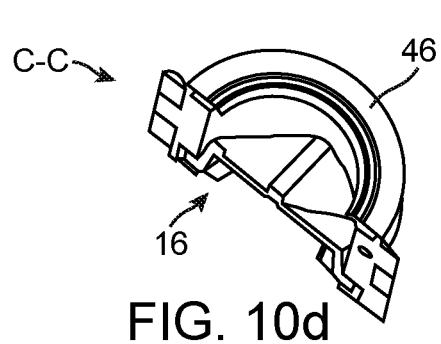
FIG. 10a
FIG. 10b
FIG. 10c
FIG. 10e
FIG. 10d

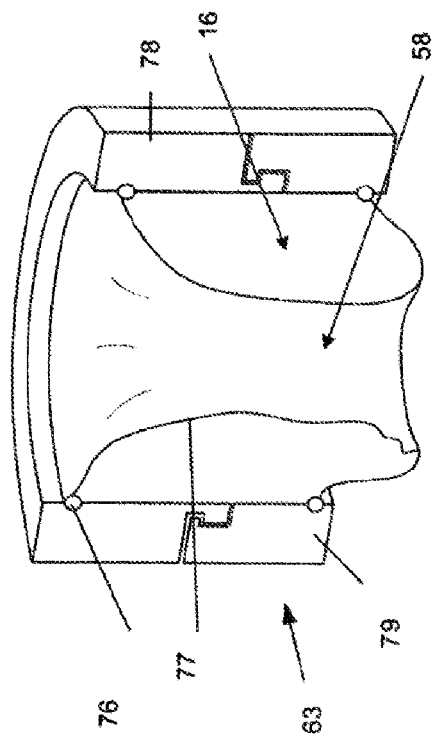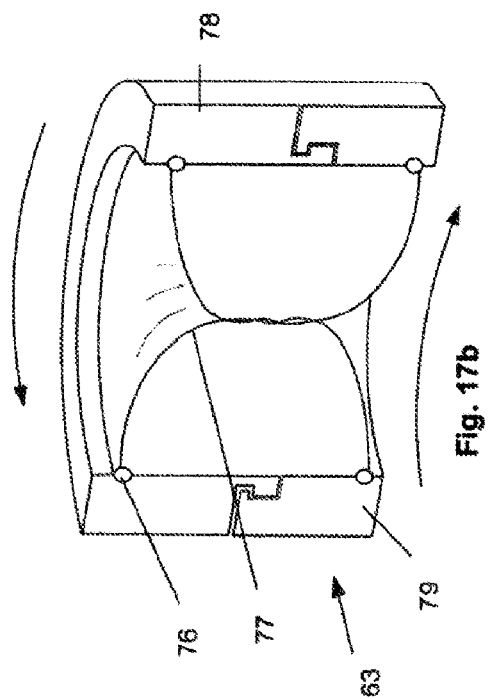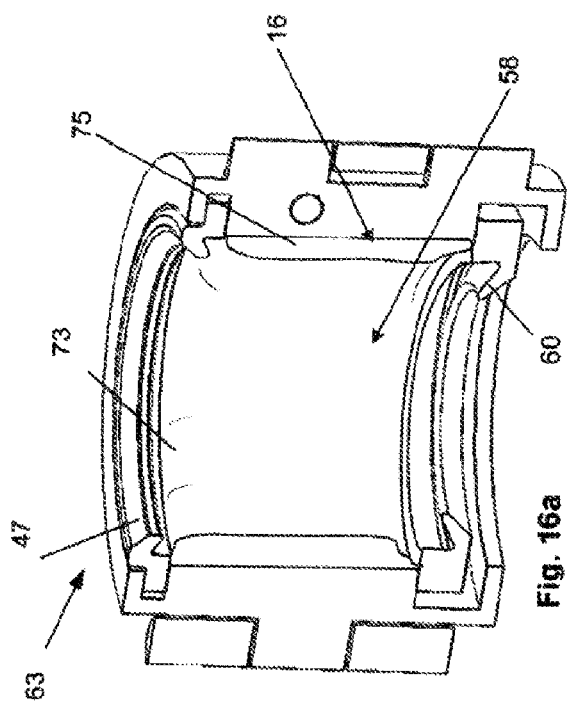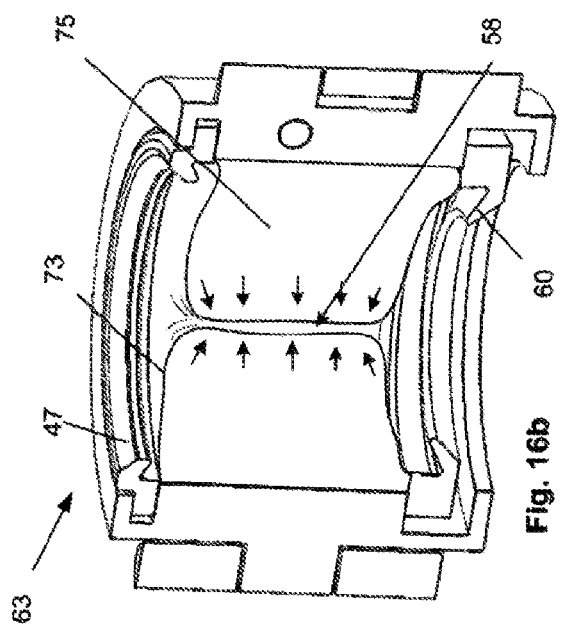

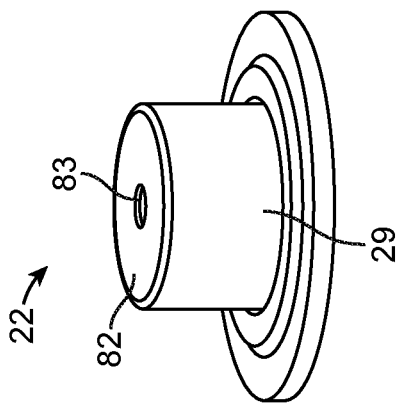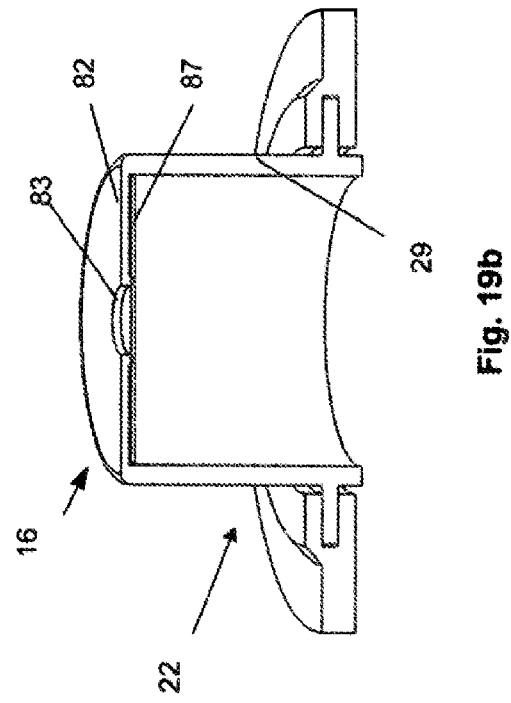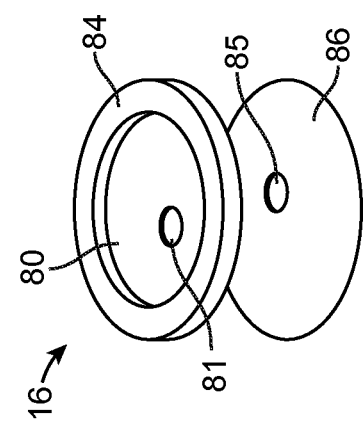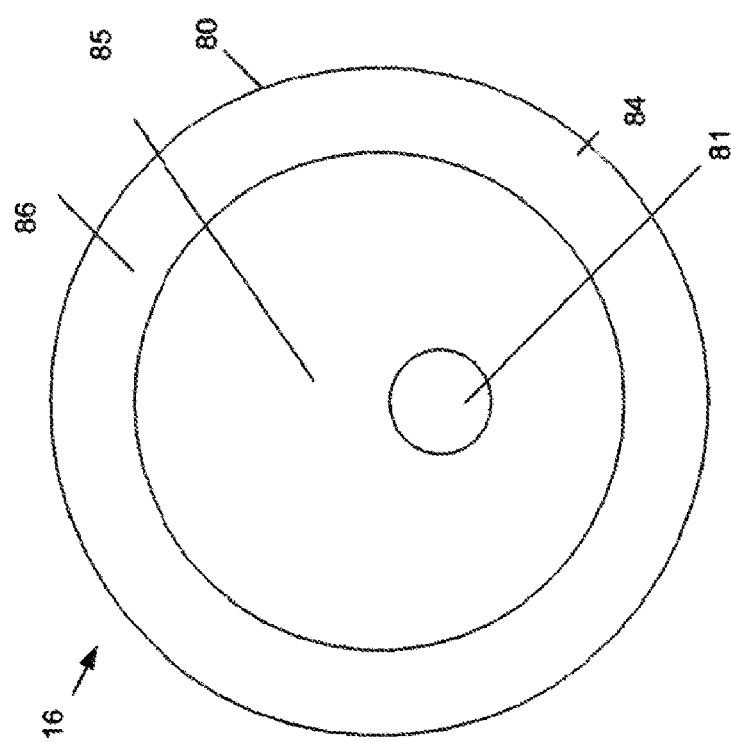

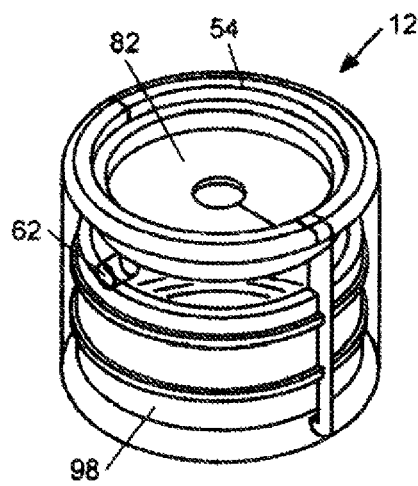
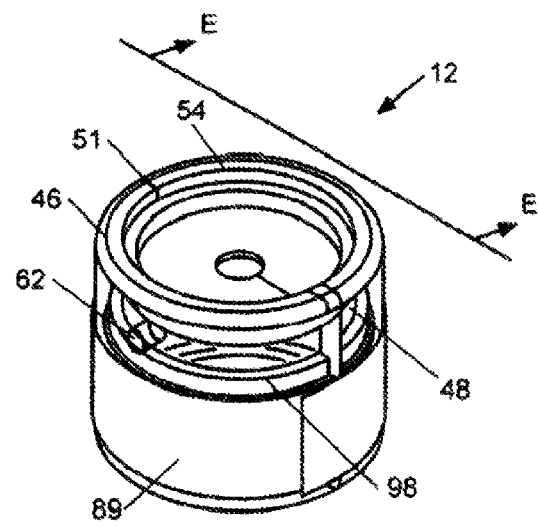
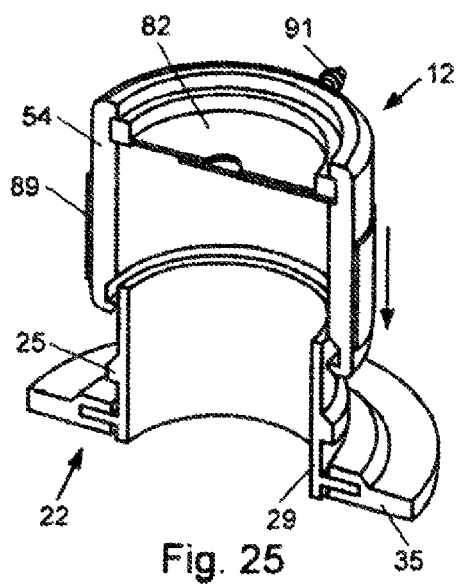
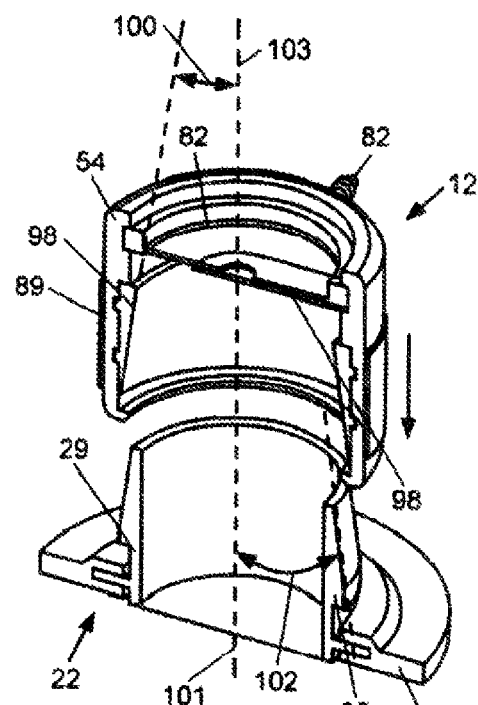

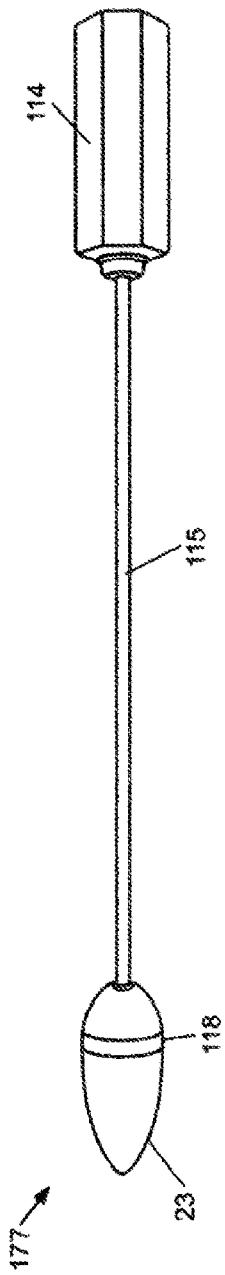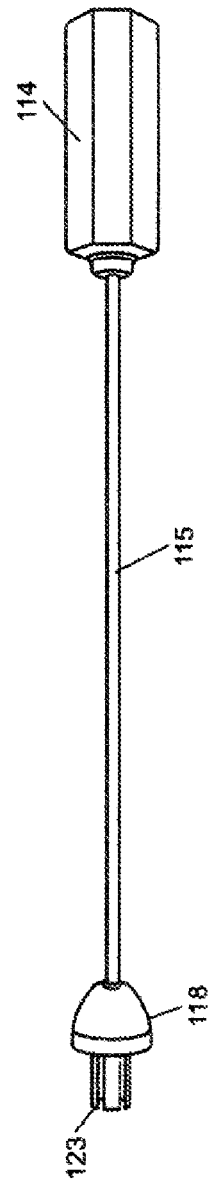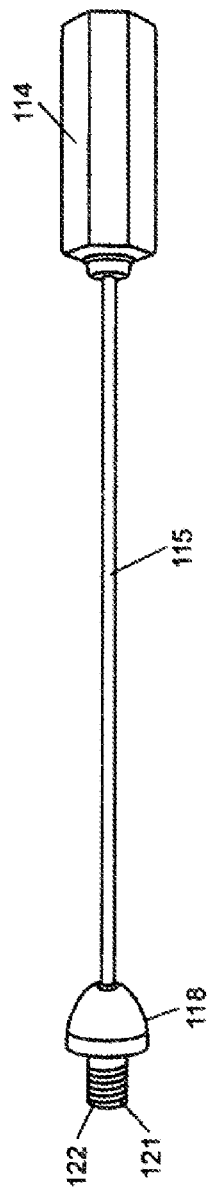

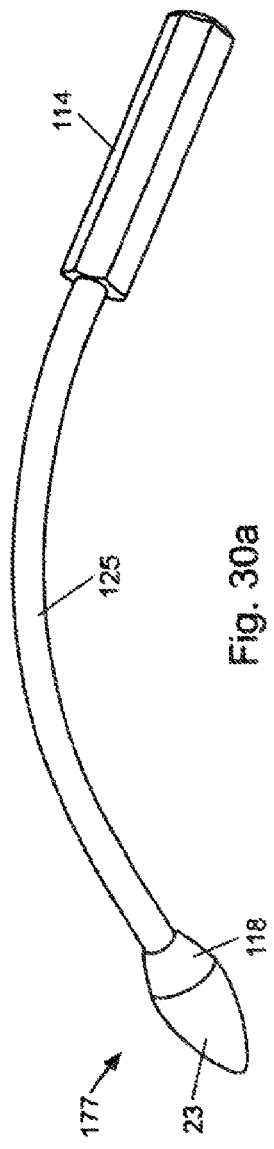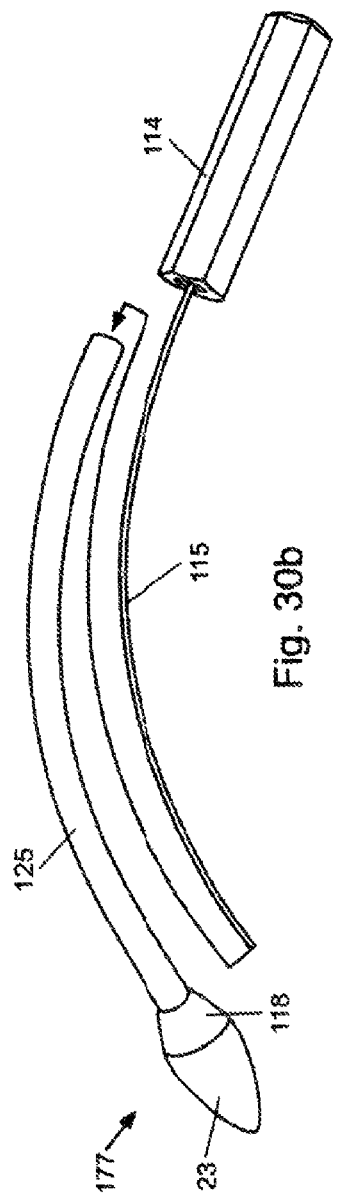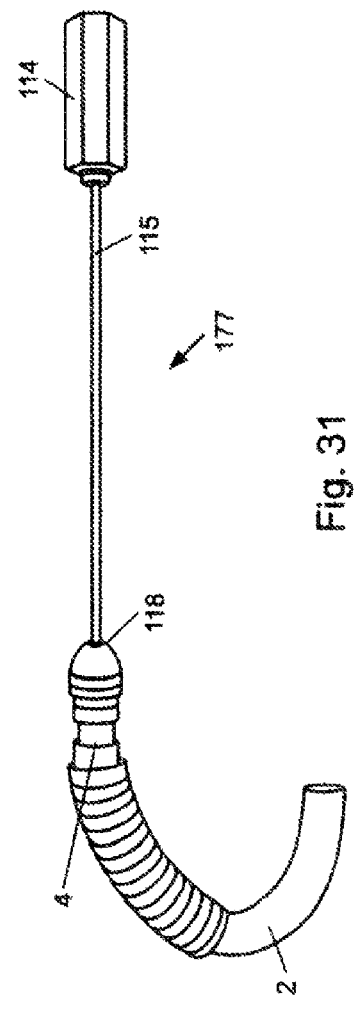

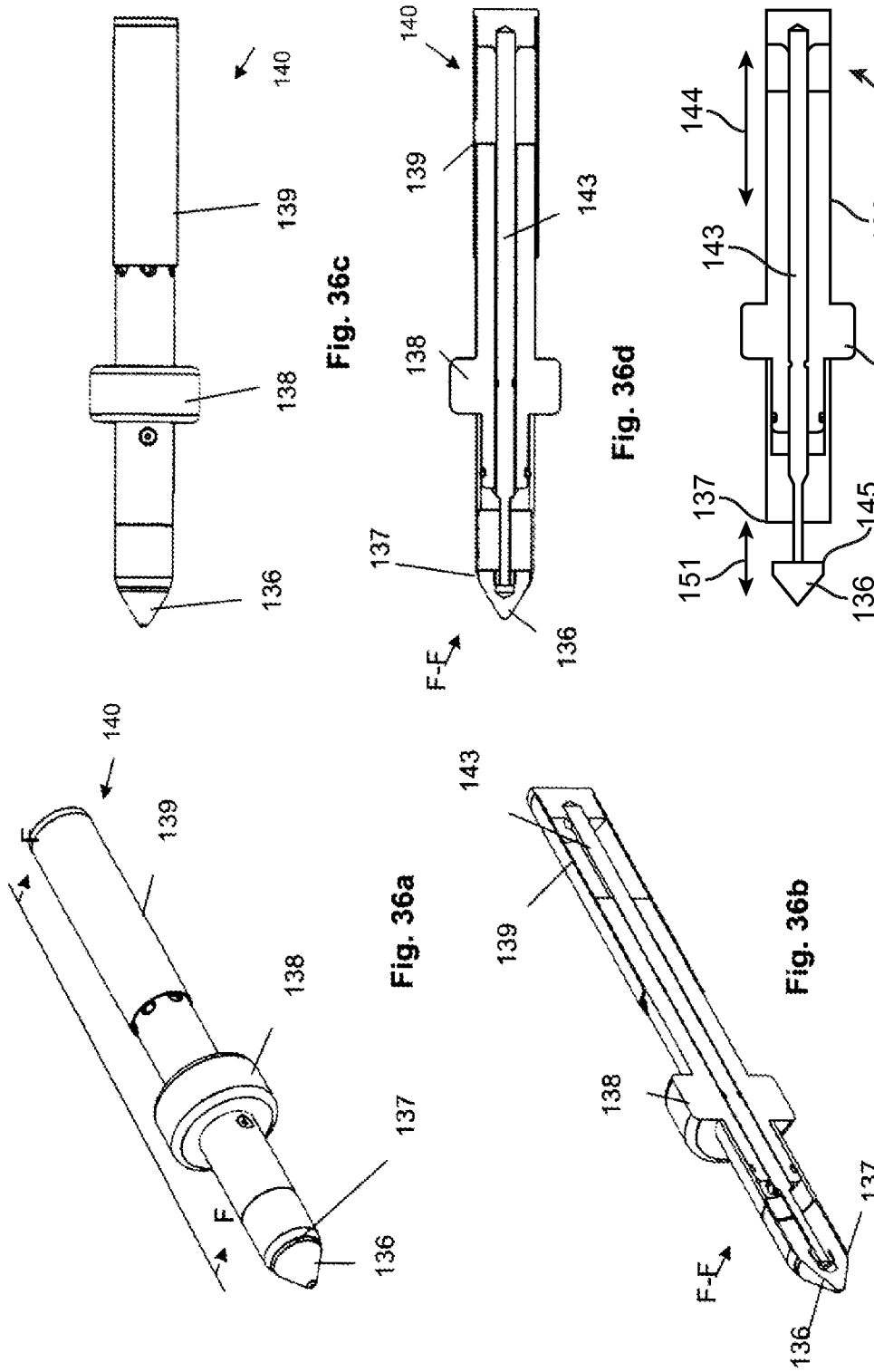

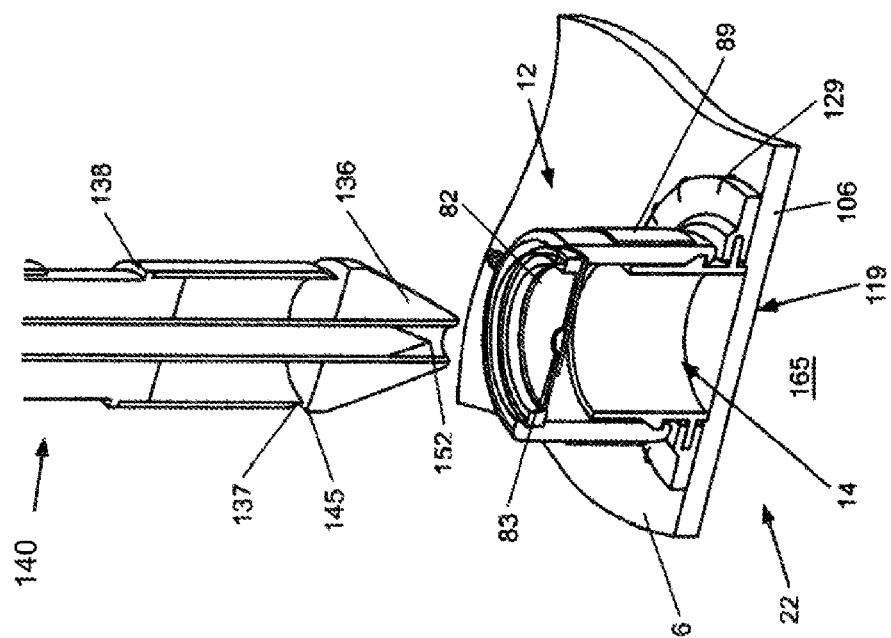
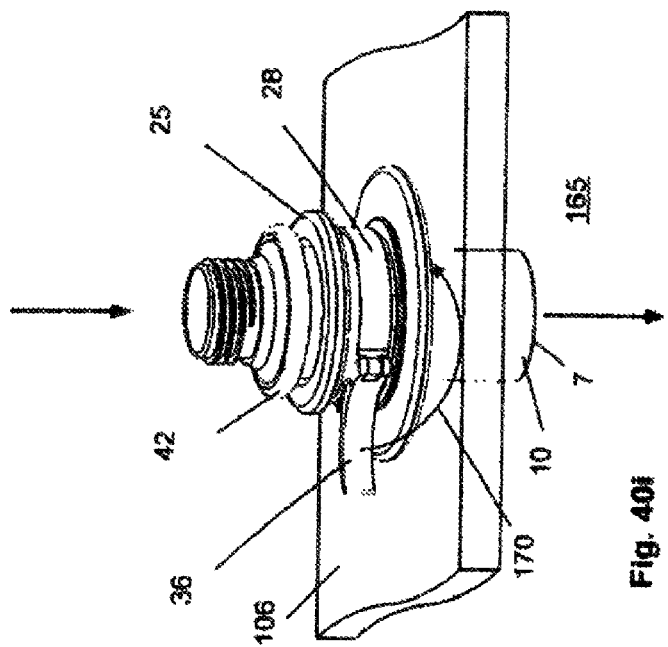

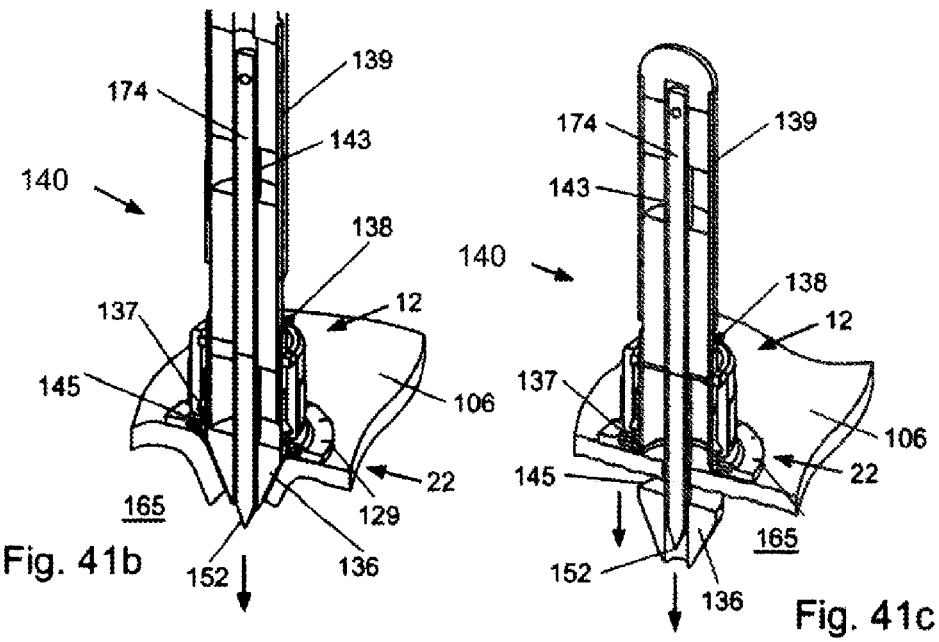
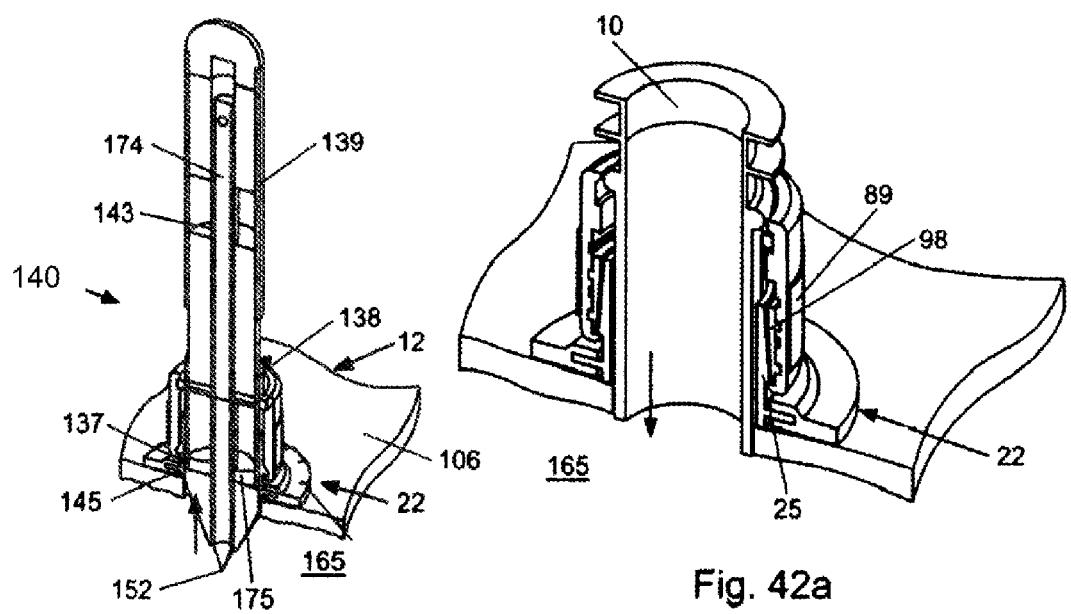
Fig. 41b  Fig. 41c
Fig. 41d  Fig. 42a

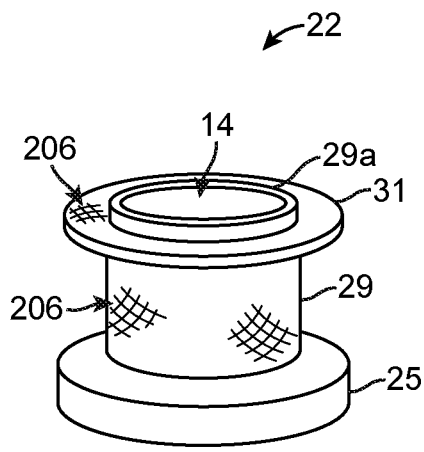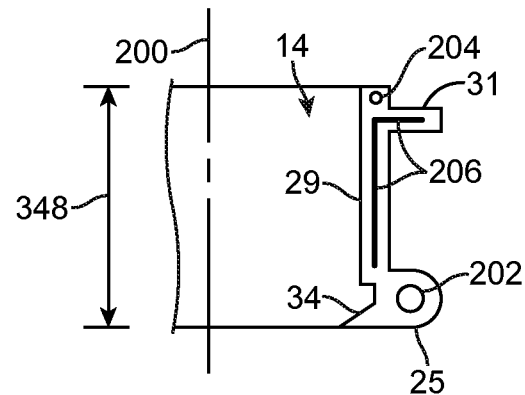
FIG. 46a    FIG. 46b
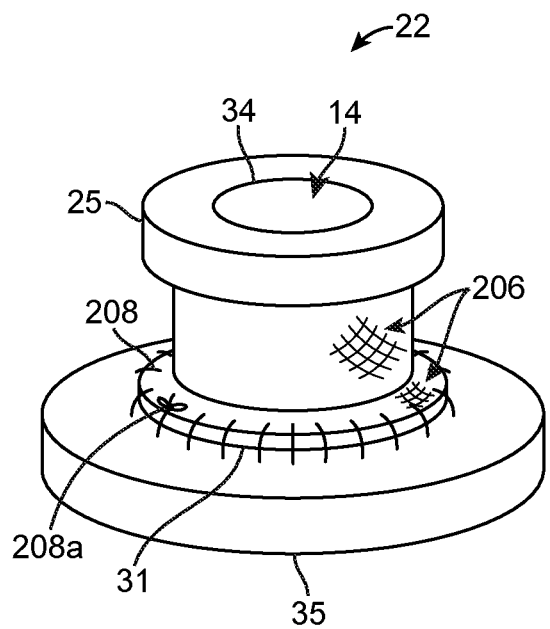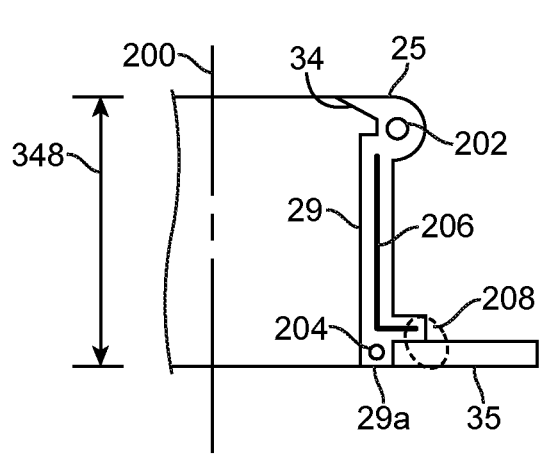
FIG. 46c    FIG. 46d

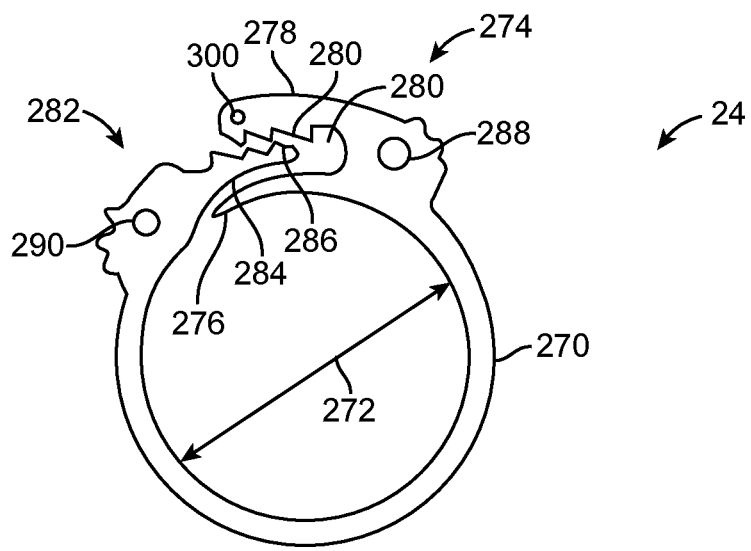
FIG. 50a
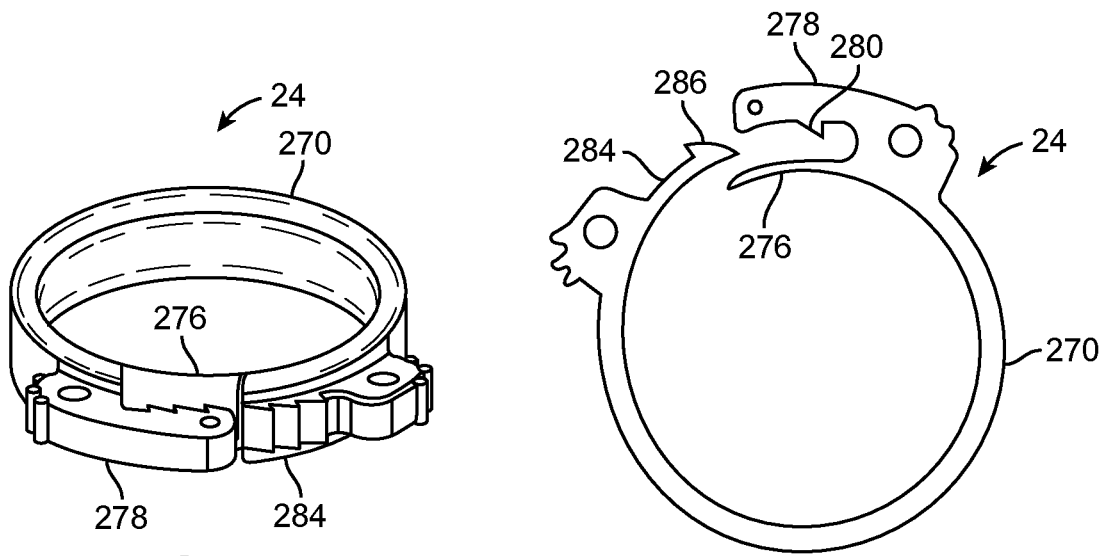
FIG. 50b
FIG. 51

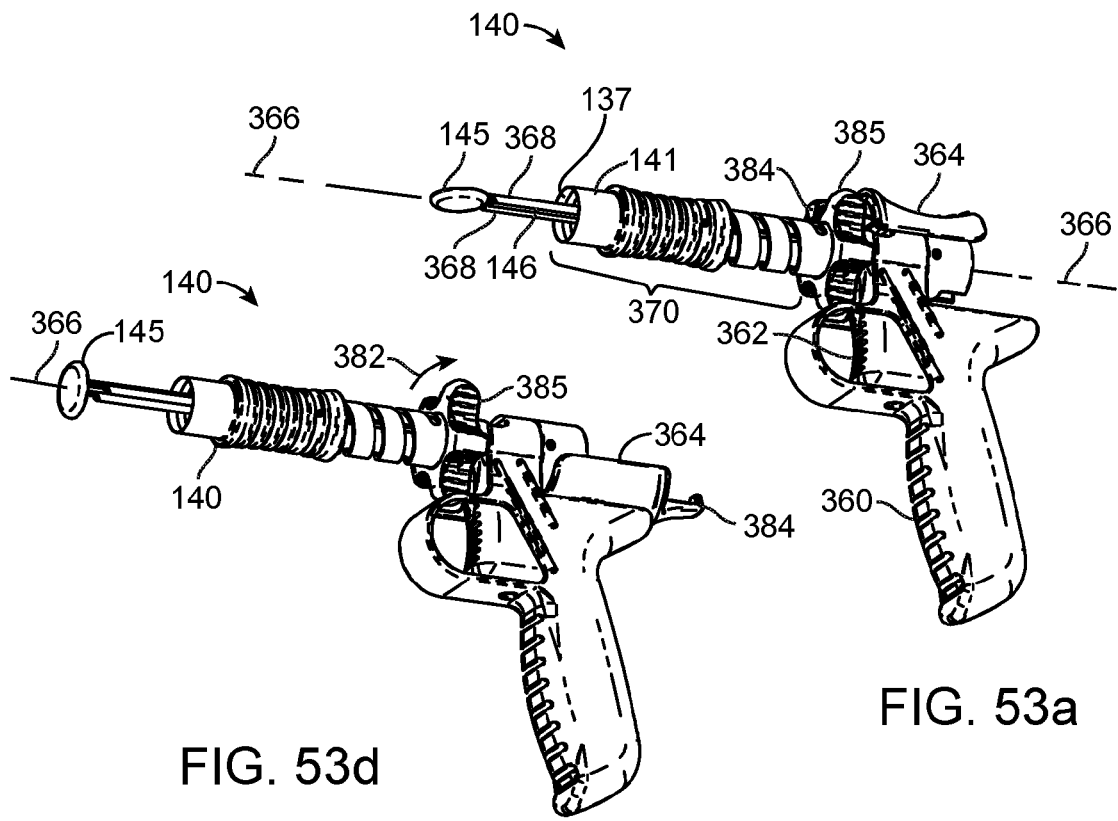
FIG. 53a
FIG. 53d
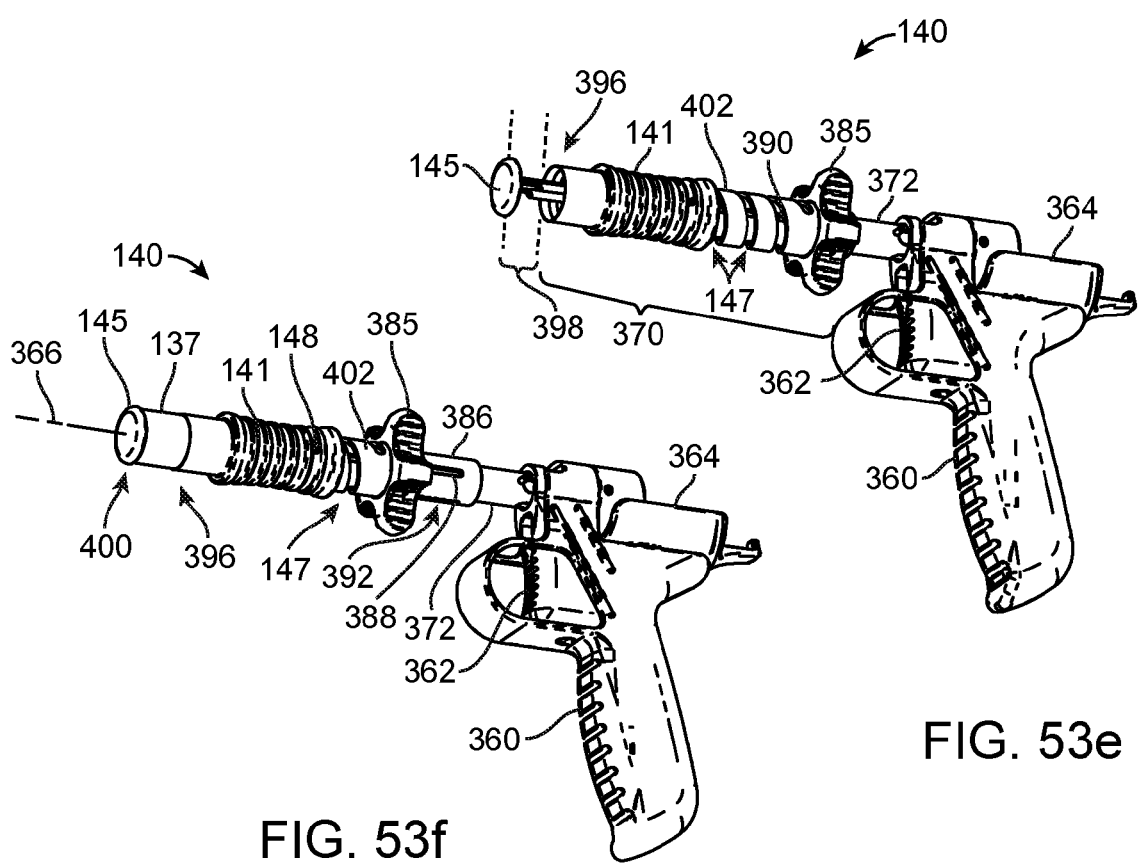
FIG. 53e
FIG. 53f

CORING KNIFE

CROSS-REFERENCE TO RELATED APPLICATION

This application claims the benefit of U.S. Provisional Application No. 61/487,658 filed May 18, 2011, which is incorporated herein by reference.

BACKGROUND OF THE INVENTION

1. Field of the Invention

This invention relates to the field of heart assist devices and methods, devices and systems for the in vivo implantation of VADs and its attachment to the heart.

2. Description of the Related Art

Heart assist devices are implantable devices that assist the heart in circulating blood in the body. A ventricular assist device (VAD) is an example of a heart assist device that is used to assist one or both ventricles of the heart to circulate blood. For patients suffering from heart failure, assisting the left ventricle with a VAD is more common. Currently, VADs are commonly used as a treatment option or a bridge to transplant for patients with heart failure.

The procedure to implant VADs carries many risks and side effects. The implantation procedure is invasive as surgeons need to access the heart directly by opening the chest with a sternotomy or a thoracotomy. Generally, a heart-lung bypass machine is used during the procedure, but a beating heart procedure may minimize side effects associated with using a heart-lung bypass machine in such a major invasive surgery. However, a beating heart procedure can potentially lead to significant blood loss during the process of implanting the VAD if great care is not exercised.

While procedural related issues during the implantation process can directly impact the success of the implantation, some of these procedural issues may also impact patients' recovery. When complications arise during the implantation process, the recovery time for these very ill patients can be extended. Procedural issues may result in major detrimental side effects for patients, directly increasing the recovery time. The recovery time and risk factors are often compounded by the originally poor health of the heart failure patient in need of the VAD.

A system and method for implanting a ventricular assist device without a sternotomy is desired. Furthermore, a system and method for safely implanting a VAD without requiring heart-lung bypass is desired. Additionally, a system and method for implanting a ventricular assist device in a beating-heart procedure is desired.

SUMMARY OF THE INVENTION

Briefly and in general terms, the present invention is directed to a coring knife.

In aspects of the present invention, a coring knife comprises a coring blade, a coring abutment, a key socket, and a key. The coring blade includes a circular cutting edge. The coring abutment is located forward of the cutting edge. The key socket is located to the rear of the coring blade and includes a bearing surface. The key is connected to the coring abutment, includes a key edge in contact with the bearing surface, and is configured to be moved relative the key socket. When key is moved relative the key socket, the key edge slips against the bearing surface and the key pivots the coring abutment relative to the coring blade.

In other aspects, the coring knife further comprises a control arm connecting the coring abutment to the key. The control arm extends through the coring blade and the key socket.

In other aspects, the key is configured to be twisted about a twist axis. When the key is twisted, the key edge slips against the bearing surface and the key pivots the coring abutment relative to the coring blade In other aspects, when the key is twisted, the control arm moves along a longitudinal axis that is parallel to the twist axis.

In other aspects, the key includes a cylinder having an outer surface that terminates at the key edge.

In other aspects, the key edge is disposed within a rear cavity of the key socket.

In other aspects, the key socket includes a forward cavity and a septum wall separating the forward cavity from the rear cavity, and the bearing surface forms a side of the of the wall within the rear cavity.

In other aspects, the coring blade is mounted over a central shaft extending out of the forward cavity of the key socket, the coring blade is configured to be rotated around the central shaft, and when the coring blade is rotated, the coring blade moves toward the coring abutment.

In other aspects, the coring blade is carried on an internal sleeve. The internal sleeve is carried on a central shaft extending out of the forward cavity of the key socket. The internal sleeve is configured to slide relative the central shaft in a direction toward the coring abutment. The coring blade is configured to be rotate relative the internal sleeve. When the coring blade is rotated, the coring blade moves toward the coring abutment.

In other aspects, the coring knife further comprises a coring knife case configured to be moved away from the key socket. The coring blade is movable into and out of the coring knife case.

In other aspects, the coring blade is configured to move out of the coring knife case by rotating the coring blade relative to the coring knife case.

In other aspects, the coring knife further comprises an control sleeve attached to the coring blade, the control sleeve having a helical slot that extends into the coring knife case. The coring knife case includes a guide peg that protrudes into the helical slot, and wherein rotation of the control sleeve causes the coring blade to move out of the coring knife case.

In other aspects, the coring knife further comprises an internal sleeve and a central shaft. The central shaft fixedly attached to the key socket and extends into the internal sleeve. The internal sleeve carries the control sleeve, the coring blade, and the coring knife case. The internal sleeve is configured to be selectively positioned and locked at any one of a plurality of locations on the central shaft.

In aspects of the present invention, a coring knife comprises a coring blade, a coring abutment, and coring knife case, and a key. The coring blade includes a cylindrical wall defining a circular cutting edge and a hollow interior. The coring knife case contains the coring blade. The coring blade is configured to be extended out of the coring knife case and toward the coring abutment. The key is coupled to the coring abutment by a control arm extending into the coring blade. The key disposed within a key socket and configured to be rotated relative to the key socket. When key is rotated relative the key socket, the key pulls the control arm in a manner that pivots the coring abutment relative to the coring blade.

In other aspects, the coring knife case includes a stop feature configured to fit in an alignment feature of a separate device for aligning the coring knife prior to extension of the coring blade out of the coring knife case.

In other aspects, the coring knife case is configured to be selectively positioned and locked at any one of a plurality of locations between the key socket and the coring abutment prior to extension of the coring blade out of the coring knife case.

In other aspects, the coring knife further comprising a detent mechanism that selectively locks and unlocks the coring knife case at any one of the plurality of locations between the key socket and the coring abutment.

In aspects of the present invention, a coring knife comprises a coring abutment, a key connected to the coring abutment, and a slide assembly disposed between the key and the coring abutment. The slide assembly includes a coring blade with a circular cutting edge and a coring knife case containing the coring blade. The coring blade is configured to extend out of the coring knife case. The coring knife case is configured to be selectively positioned and locked at any one of a plurality of locations between the key and the coring abutment prior to extension of the coring blade out of the coring knife case.

In other aspects, the coring knife case includes a stop feature configured to fit in an alignment feature of a separate device for aligning the coring knife prior to extension of the coring blade out of the coring knife case In other aspects, the coring knife further comprises a detent mechanism that selectively locks and unlocks the coring knife case at any one of the plurality of locations between the key and the coring abutment.

The features and advantages of the invention will be more readily understood from the following detailed description which should be read in conjunction with the accompanying drawings.

BRIEF DESCRIPTION OF THE FIGURES

FIG. 3a is a perspective view of a variation of the attachment ring.

FIG. 3b is a cross-sectional view of A-A of FIG. 3a.

FIG. 4a is a perspective view of a variation of the attachment ring.

FIG. 4b is a cross-sectional view of FIG. 4a.

FIG. 5 illustrates a variation of the clamp.

FIGS. 6a and 6b illustrate a variation of the clamp in opened and closed configurations, respectively.

FIGS. 7a and 7b illustrate a variation of the clamp on the attachment ring with the clamp in opened and closed configurations, respectively.

FIG. 8a illustrates a variation of the attachment ring attached to the inflow conduit.

FIG. 8b is a perspective view of section B-B of FIG. 8a.

FIG. 8c is the variation of cross-section B-B of FIG. 8a shown in FIG. 8b.

FIG. 9a illustrates a variation of the attachment ring attached to the inflow conduit.

FIG. 9b is a perspective view of section B'-B' of FIG. 9a.

FIG. 9c is the variation of cross-section B'-B' of FIG. 9a shown in FIG. 9b.

FIGS. 10a and 10b are a perspective views of a variation of the valvular structure.

FIGS. 10c-10e are perspective views of a variation of section C-C.

FIGS. 16a and 16b illustrate open and closed configurations, respectively, of a variation of the valvular structure of section C-C.

FIGS. 17a and 17b illustrate open and closed configurations, respectively, of a variation of the valvular structure of section C-C.

FIGS. 18a and 18b are exploded and top views of a variation of the valve.

FIGS. 19a and 19b are perspective and sectional views of a variation of the valve integrated with an attachment ring.

FIG. 21c is a bottom perspective view of the valve of FIG. 21a with the diaphragm flap shown in see-through.

FIG. 23 illustrates a variation of the valvular structure with the housing shown in see-through.

FIG. 24 illustrates a variation of the valvular structure with the housing in see-through.

FIG. 25 is a sectional view of a variation of a method for attaching the valvular structure to the attachment ring.

FIGS. 26a and 26b are sectional views of a variation of a method for attaching the valvular structure to the attachment ring.

FIG. 29a illustrates a variation of the tunneler.

FIGS. 29b and 29c illustrate variations of the tunneler of FIG. 29a with the bullet tip removed.

FIG. 30a illustrates a variation of the tunneler.

FIG. 30b illustrates the tunneler of FIG. 30a with the outer sheath removed from the tunneler shaft.

FIG. 31 illustrates a variation of the tunneler attached to the outflow conduit.

FIGS. 36a and 36c are perspective and side views, respectively, of a variation of the coring knife.

FIGS. 36b and 36d are perspective and side views of a variation of section F-F of FIG. 36a.

FIG. 36e is a side view of a variation of section F-F of FIG. 36a with the coring blade in a retracted configuration.

FIG. 39b is a perspective end view of FIG. 39a.

FIGS. 40a through 40i illustrate a variation of a method for using a variation of the ventricular assist device system.

FIGS. 41a through 41d illustrate a variation of a method for coring.

FIGS. 42a through 42c illustrate a variation of inserting the inflow conduit through the attachment ring.

FIGS. 46a-46d show an attachment ring, FIGS. 46b and 46d being partial cross-sectional sectional views.

FIGS. 50a and 50b are plan and perspective views of a clamp for use on an attachment ring, showing ratcheting teeth for locking the clamp closed.

FIG. 51 is a plan view of a clamp for use on an attaching ring with one pair of teeth.

FIGS. 53a-53f are perspective and partial plan views of a coring knife for making a circular incision in the heart.

DETAILED DESCRIPTION

As used herein, any term of approximation such as, without limitation, near, about, approximately, substantially, essentially and the like mean that the word or phrase modified by the term of approximation need not be exactly that which is written but may vary from that written description to some extent. The extent to which the description may vary will depend on how great a change can be instituted and have one of ordinary skill in the art recognize the modified version as still having the properties, characteristics and capabilities of the modified word or phrase. For example without limitation, something that is described as "substantially circular" in shape refers to a shape that is perfectly circular and a shape that one skilled in the art would readily recognize as being circular even though diameters measured at multiple locations on the circle are not exactly the same. As another non-limiting example, a first structure that is described as "substantially parallel" in reference to a second structure encompasses an orientation that is perfectly parallel and an orientation that one skilled in the art would readily recognize as being parallel even though distances between corresponding locations on the two respective structures are not exactly the same. In general, but with the preceding discussion in mind, a numerical value herein that is modified by a word of approximation may vary from the stated value by ±15%, unless expressly stated otherwise.

Variations of a system and method for implanting a VAD during a beating-heart procedure are disclosed. The system can minimize or prevent blood loss from the heart during the system implantation procedure, notably during the steps of coring a portion of the epicardial wall and insertion of the inflow conduit through the epicardial wall. The system can provide a fluid-tight seal around the surgical tools used to access or come into contact with the internal fluid volume of the heart. Throughout this disclosure, one should appreciate that references made to VADs equally applies to all heart assist devices. Similarly, the system and surgical tools may apply to a similar procedure of cannulation to other parts of the heart or of the cardiovascular system.

Figure 1:
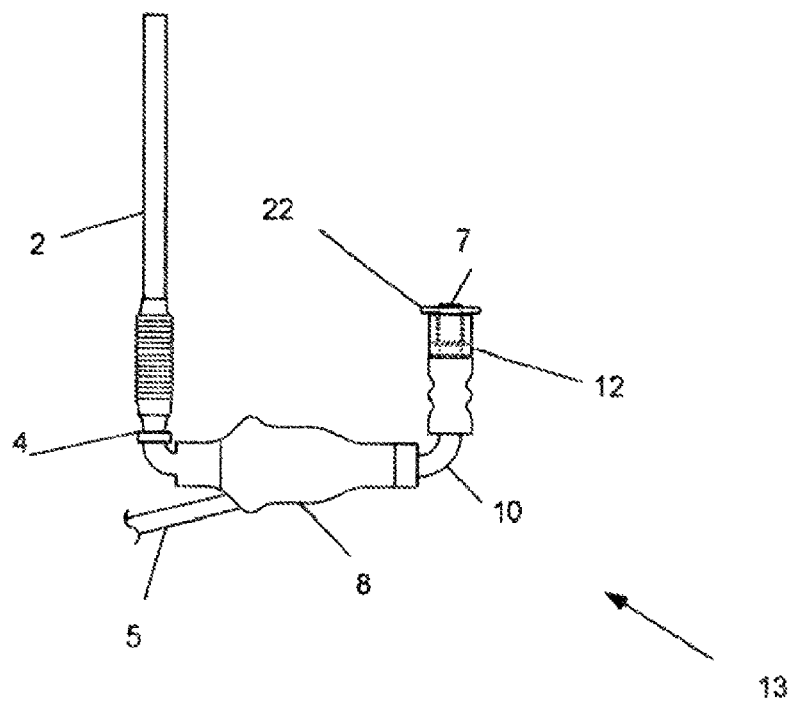
FIG. 1 illustrates a variation of the ventricular assist system.

FIG. 1 illustrates a ventricular assist device (VAD) system 13 with a pump 8. All locations described as proximal or distal, herein, are relative to the location of the pump 8. The pump 8 can draw blood from the left ventricle, and deliver the blood to the aorta at a higher pressure to assist the pumping of the heart. The pump 8 is configured to direct blood flow from one location (e.g., the heart) to a second location (e.g., target vasculature like an aorta) in the vascular system to provide mechanical circulatory support/assistance. For example, the pump 8 can be configured as a unidirectional turbine pump 8 to direct blood from the inflow side of the pump 8 (e.g., from the heart) to the outflow side of the pump 8 (e.g., to the aorta). A percutaneous lead 5 having insulated wires can be used for transmission and/or receiving of data and/or power between the pump 8 and a controller and/or a remote device for controlling the operation of the pump 8. In one variation, a controller or remote is outside of the patient's body. The pump 8 can have any configuration including but not limited to having axial flow or centrifugal flow.

The pump 8 can be directly attached to or have an inflow conduit 10 at a first end of the pump 8 and directly attached to or have an outflow conduit 2 at a second end of the pump 8.

The inflow conduit 10 can be coupled with the pump 8 by a helically threaded coupler configured to attach to the inflow port 7 of the pump 8.

The inflow conduit 10 can have a hollow channel for fluid communication such as directing blood from a first location (e.g., the heart) to the pump 8. In one variation, the inflow conduit 10 can be flexible. In another variation, the inflow conduit 10 can be rigid, such as a metal tube. In yet another variation, the inflow conduit 10 may have a combination of rigid and flexible elements such as having a proximal (relative to the pump 8) rigid elbow for coupling with the pump 8 that is connected to a flexible middle portion to accommodate for bending and a distal rigid portion (relative to the pump 8) for coupling with the heart. The inflow conduit may also be formed by a portion of the pump body.

As illustrated in FIG. 1, the inflow conduit 10 has a distal end that can be placed through the valvular structure 12 and the attachment ring 22 before entering into the heart after implantation. A flexible middle portion of the inflow conduit 10 provides strain relief between the distal end and the proximal end. The proximal end is coupled with the pump 8. Blood can enter the inflow conduit 10 through its distal opening, travel along the length of the inflow conduit 10, and enter the pump 8 at the inflow port 7 of the pump 8 after exiting the proximal opening of the inflow conduit 10. The inflow conduit 10 can be integral with, or separate and attachable to, the pump 8.

The valvular structure 12 is configured to prevent or minimize blood loss from the heart during the implantation of the VAD. The valvular structure 12 can be removed from the system and the patient once the inflow conduit 10 is properly positioned relative to the heart, for example, after the inflow conduit 10 has been inserted into the attachment ring 22. The valvular structure 12 can seal against a coring knife and/or the inflow conduit 10 which passes through a channel through the valvular structure 12. The valvular structure 12 can minimize or prevent blood flow out from the heart during the implantation of the VAD. Additionally the valvular structure 12 can provide for passage of other instruments during the procedure while preventing blood loss out of the heart.

The valvular structure 12 can be directly attached to an attachment ring 22, for example, indirectly attaching the valvular structure 12 to the apex of the heart during use. The attachment ring 22 can be configured to connect to a ventricle. The attachment ring 22 can fix and seal against the inflow conduit 10 once the VAD is implanted. The attachment ring 22 can be a ventricle or heart connector. The attachment ring 22 can fixedly attach to the VAD to the wall of the heart. Thus, the attachment ring 22 is configured to be secured against the heart, and is also configured to be secured against the inflow conduit 10.

An outflow conduit is coupled to the second end (e.g., outflow port) of the pump 8 where the blood or fluid exits the pump 8. In an axial flow pump arrangement, the outflow conduit 2 is approximately linear and opposite to the inflow conduit 10. Similar to the inflow conduit 10, a proximal end (relative to the pump 8) of the outflow conduit 2 is coupled to the pump 8, whereas the distal end (relative to the pump 8) of the outflow conduit 2 is for coupling to a target vasculature (e.g., aorta) where blood re-enters the circulatory system after exiting the pump 8.

Similar also to the inflow conduit 10, the proximal end of the outflow conduit 2 can be rigid for coupling to the pump 8. The middle portion of the outflow conduit 2 can be made from a flexible material for bend relief. In one variation, the distal portion of the outflow conduit 2 (relative to the pump 8) can be a flexible sealed graft that can be sewn onto a target vasculature (e.g., aorta) by way of an anastomosis, for blood to re-enter the circulatory system.

The ventricular assist system can have fluid communication between the inflow port 7, the inflow conduit 10, the pump 8, the outflow conduit 2 and the outflow port. The components of the ventricular assist system shown in FIG. 1, except for the valvular structure 12, can all or partially be from a Heartmate II Left Ventricular Assist Device (from Thoratec Corporation, Pleasanton, Calif.).

Figures 2A, 2B:
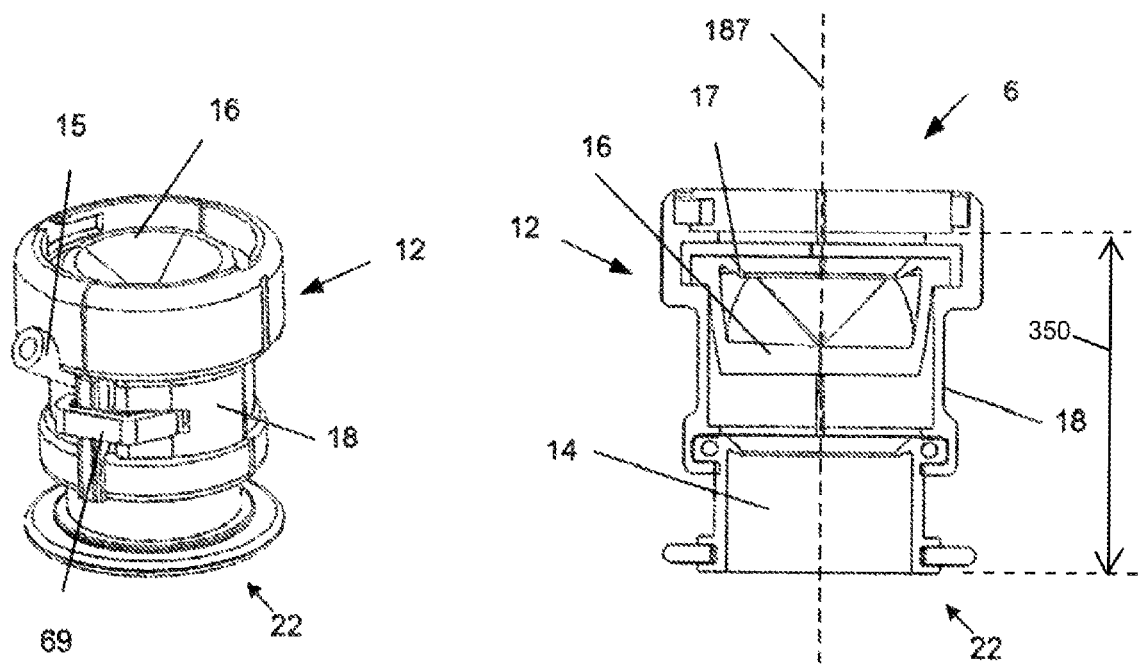
FIGS. 2a and 2b are perspective and sectional views of a variation of the attachment ring attached to the valvular structure.

FIGS. 2a and 2b illustrate a valvular structure 12. In conjunction with other components in a system, this valvular structure 12 helps to prevent or otherwise minimize blood loss out of the heart during the implantation or cannulation procedure, for example, when an opening is created in the heart while the heart is beating, or when a heart-lung by-pass machine is not used. The valvular structure 12 has a housing 18 that can be substantially cylindrical with a valve 16 and/or one or more seals 17 coupled to the inside wall of the structure. The valve 16 can act as either a complete or a partial seal for the valvular structure 12. The valve 16 can allow the flow of fluid or entry of an element in a distal direction and substantially impair or completely prevent the flow of fluid or entry of an element in a proximal direction. The housing 18 and valve 16 can be configured to be attachable to and removable from the attachment ring 22. The housing 18 can be separatable and removable from the valve 16. The housing 18 can have an attachment ring channel 14 around the inner circumference of the housing 18. The attachment ring 22 can be positioned inside of the attachment ring channel 14 and at or near one end of the housing 18. The attachment ring 22 and valvular structure 12 can have longitudinal axes 187. The longitudinal axis of the attachment ring 22 and the longitudinal axis of the valvular structure 12 can be co-axial.

A de-airing channel 15 can be configured through the wall of the housing 18. In the process of cannulation or implantation, air can be introduced into the valvular structure 12. Air entering the circulatory system can cause air embolism and can be harmful to a patient. The de-airing channel 15 can be used for purging all the air from the valvular structure 12 prior to insertion of the inflow conduit 10 into the heart thus preventing air from entering the circulatory system. In one variation, suction can be applied to and/or a fluid such as saline and/or blood can be delivered through the de-airing channel 15 to remove air from the system before the system is completely assembled. The de-airing channel 15 can place the environment radially external to the surface of the housing 18 in fluid communication with the attachment ring channel 14.

FIGS. 3a and 3b illustrate an attachment ring 22. The attachment ring 22 can be attached to the epicardial wall, for example, by sutures through the cuffs 19 and 21 and the epicardial wall. After being sutured to the heart, the cuffs 19 and 21 can provide at least mechanical support on the heart wall for the attachment ring 22, which serves as an anchoring point for securing of the inflow conduit 10 after it has been inserted into the heart for fluid (e.g., blood) communication. The attachment ring 22 can have an attachment ring wall 29 that defines an attachment ring channel 14. The attachment ring channel 14 can be open at both ends. The inflow conduit 10 can be passed through the attachment ring channel 14, accessing the chamber inside the ventricle. The attachment ring 22 can have a substantial or nominal height. The attachment ring wall 29 can be made from a silicone molded body with ABS, Delrin, or combinations thereof. The attachment ring 22 can have polypropylene ring inserts (e.g., to provide circular structure to facilitate tool and inflow conduit 10 insertion) and reinforced polyester mesh (e.g., to prevent tearing). The attachment ring wall 29 can be sutured to the cuff 19 and/or 21. The cuff pad 20 can be made from PTFE felt.titanium, silicone, or combinations thereof. The attachment ring 22 can be from about 5 mm to about 25 mm tall. The attachment ring wall 29 can have a thickness from about 1 to about 3 mm (e.g., not including flanges). The diameter of the attachment ring channel 14 can range from about 10 mm to about 25 mm.

The attachment ring wall 29 can have a distal band 31 extending radially from the attachment ring wall 29 at or near the distal terminus of the attachment ring wall 29. The distal band 31 can be integral with the attachment ring wall 29. The distal band 31 can attach to the distal and/or proximal cuff 21. The attachment ring wall 29 can have a proximal band 26 at or near the proximal terminus of the attachment ring wall 29 to maintaining a substantially circular cross-section adjacent to where the inflow conduit 10 is inserted into the attachment ring channel 14. The proximal band 26 can be a rigid metal or plastic. The proximal band 26 can structurally reinforce the proximal end of the attachment ring wall 29. The attachment ring wall 29 can be flexible or rigid. These proximal and distal bands 26 and 31 can be used as anchors, attachment points, visual alignment indicators and/or locks to other structures, components, or tools used in the implantation process.

The attachment ring 22 can be attached to the heart by stitching, suturing, or stapling one or more regions on the cuff 19 and/or 21 of the attachment ring 22 to the heart. The attachment ring wall 29 is attached to the cuff 19 and/or 21 having an annular shape with a distal cuff 19 or sewing region and a proximal cuff 21 or sewing region. For example, the cuffs 19 and/or 21 can be attached to the attachment ring 22 by sutures, thread, staples, brads, welding, adhesive, epoxy, or combinations thereof. The cuffs 19 and 21 extend radially from the attachment ring wall 29 outward. The distal cuff 19 can extend radially more outward than the proximal cuff 21, for example, the proximal cuff 21 can structurally support the distal cuff 19 and provide a thicker layer through which sutures can be stitched. The distal cuff 19 and the proximal cuffs 21 can form the shape of cylindrical discs with hollow centers (i.e., where the attachment ring wall 29 and attachment ring channel 14 are located). The distal cuff 19 can be on the distal side of the distal band 31, and the proximal cuff 21 can be on the proximal side of the distal band 31 and attached to the distal band 31 and/or the attachment ring wall 29. The distal and proximal cuffs 21 can be stacked. The distal cuff 19 can be attached to the proximal cuff 21, for example, at the radially outer circumference of the proximal cuff 21.

The cuffs 19 and/or 21 can each have a cuff pad 20 through which the sutures can be passed. The cuff pads 20 can be made from a mesh or fabric material that can be configured to allow penetration by a typical surgical needle and suture. The material of the cuff pad 20 can be strong enough such that the cuff 19 and/or 21 can be secured by sutures against the epicardial wall without easily tearing should a small force be exerted on the attachment ring 22 by accidentally tugging the attachment ring 22 away from the epicardial wall. The cuff pads 20 can be flexible. The cuff pads 20 can be configured to affix to sutures passed through the cuff pads 20.

The cuffs 19 and/or 21 can have cuff frames 23 that maintain the planar shape of the cuffs. The cuff frames 23 can also prevent the suture from tearing through the cuff pad 20 and radially exiting and detaching from the cuff. The cuff frames 23 can be rigid circular bands attached to the external circumference of the cuff pads 20. The cuff frames 23 can be metal and/or hard plastic. The suture can be passed through the cuff pad 20 radially inside of the cuff frame 23.

The attachment ring wall 29 can have a ring wall interface lip 25 that can prevent the clamp 24 from shifting, slipping, or otherwise coming off the attachment ring wall 29. The ring wall interface lip 25 can extend radially from the attachment ring wall 29 proximal from the cuffs 19 and 21.

An integral or separately attached clamp 24 can be on the attachment ring wall 29 distal to ring wall interface lip 25 and proximal to the cuffs 19 and/or 21. The clamp 24 can apply an inward radial force against the attachment ring wall 29. The clamp 24 can exert a compressive radially force around the attachment ring wall 29, for example, to pressure-fit the inner surface of the attachment ring wall 29 to the outer surface of an inflow conduit 10 when the inflow conduit 10 is passed through the attachment ring channel 14. The compressive force from the clamp 24 can hold and seal the attachment ring 22 against the inflow conduit 10. The attachment ring seal 34 can prevent blood flow from the heart from exiting between the attachment ring 22 and the inflow conduit 10. The inflow conduit 10 can separately seal around the cored hole in the epicardium. The clamp 24 can be on the radial outside of the attachment ring wall 29 between the ring wall interface lip 25 and the cuffs.

FIGS. 4a and 4b illustrate that the attachment ring 22 can have an attachment ring seal 34 at the proximal end of the attachment ring wall 29. The attachment ring seal 34 can extend radially inward from the attachment ring wall 29 into the attachment ring channel 14. The attachment ring seal 34 can be flexible. The attachment ring seal 34 (and any other seals disclosed herein) can be made from a soft, resilient elastomer or other polymer. The attachment ring seal 34 can be integral with or separate and attached to the attachment ring wall 29. The attachment ring seal 34 can produce a fluid-tight seal against elements placed in the attachment ring channel 14, when the element in the attachment ring channel 14 has an outer diameter larger than the inner diameter of the attachment ring seal 34.

The proximal band 26 can be inside of the ring wall interface lip 25. The ring wall interface lip 25 can extend radially outward from the attachment ring wall 29. The ring wall interface lip 25 can interference fit against the clamp 24 to prevent the clamp 24 from translating proximally off the attachment ring wall 29. The ring wall interface lip 25 can be attached to and/or abutted against by an element adjacent to the attachment ring 22. For example, the inflow conduit 10 can abut against the ring wall interface to prevent the inflow conduit 10 from passing too far through the attachment ring channel 14. Also for example, the valvular structure 12 can attach to the ring wall interface lip 25. The proximal band 26 also provides structural support and a hemostatic seal when the attachment ring wall interface lip 25 and valvular structure housing 18 are joined together.

The attachment ring 22 can have one cuff 35. The attachment ring wall 29 can have a first distal band 32 on a distal side of the cuff 35 and a second distal band 33 on a proximal side of the cuff 35. The cuff 35 can be attached to, or pressure fit between, the first distal band 32 and the second distal band 33.

FIG. 5 illustrates that the clamp 24 can be made of a single, continuous wire of material. The clamp 24 can be made from a metal and/or polymer (e.g., plastic). The clamp 24 can have a clamp frame 37 to transmit the radially compressive force and clamp handles 36 that can be used to open and/or close the clamp frame 37. The clamp frame 37 can be resiliently deformable. The clamp frame 37 can have a clamp diameter 38. When the clamp 24 is in a substantially or completely relaxed or unbiased configuration, the clamp diameter 38 can be smaller than the outer diameter of the attachment ring wall 29 to which the clamp 24 attaches.

The clamp handles 36 can extend radially from the remainder of the clamp frame 37. Compressive, squeezing force can be applied to the opposite clamp handles 36 to move the clamp handles 36 toward each other. The compressive force applied to the clamp handles 36 can expand the clamp diameter 38, placing the clamp 24 in an open configuration.

When the clamp 24 is in an open configuration, the clamp 24 can be loaded onto and/or removed from the attachment ring 22. In the open configuration, an inflow conduit 10 can be passed through or retracted from the attachment ring channel 14.

FIGS. 6a and 6b illustrate another variation of the clamp 24. FIG. 6a illustrates the clamp 24 in an open configuration. The clamp 24 can have a frame made from a band of ribbon with a clamp handle 36 to loosen or tighten the clamp 24. The configuration as shown illustrates that a first end of the clamp lever 39 is rotatably attached to a first terminus of the clamp frame 37 and with the second end of the clamp lever 39 rotatably attached to the clamp handle 36. The clamp handle 36 can be rotatably attached to the second terminus of the clamp frame 37 that is not attached to the clamp lever 39. The clamp handle 36 can be attached to the clamp frame 37 at a clamp hinge 40.

FIG. 6b illustrates the clamp 24 in a closed configuration. In this illustration, the clamp handle 36 is rotated to cause the clamp frame 37 to tighten the clamp frame 37 in the closed configuration. The clamp handle 36 can lie flush against the outer circumference of a length of the clamp frame 37. The clamp lever 39 can position a first terminus of the clamp frame 37 toward the second terminus of the clamp frame 37 when the clamp handle 36 is closed.

The clamp diameter 38 can be smaller when the handle is closed than when the handle is open. When the handle is closed, the clamp diameter 38 can be smaller than the outer diameter of the attachment ring wall 29 to which the clamp 24 attaches. When the handle is open (as shown in FIG. 6a), the clamp diameter 38 can be larger than the outer diameter of the attachment ring wall 29 to which the clamp 24 attaches. When the handle is open, the clamp diameter 38 can be larger than the outer diameter of the ring wall interface lip 25.

FIG. 7a illustrates that the clamp 24 can be on the attachment ring 22 in an open configuration over the attachment ring external wall 29. With the clamp 24 in an open configuration, elements such as a coring knife, inflow conduit 10 or other surgical tools, can pass through the attachment ring channel 14. The clamp 24 can be against the outer surface of the attachment ring wall 29 between the ring wall interface lip 25 and the cuff 35.

FIG. 7b illustrates that the clamp 24 can be in a closed configuration over the attachment ring external wall 29. With the clamp 24 in a closed configuration, the attachment ring wall 29 can compress onto and seal against elements placed in the attachment ring channel 14, such as the inflow conduit 10. The clamp 24 can be between the second distal band 33 and the ring wall interface lip 25. The clamp 24 can exert a radially inward force against the attachment ring wall 29. The closed clamp 24 can reduce the diameter of the attachment ring wall 29 and the diameter of the attachment ring channel 14.

FIGS. 8a through 8c illustrate that the inflow conduit 10 can be inserted into the attachment ring 22 to access the heart with the inflow conduit 10 and route blood through an inflow conduit channel 178 from the heart to the pump 8. The inflow conduit 10 can have an inflow conduit stop 42 configured to abut against or attach to other elements, for example, to preventing the inflow conduit 10 from over-insertion through the attachment ring 22. The inflow conduit 10 distal to the inflow conduit stop 42 can have an outer diameter smaller than the inner diameter of the attachment ring channel 14. The inflow conduit stop 42 can have an outer diameter larger than the inner diameter of the attachment ring channel 14.

The clamp 24 can be biased open (e.g., by compressing the clamp handles 36 toward each other) when the inflow conduit 10 is inserted into the attachment ring channel 14, for example, to allow the inflow conduit 10 to pass freely through the attachment ring channel 14. The clamp 24 can be released and returned to a compressive state around the attachment ring wall 29 when the inflow conduit 10 is in a desired location within the attachment ring 22, for example, to clamp 24 the attachment ring 22 onto the inflow conduit 10 and hold the inflow conduit 10 in place.

FIGS. 9a through 9c illustrate that the variation of the clamp 24 of FIGS. 6a and 6b can be in an open configuration when the inflow conduit 10 is inserted into the attachment ring channel 14, allowing the inflow conduit 10 to be inserted freely through the attachment ring 22. The clamp handle 36 can be rotated open.

The inflow conduit 10 can be advanced through the attachment ring channel 14 until the inflow conduit stop 42 abuts the proximal end of the attachment ring wall 29, for example at the ring wall interface lip 25. The inflow conduit 10 can extend out of the distal end of the attachment ring 22, for example into and within fluid communication with the chamber of the heart.

When the inflow conduit 10 is in a desired location within the attachment ring 22, the clamp 24 can be closed or released, for example, compressing the attachment ring wall 29 onto the inflow conduit 10. The inflow conduit 10 can then pressure fit against the inner surface of the attachment ring wall 29, for example holding the inflow conduit 10 in place relative to the attachment ring 22.

FIGS. 10a through 10e illustrate a variation of the valvular structure 12 that can have a clamshell housing 18. The valvular structure 12 can have a housing 18 with a housing first portion 46 separatably attached to a housing second portion 54. The housing first portion 46 can have a rotatable clamshell attachment to the housing second portion 54 and can be rotated open and removed from the remainder of the ventricular assist system. In a closed configuration, the housing portions 46 and 54 can define a housing channel 58 longitudinally through the housing 18 and open on each end. The housing first portion 46 can attach to the housing second portion 54 at a housing first seam 51 and a housing second seam 48. The housing first seam 51 can have a housing first joint 50. The housing second seam 48 can have a housing second joint 49.

The housing joints 49 and 50 can be pinned hinges. For example, the first and/or second housing joints 49 and/or 50 can have first and/or second joint pins 52 and/or 53, respectively. The housing portions 46 and 54 can rotate about the housing joints 49 and 50. The respective pins 52 and 53 can be removed from the housing joints 49 and 50 and the housing portions 46 and 54 can be separated from each other at the housing joint 49 and 50. After separation, the housing portions 46 and 54 can be reassembled at the housing joints 49 and 50 and the joint pins 52 and 53 can be reinserted into the housing joints 49 and 50. When the housing 18 is separated at one or both joints 49 and 50, the valve 16, which is a discrete and separate element from the housing 18, can come out of the housing 18 or otherwise be removed or detached from the housing 18.

One or both of the housing portions 46 and 54 can have de-airing ports 62. The de-airing ports 62 can be the ends of the de-airing channels 15. Air can be suctioned out of the de-airing ports 62 and/or saline or blood can be delivered from inside the housing 18 through the de-airing ports 62 to remove the air from the volume between the valve 16 and the heart wall during the de-airing process.

The valve 16 can have first, second, third, and fourth valve leaflets 56. The leaflets 56 can be flexible and resilient. The leaflets 56 can be made from an elastomer. The valve 16 can have inter-leaflet seams 64 between adjacent leaflets 56. Each leaflet 56 can have an intra-leaflet fold 66. Each leaflet 56 can have a leaflet rib 57 or reinforcement on the inter-leaflet seam 64 or intra-leaflet fold 66, for example to reinforce the leaflet 56 at the seam 64 or fold 66. The leaflets 56 can allow fluids and solids to move in the distal direction through the housing channel 58. The leaflets 56 can oppose fluids and solids moving in the proximal direction through the housing channel 58. The leaflets 56 can close against pressure from the distal side of the leaflets 56, for example, preventing the flow of blood from the heart out of the valvular structure 12.

The valve 16 can have a valve seal 60 proximal to the leaflets 56. The valve seal 60 can extend radially into the housing channel 58. The valve seal 60 can be resilient. The valve seal 60 can seal against an element, such as the coring knife or inflow conduit 10, located in the housing channel 58. When the leaflets 56 are spread open, the valve seal 60 between the seal and the coring knife or inflow conduit 10 can prevent the flow of blood from the heart past the valve seal 60 and out of the valvular structure 12.

The housing 18 can have a housing seal 47 distal to the valve 16. The housing seal 47 can seat in, and attach to the housing 18, via a circumferential housing seal groove 55 in the housing 18. The housing seal 47 can extend radially into the housing channel 58. The housing seal 47 can be resilient. Similar to the valve seal 60, the housing seal 47 can seal against an element, such as the coring knife or inflow conduit 10, located in the housing channel 58. When the leaflets 56 are spread open, the seal between the housing seal 47 and the coring knife or inflow conduit 10 can prevent the flow of blood from the heart out past the housing seal 47.

The valve 16 can have a valve shoulder 59 that extends radially from the base of the valve leaflets 56. The valve shoulder 59 can seat and interference fit into a valve groove 61 recessed in the inner surface of the housing 18. The valve shoulder 59 can hold the valve 16 in the valve groove 61.

Figure 11A:
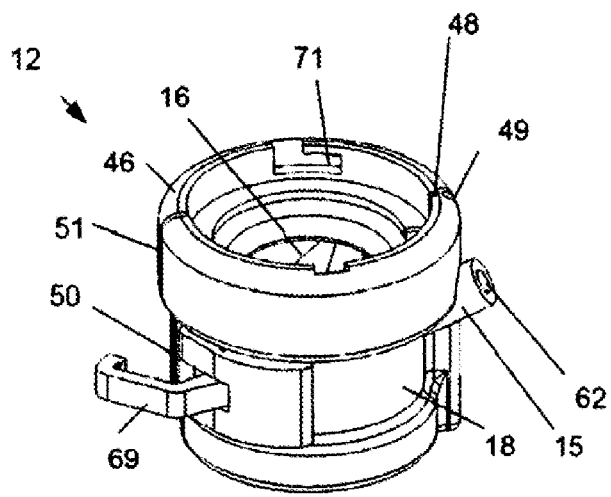
FIGS. 11a through 11c are bottom perspective, top perspective, and top views, respectively, of a variation of the valvular structure.
Figure 11B:
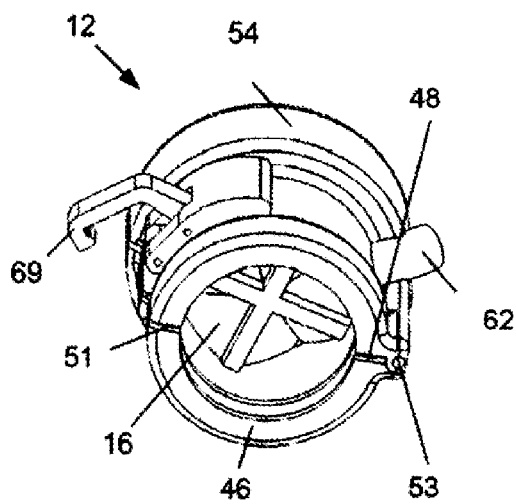
Figure 11C:
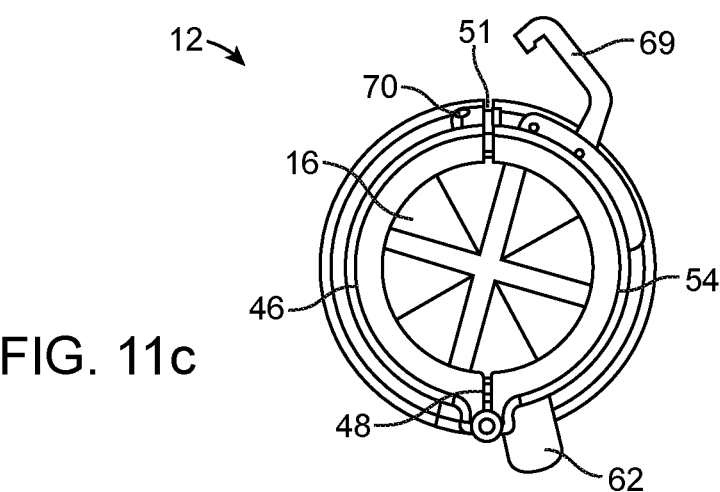

FIGS. 11*a* through 11*c* illustrate another variation of the valvular structure 12 that can have a latching closure configuration. The housing 18 of this variation of the valvular structure 12 can latch closed, as shown in FIGS. 2*a* and 2*b*, locking the housing first portion 46 to the housing second portion 54 in a closed configuration. The housing 18 can also be opened by unlatching the housing first portion 46 to the housing second portion 54.

The housing 18 can have a first joint that can have a first joint latch 69. The joint latch can be rotated open (as shown), decoupling the housing first portion 46 and the housing second portion 54 at the housing first seam 51. The first joint latch 69 can be rotated closed, laying substantially flush with the outer wall of the housing 18. In a closed configuration, the first joint latch 69 can be closed onto and attach to a first joint catch 70. The first joint latch 69 can be on the housing second portion 54, the first joint catch 70 can be on the housing first portion 46.

When the housing first portion 46 is separated from the housing second portion 54, the housing 18 can be removed from the valve 16. The valve 16 is destructible and can be torn away from the ventricular assist structure by hand or with a knife and removed from the target site after the housing 18 is removed. For example, after the inflow conduit 10 is inserted through the attachment ring 22 and the housing 18 is removed, the valve 16 can be torn away from the inflow conduit 10.

The housing first portion 46 and/or housing second portion 54 can each have coupling grooves 71 proximal to the valve 16. The coupling grooves 71 can be configured to slidably and lockably interface with radially extending locking tabs 181 on other components that can interact with the housing 18 such as the slitting blade case 158, coring knife, inflow conduit 10, or combinations thereof. The locking tabs 181 and couple groove can interface to hold, fix, or otherwise releasably couple the component inserted through the housing 18 to the housing 18 and to align the component inserted through the housing 18 to the housing 18. For example, the locking tabs 181 and coupling groove 71 can cause a slit from a slitting blade case 158 to be at the same angular orientation and position as a coring abutment disc later-inserted through the slit, as shown in FIGS. 40*b* and 40*c*.

Figure 12A:
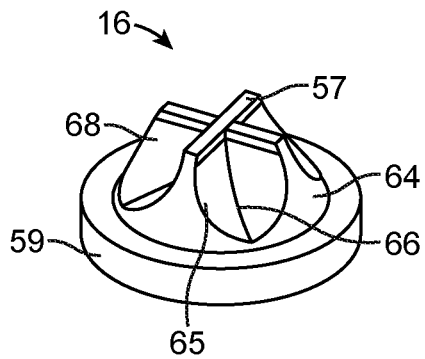
FIGS. 12a and 12b illustrate perspective and section views, respectively, of a variation of the valve in a closed configuration.

FIGS. 12*a* through 15*b* illustrate variations of the valve 16 with different configurations. FIGS. 12*a* and 12*b* illustrate that the valve 16 shown in FIGS. 10*a* through 10*e* can be a four-leaflet valve 16. The inter-leaflet seams 64 can extend radially from the center of the valve 16 to the valve shoulder 59 with no inter-leaflet seam extending through the valve shoulder 59 or through the valve shoulder 59 to the outer circumference of the valve 16, or combinations thereof. For example, as shown in FIG. 12*c*, one of the inter-leaflet seams 64 can extend through the valve shoulder 59 while the remainder of the inter-leaflet seams 64 can extend to the valve shoulder 59 without extending through the valve shoulder 59, and the one inter-leaflet seam 64 that extends through the valve shoulder 59 can be aligned with one of the housing seams 51 or 48 when loaded in the housing 18.

Figure 12C:
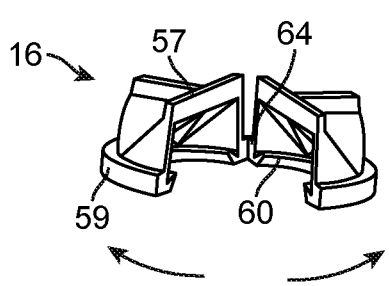
FIG. 12c is a perspective view of the valve of FIGS. 12a and 12b in an open configuration.

The inter-leaflet seams 64 can be completely separated seams, perforations, or combinations thereof along the length of the seam (e.g., complete separation between the leaflets 56 and perforation as the seam extends through the valve shoulder 59). The valve 16 can be tearable by hand, for example along the inter-leaflet seam 64. For valves 16 with a completely separated inter-leaflet seam 64, no tearing is necessary to separate the valve 16 from an element which the valve 16 surrounds, such as the inflow conduit 10. As shown in FIG. 12*c*, the valve can be rotated open, as shown by arrows, in a clamshell configuration to release the valve 16 from an inner element or component which the valve 16 surrounds.

Figure 13A:
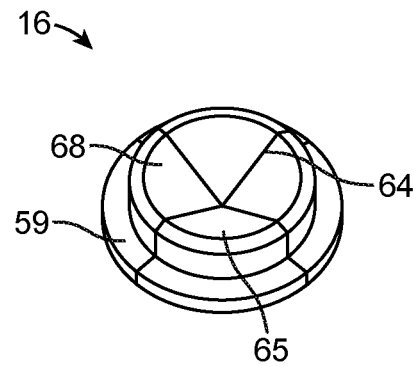
FIGS. 13a and 13b are top perspective and bottom perspective views of a variation of the valve in a closed configuration.
Figure 12B:
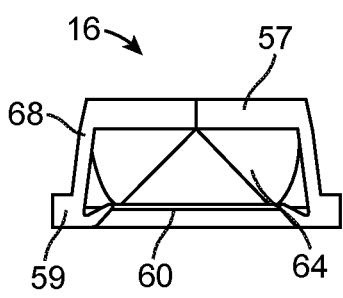
Figure 13B:
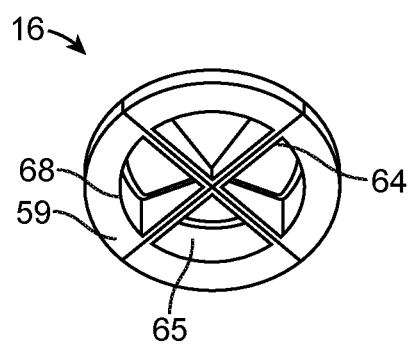
Figure 13C:
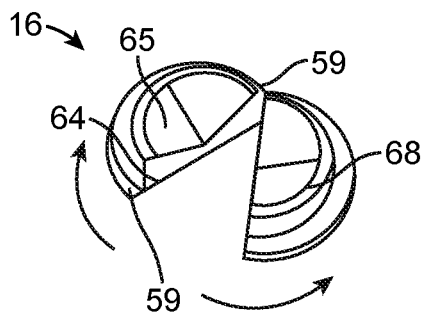
FIGS. 13c and 13d are top perspective views of the valve of FIGS. 13a and 13b in open configurations.
Figure 13D:
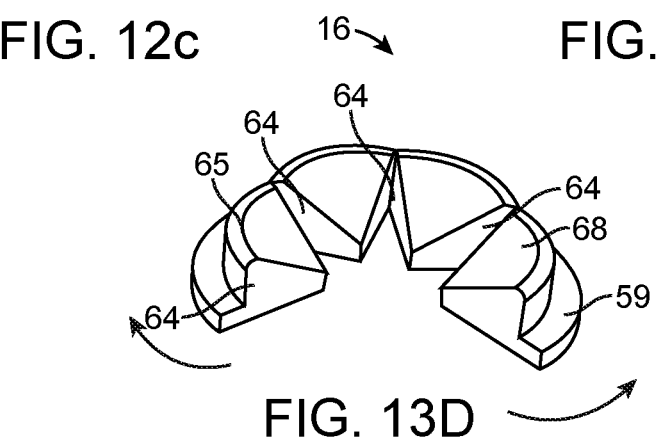

FIGS. 13*a* through 13*c* show another variation of the valve 16. The valve 16 can be a quadcuspid (i.e., four-leaflet) valve that can have inter-leaflet seams 64 that can extend through the valve shoulder 59 to the outer circumference of the valve 16. FIG. 13*c* illustrates that the valve 16 can be rotated open, as shown by arrows, at a first interleaflet seam 64 that extends through the valve shoulder 59 between the first leaflet 68 and the second leaflet 65. The opposite inter-leaflet seam 64 can extend to, but not through the valve shoulder 59, acting as a hinge around which the valve halves can rotate. FIG. 13D illustrates that the remaining inter-leaflet seams 64—other than the inter-leaflet seam 64 that extends through the valve shoulder 59 between the first leaflet 68 and second leaflet 65—can extend to but not through the valve shoulder 59. The valve 16 can be further rotated open to spread open each inter-leaflet seam 64, for example when removing the valve 16 from the coring tool or inflow conduit 10 placed through the valve 16.

Figure 14A:
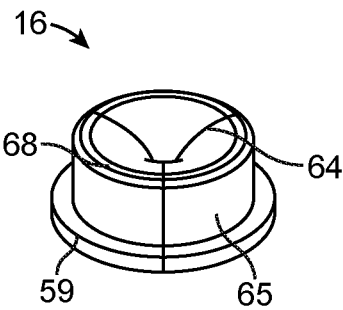
FIGS. 14a and 14b are top perspective and bottom perspective views of a variation of the valve.
Figure 14B:
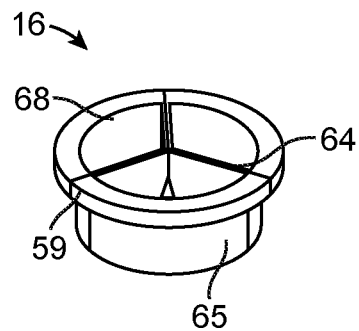
Figure 15A:
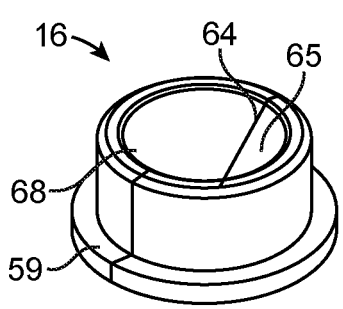
FIGS. 15a and 15b are top perspective and bottom perspective views of a variation of the valve.
Figure 15B:
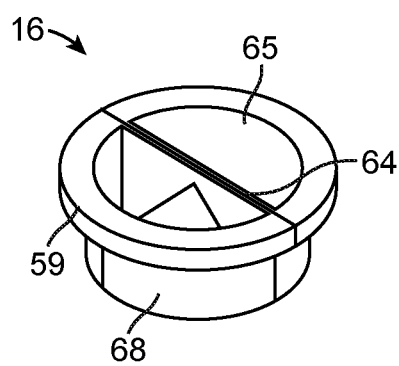

FIGS. 14*a* and 14*b* illustrate yet another variation of the valve 16 that can be a tricuspid valve (i.e., having three leaflets). FIGS. 15a and 15b illustrate yet another variation of the valve 16 that can be a bicuspid valve (i.e., having two leaflets).

Figure 15C:
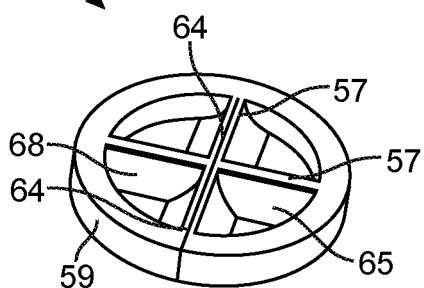
FIGS. 15c through 15e illustrate variations of miter valves.
Figure 15D:
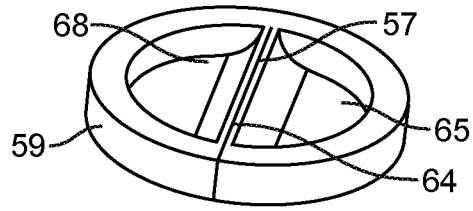
Figure 15E:
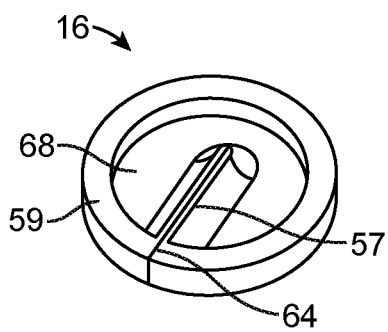

FIGS. 15c through 15e illustrate variations of the valve 16 that can have opposite inter-leaflet seams 64 that extend through the shoulder on a first side of the valve 16, and not through the shoulder on a second side of the valve 16, opposite to the first side of the valve 16. The opposite inter-leaflet seams 64 can converge in the middle of the valve 16 to form a single slit along a diameter of the valve 16. The valves 16 can be miter valves. The leaflets can join together at miters or bevels at the inter-leaflet seams 64. The leaflets can pucker or duckbill at the inter-leaflet seams 64.

FIG. 15c illustrates a quadcuspid valve 16. FIG. 15d illustrates a bicuspid valve 16. FIG. 15e illustrates a unicuspid valve 16 (i.e., having one leaflet) that can have a seam that does not extend to the valve shoulder. A unicuspid valve is a type of diaphragm valve. A diaphragm valve can have no more than one seam extending to the shoulder. The seam can be similar in length to the diaphragm seam 88 shown in FIGS. 21a and 21b.

Figure 15F:
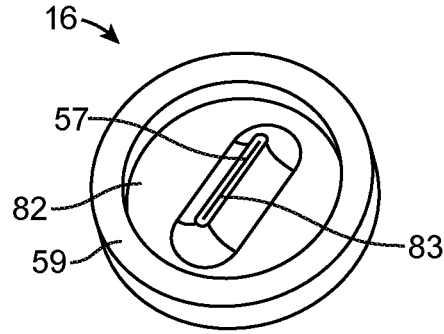
FIG. 15f illustrates a variation of a duckbill diaphragm valve.

FIG. 15f illustrates a diaphragm valve 16 that can have a diaphragm 82 but no leaflets. The seam in the valve 16 can be a straight slit or port 83 that can be closed in a relaxed an unbiased configuration. The slit or port 83 can extend along a diameter of the valve 16, but not extend to the valve shoulder 59. The valve 16 can duckbill, pucker or miter around the port 83.

FIGS. 16a and 16b illustrate a variation of the valvular structure 12 that can have a valve 16 that can be an inflatable membrane 73. The valve 16 can be inflated and deflated to close and open, respectively, the valve 16. The valve 16 can have an inflatable valvular chamber 75 between the inflatable membrane 73 and the housing 18. The inflatable membrane 73 can be resilient. The inflatable membrane 73 can be in a deflated and open configuration, as shown in FIG. 16a.

FIG. 16b illustrates that the inflatable membrane 73 can be in an inflated and closed configuration. The inflatable valvular chamber 75 can be pressurized, as shown by arrows, with a liquid (e.g., saline) or gas (e.g., carbon dioxide) to inflate the inflatable membrane 73. The inflatable membrane 73 can seal around elements in the housing channel 58, such as the coring knife or inflow conduit 10. The inflatable membrane 73 can have a high-friction surface facing the housing channel 58 that can pressure-fit against the coring knife or inflow conduit 10, fixing the coring knife or inflow conduit 10 in the housing channel 58. Alternatively, the inflatable membrane 73 can have a low-friction surface facing the housing channel 58 that can allow the coring knife of inflow conduit 10 to slide within the housing channel 58 against the inflated inflatable membrane 73.

The pressure in the inflatable valvular chamber 75 can be released, returning the inflatable membrane 73 to the open configuration and releasing the pressure-fit against any elements in the housing channel 58.

FIG. 17a illustrates a variation of the valvular structure 12 that can have a valve 16 that can be a torsioning or twisting membrane 77. The top and bottom of the housing 18 can be counter-rotated to open or close the twisting membrane 77. The twisting membrane 77 can be loose and non-resilient or taught and resilient and elastic. The housing first portion 46 and second portion can each have a top rotatably attached to a bottom. The twisting membrane 77 can be attached to housing tops 78 (the housing first portion top is shown) and bottoms 79 (the housing first portion bottom is shown) by a membrane anchor ring 76. The twisting membrane 77 can be in an untwisted and open configuration, as shown.

FIG. 17b illustrates that the housing tops 78 can be rotated with respect to the housing bottoms 79, as shown by arrows, for example, to partially or completely close the valve 16. The twisting membrane 77 can twist upon itself and around elements in the housing channel 58. The twisting membrane 77 can be in a twisted and closed configuration. The tops and bottoms can be counter-rotated to untwist and open the twisting membrane 77.

FIGS. 18a and 18b illustrate another variation of the valve 16 that can be a diaphragm valve that can be closed in an unbiased configuration and stretched open when the inflow conduit 10 or coring knife is pushed through the diaphragm valve. The valve 16 can have a first diaphragm 80 and a second diaphragm 86. The diaphragms can be made from resilient material, such as an elastomer, or combinations thereof. For example, the diaphragm can be made from silicone, polyurethane or other blood compatible polymers. The first diaphragm 80 can be in contact with and attached to the second diaphragm 86.

The first diaphragm 80 can have a first diaphragm port 81 that can receive the inflow conduit 10 or coring knife. The second diaphragm 86 can have a second diaphragm port 85 that can also receive the inflow conduit 10 or coring knife. The diaphragm ports can be circular. The diaphragm ports can be resiliently expandable. For example, when a solid element, such as the inflow conduit 10 or coring knife, with a diameter larger than the diaphragm ports is forced through the diaphragm ports the diaphragm ports can expand in shape and size to allow the solid element to pass through the ports and can seal against the solid element. When the solid element is removed from the diaphragm ports, the diaphragm ports can return to the relaxed, unbiased, shape and size of the diaphragm port.

The first diaphragm 80 can have a diaphragm interface lip 84. The diaphragm interface lip 84 can be used to hold to diaphragm in the valve groove 61 in the housing 18. The diaphragm interface lip 84 can be a ring around the outer circumference of the first diaphragm 80 that can be raised or thickened compared to the remainder of the first diaphragm 80. The diaphragm interface lip 84 can be formed a result of the attachment of the second diaphragm 86 and the first diaphragm 80. For example the diaphragm interface lip 84 can be a rib formed by fusing, gluing or welding, or a reinforcement.

The second diaphragm 86 can have a diameter smaller than the diameter of the first diaphragm 80. The second diaphragm 86 can be attached to the first diaphragm 80 at or near the outer circumference of the second diaphragm 86. The second diaphragm 86 can attach to the first diaphragm 80 on the diaphragm interface lip 84 or on the face of the first diaphragm 80 on the opposite side of the diaphragm interface lip 84.

When the first diaphragm 80 and the second diaphragm 86 are attached, the first diaphragm port 81 can be incongruous from (i.e., not overlapping with) the second diaphragm port 85 when the first and second diaphragms 80 and 86 are in relaxed, unbiased configurations. When the diaphragm valve 16 is in a relaxed, unbiased configuration, the first diaphragm port 81 and the second diaphragm port 85 can overlap completely, partially or not at all (as shown). The diaphragm valve 16 can have a substantially fluid-tight seal in a relaxed configuration.

The diaphragm valve 16, or other valve variations such as the leaflet valves, can allow a check flow, for example a small amount of blood flow used to test or confirm if positive blood pressure exists on the opposite side of the valve 16. For example, the pressure between the first diaphragm 80 and the second diaphragm 86 can be insufficient to completely seal when pressurized blood from the heart is in contact with the diaphragm valve 16, and a small trickle or drip-flow of blood can pass through the diaphragm ports 81 and 85. In an alternative variation, the leaflets can have a check flow channel, a small channel longitudinally aligned in the inter-leaflet seam that can allow check flow to flow between adjacent leaflets in a direction opposite to the low-resistance orientation of valve.

Figure 19C:
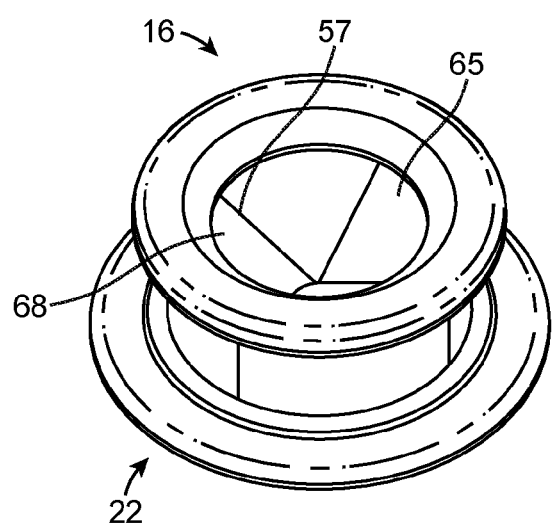
FIGS. 19c and 19d are perspective and sectional views of a variation of the valve integrated with an attachment ring.
Figure 19D:
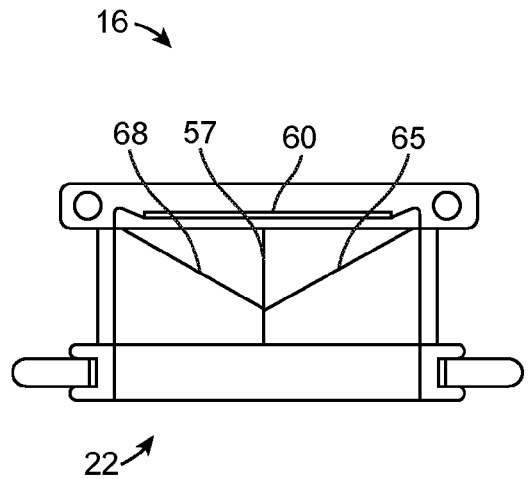
Figure 20:
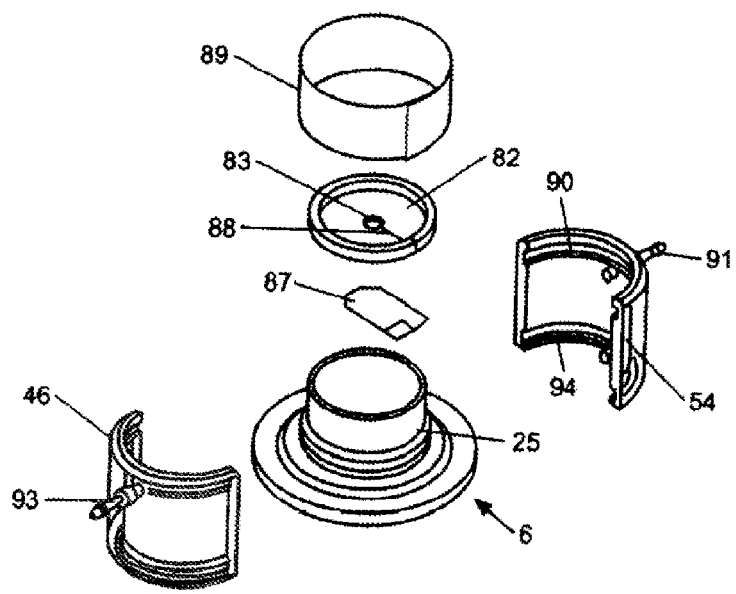
FIG. 20 illustrates a variation of the attachment ring and an exploded view of a variation of the valvular structure.

FIGS. 19*a* and 19*b* illustrate a variation of the attachment ring 22 with an integrated diaphragm valve 16. The first diaphragm 80 can be integral with the attachment ring wall 29. The first diaphragm 80 can substantially close the end of the of the attachment ring channel 14. The second diaphragm 86 can be attached to the first diaphragm 80 and/or the attachment ring wall 29. Similarly, the other valve types described can also be integrated with the attachment ring 22. For example, FIGS. 19*c* and 19*d* illustrates a variation of the attachment ring 22 integrated with a quadcuspid valve 16. FIG. 20 illustrates the exploded assembly of a variation of the diaphragm valve 16 in a valvular structure 12 attached to an attachment ring 22. The valve 16 can be separate and detachable from the attachment ring 22. The diaphragm 82 can be attached to a diaphragm flap 87. The housing first portion 46 and housing second portion 54 can have a diaphragm groove 90 circumferentially around the radially inner surface of the housing 18. The diaphragm interface lip 84 can seat in and attach to the diaphragm groove 90.

The housing first portion 46 and housing second portion 54 can have a ring groove 94 circumferentially around the radially inner surface of the housing 18. The ring wall interface lip 25 can seat in and attach to the ring groove 94.

The housing first portion 46 can have a housing first handle 93. The housing second portion 54 can have a housing second handle 91. The housing handles 91 and 93 can be pulled to separate the housing first portion 46 from the housing second portion 54. For example, the housing first seam 51 and the housing second seam 48 can be completely separated or perforated.

The tape 89 can be a substantially unresilient, flexible polymer strip tightly wrapped around the radial outer surface of the housing 18. The tape 89 can radially compress the housing first portion 46 and the housing second portion 54, keeping the housing first portion 46 attached to the housing second portion 54. The tape 89 can have an adhesive applied to the radial inner surface. The tape 89 can be wound once or more around the housing 18 and can stick to the housing 18 and to inner layers of the tape 89 itself.

Alternatively, the tape 89 can be an elastomeric hollow cylinder or band. The tape 89 can be placed onto the housing 18 by stretching the tape 89 over the housing 18 and releasing the tape 89 from the stretching force, resiliently radially compressing the housing 18.

Figure 21B:
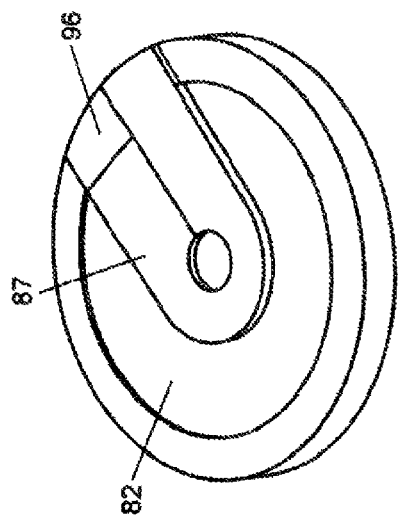
FIG. 21b is a variation of cross-section D-D of the valve.
Figure 21A:
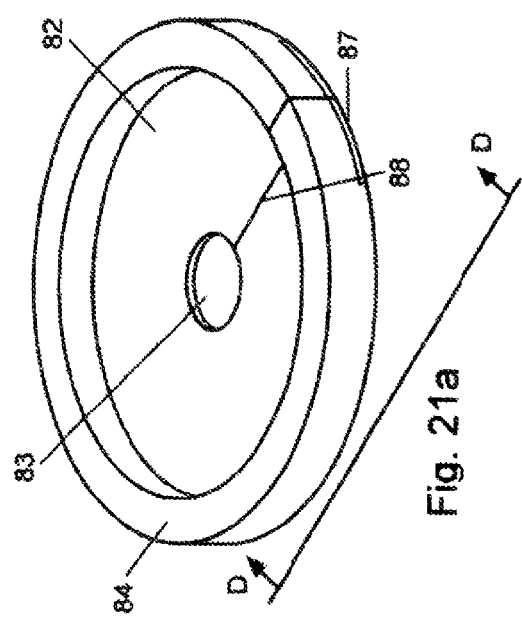
FIG. 21a is a top perspective view of a variation of the valve.
Figure 21C:
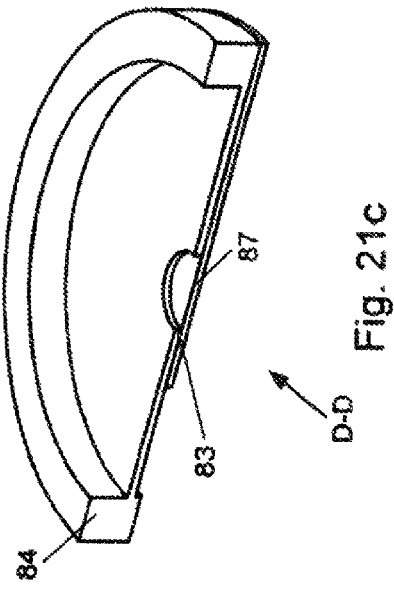

FIGS. 21*a* through 21*c* illustrate another variation of the diaphragm valve 16. FIG. 21*b* illustrates that the diaphragm 82 can have a diaphragm seam 88 extending from the diaphragm port 83 to the external circumference of the diaphragm 82. The diaphragm seam 88 can be a complete split separating each side of the diaphragm seam 88, allowing an element, such as the inflow conduit 10 or coring knife, to pass through the diaphragm 82 at the diaphragm port 83 and/or the diaphragm seam 88. The diaphragm port 83 can be in the radial center of the diaphragm 82. The diaphragm flap 87 can cover the diaphragm port 83.

FIG. 21*c* illustrates that the diaphragm flap 87 can attach to the diaphragm 82 at an attachment area 96. The diaphragm flap 87 can be unattached to the diaphragm 82 except for at the attachment area 96, allowing the diaphragm flap 87 to open out of the way when an element is pushed through the diaphragm port 83 and/or diaphragm seam 88. The diaphragm flap 87 can be rigid or flexible. The diaphragm flap 87 can be resilient. The diaphragm flap 87 can be made from the same materials as the diaphragm 82.

The diaphragm flap 87 can extend to the external circumference. The diaphragm flap 87 can cover the diaphragm port 83 and the diaphragm seam 88. The diaphragm flap 87 can cover a portion of the side of the diaphragm 82 and leave a portion of the side of the diaphragm 82 exposed (as shown) or can cover the entire side of the diaphragm 82.

When the fluid pressure on the side of the diaphragm 82 of the diaphragm flap 87 exceeds the fluid pressure on the side of the diaphragm 82 opposite the diaphragm flap 87, the diaphragm flap 87 can press against the diaphragm seam 88 and diaphragm port 83, further sealing the diaphragm 82.

When an element, such as the coring knife or inflow conduit 10, is forced through the diaphragm 82 from the side of the diaphragm 82 opposite of the diaphragm flap 87, the element can press open the diaphragm 82 at the diaphragm port 83 and diaphragm seam 88, and the diaphragm flap 87 can be pressed aside as the element moves through the diaphragm 82.

Figure 22:
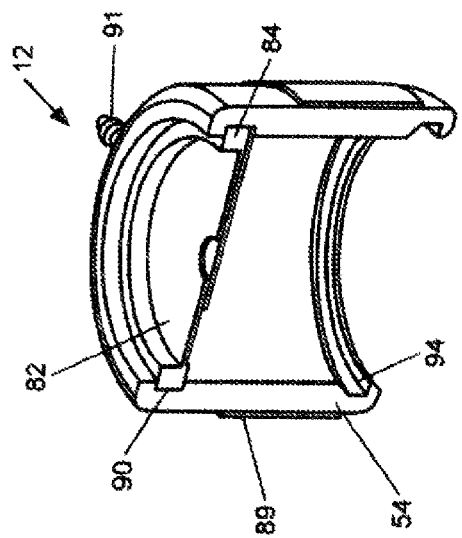
FIG. 22 is a sectional view of a variation of the valvular structure.

FIG. 22 illustrates that when the valvular structure 12 is assembled the diaphragm interface lip 84 can be seated in the diaphragm groove 90 of the housing 18. The housing first portion (not shown) and the housing second portion 54 can be compressed together by tape 89 wound around the external circumference of the housing 18.

FIG. 23 illustrates that the valvular structure 12 can have a locking ring 98 that can be used to compress the attachment ring 22 against an inflow conduit 10 placed in the attachment ring channel 14. For example, the locking ring 98 can be used in lieu of or in addition to the clamp 24. The locking ring 98 can be releasably attached to the radially internal surface of the housing 18. The locking ring 98 can be separably attached to the housing 18 with circumferential rails and interfacing grooves on the radially outer surface of the locking ring 98 and the radially inner surface of the housing 18.

The de-airing ports 62 (as shown) can act as handle ports and/or be used to de-air the valvular structure 12. The handle ports can attach to housing handles or can be open to be used for de-airing, as described herein.

FIG. 24 illustrates that the tape 89 can be wound radially around the outer surface of the housing 18. The tape 89 can compress the housing first portion 46 to the housing second portion 54. The tape 89 can have adhesive, for example, on the side of the tape 89 facing the housing 18. The tape 89 can have no adhesive and be elastic, for example, attaching to the outer surface of the housing 18 by a friction-fit from the tape 89 elastically compressing against the housing 18.

FIG. 25 illustrates that the valvular structure 12 can be attached to the attachment ring 22, for example, by snapping the valvular structure 12 onto the attachment ring 22. The valvular structure 12 can be attached to the attachment ring 22 before or during the VAD implant procedure.

The valvular structure 12 can be translated, as shown by arrow, over the attachment ring wall 29. The ring wall interface lip 25 can have a sloped side facing in the direction of the on-loading valvular structure 12. As the valvular structure 12 is being pressed onto the attachment ring 22, the portion of the housing 18 that is distal to the ring groove 94 can deform over the sloped side of the ring wall interface lip 25. The ring wall interface lip 25 can then seat and interference fit into the ring groove 94.

Figure 26B:
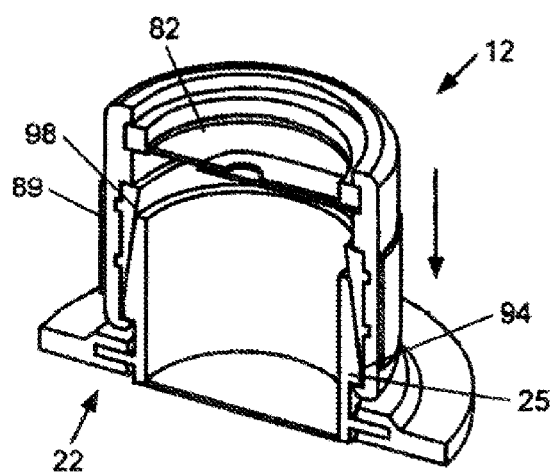

FIGS. 26*a* and 26*b* illustrate another variation of snapping the valvular structure 12 onto the attachment ring 22. In this variation, the valvular structure 12 can have a locking ring 98. The locking ring 98 can have a locking ring wall angle 100 with respect to the housing channel longitudinal axis 103. The locking ring wall angle 100 can be, for example, from about 3° to about 15°, for example about 10°.

The ring wall interface lip 25 can have a sloped side facing in the direction of the on-loading valvular structure 12. The sloped side of the ring wall interface lip 25 can form a ring wall angle 102 with the attachment ring channel longitudinal axis 101. The ring wall angle 102 can be from about 3° to about 15°, for example about 10°. The ring wall angle 102 can be substantially equal to the locking ring wall angle 100.

The valvular structure 12 can be pressed onto the attachment ring 22, over the attachment ring wall 29, as shown by arrow. As the valvular structure 12 is being pressed onto the attachment ring 22, the portion of the housing 18 distal to the ring groove 94 can deform over the sloped side of the ring wall interface lip 25.

FIG. 26b illustrates that the valvular structure 12 can be pressed onto the assembly ring, as shown. The ring wall interface lip 25 can seat and interference fit into the ring groove 94.

Method of Using

Figure 27A:
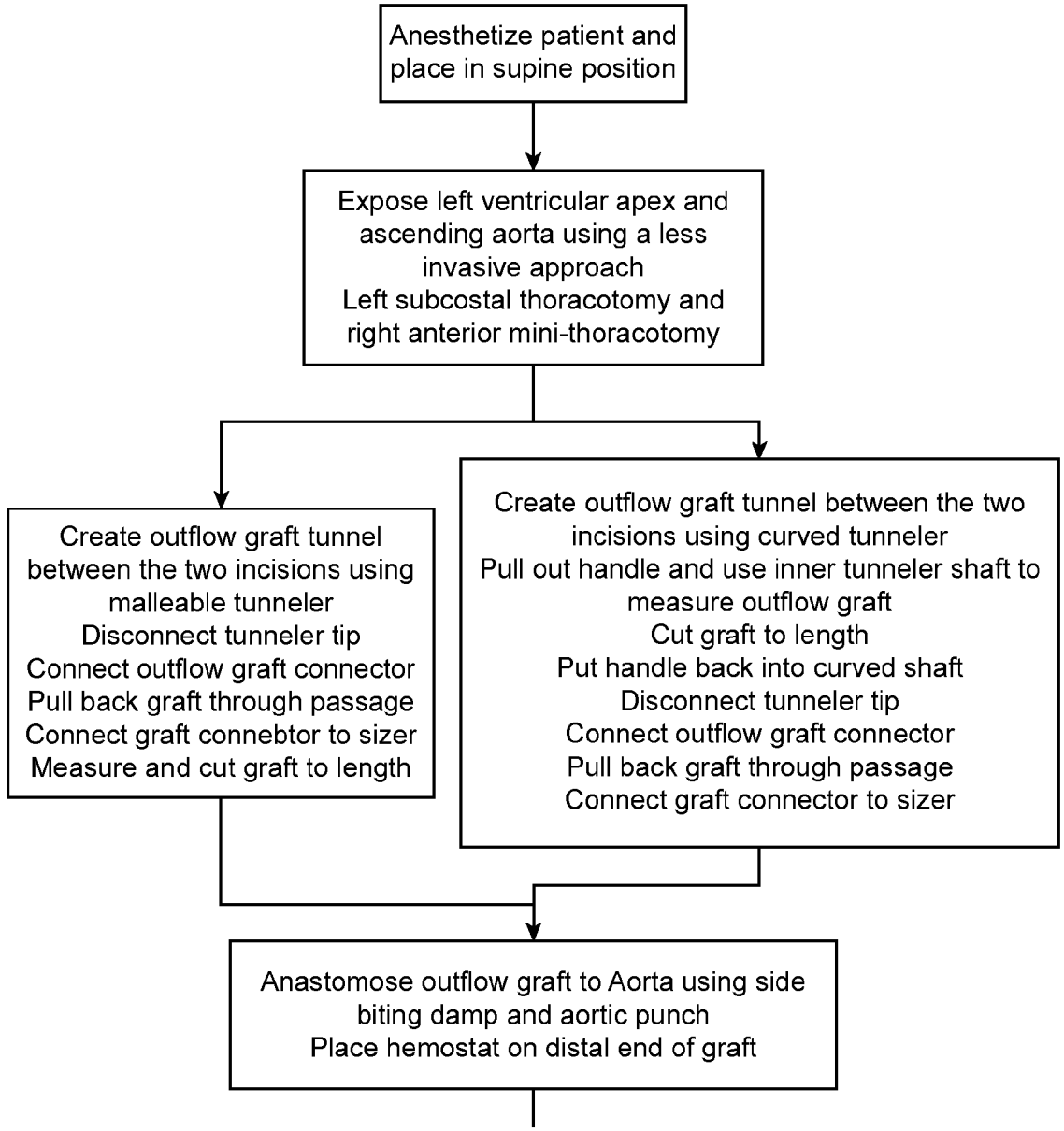
FIGS. 27a and 27b illustrate a variation of the method process flow for implanting a variation of the ventricular assist system.
Figure 27B:
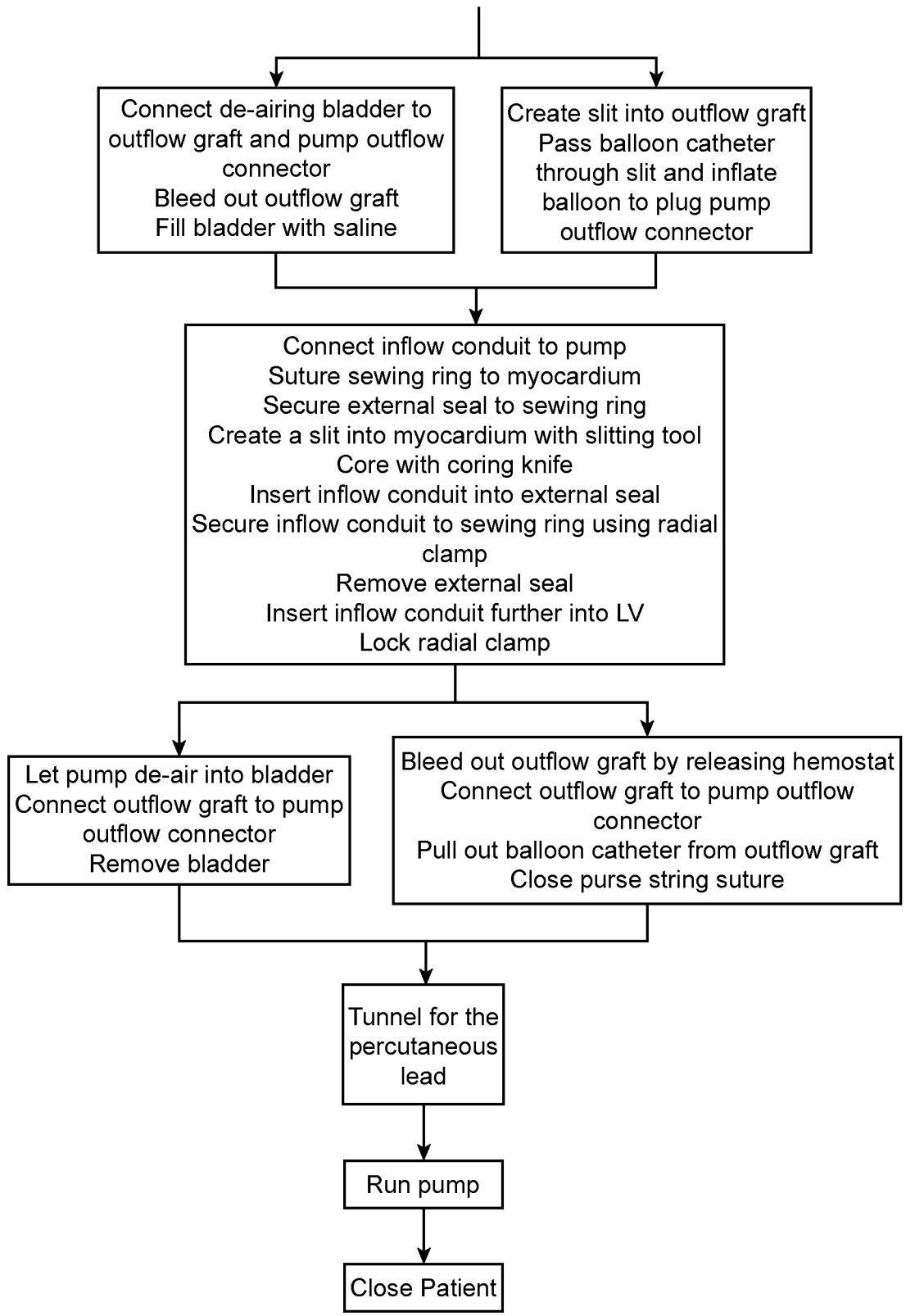

FIGS. 27a and 27b illustrate a process for surgically implanting a ventricular assist system. It should be appreciated to a person with ordinary skills in the art that the surgical, preparation, and implantation processes described can be performed in a different order as presented. The surgical process for implanting the ventricular assist system can begin by anesthetizing the patient and placing the patient in a supine position. The left ventricular apex and ascending aorta 104 can then be exposed using a less invasive approach, such as a left subcostal incision and a second right anterior mini-thoracotomy, or a common sternotomy which is typically more invasive but allows more space for a surgeon to operate.

The method can include space for placement of an outflow conduit 2/graft by tunneling from a subcostal position to an aortic location. For example, an outflow graft tunnel can be created between the two incisions (e.g., the left subcostal incision and the right anterior mini-thoracotomy) with a malleable tunneler and/or a curved tunneler. The tunneler 177 can begin at the left subcostal thoracotomy and tunnel to the right anterior mini-thoracotomy.

The tunneler 177 can have a tunneler tip that can then be removed from the tunneler once the tunneler has reached the right anterior mini-thoracotomy. The outflow graft connector can then be attached to the end of the tunneler and pulled back through the tunnel created between the incisions. The outflow graft can then be connected to a pump sizer at the target site for the pump 8. The pump sizer is a plastic element the size and shape or the pump 8 that can be used to check the fit of the finally deployed pump 8 by inserting the pump sizer at the target site before inserting the pump 8.

With the outflow graft attached to the pump sizer, the outflow graft can be measured and cut to length to fit the space between the pump 8 and the aorta 104 with enough slack in the outflow conduit 2 to allow movement of the pump 8 and organs, but not too much slack to enable kinking of the outflow conduit 2.

If the process does not include the use of a heart-lung by-pass machine and is performed while the heart 106 is pumping, the outflow graft can then be anastomosed to the aorta 104 using a side biting clamp to hold the aorta 104 and an aortic punch 126 to make the incision in the aorta 104.

After blood is allowed to flow into the outflow graft for purging air from inside the outflow graft or conduit 2, a clamp 131, such as a hemostat, can then be placed on the outflow graft 2, or a balloon 135 can be inflated in the outflow graft to stanch the flow of blood from the aorta 104 through the outflow graft 2. The control of blood from the heart 106 and de-airing can also or additionally be performed by creating a slit into the wall of the outflow graft 2. A balloon catheter 132 can then be delivered into the outflow graft 2 through the slit. The balloon 135 can then be positioned in the pump outflow connector and inflated to plug the pump outflow connector. End and or side ports on the balloon catheter 132 can be used for de-airing.

The pump 8 and the inflow conduit 10 or inflow graft can be prepared prior to connection of the inflow conduit 10 to the heart 106. The proximal end of the inflow conduit 10 is connected to the pump 8 in a saline bath to purge all air from the inflow conduit 10 and the pump 8 prior to having the distal end of the inflow conduit 10 connected to the heart 106. In this preparation process, the entire inflow conduit 10 and the pump 8 can both be submerged into a saline bath and connected. A blockage at the outflow end of the pump 8 is placed to prevent blood from escaping after the distal end of the inflow conduit 10 is connected to the heart 106.

Prior to connection of the inflow conduit 10 to the heart 106, the attachment ring 22 can be sewed onto the epicardial surface of the target connection area on the heart 106. In one variation, sutures can be used to secure the cuff 35 of the attachment ring 22 onto the heart 106. The valvular structure 12 or external seal can then be secured against the attachment ring 22, for example, by placing and securing the valvular structure 12 over the walls forming the attachment ring channel 14. A slitting blade or tool can be inserted through the valvular structure 12 and the attachment ring 22 to create a slit into the myocardium at the target connection area. A coring knife 140 can then be inserted through the slit and used to core a portion of the myocardium. The inflow conduit 10 can then be inserted through the valvular structure 12 and the attachment ring 22 to into the opening of the heart 106 created by the coring knife. The inflow conduit 10 can be secured to the attachment ring 22 with the radial clamp 24. The valvular structure 12 including the external seal can then be removed. The inflow conduit 10 can be inserted further into the left ventricle. The radial clamp 24 can then be radially compressed (e.g., released from a radially expanded configuration) and/or locked to secure the inflow conduit 10 to the attachment ring 22.

The entire system can be completely de-aired in the process of connecting the outflow graft to the pump 8. De-airing or the removal of all the air from the outflow graft and the pump 8 can be performed with the use of a de-airing bladder, enclosure or a bath of saline. The unconnected end of the outflow graft can be submerged into the bath of saline along with the outflow end of the pump 8 that has the blockage. The clamp or balloon 135 can be removed from the outflow graft and all the air in the outflow graft and pump 8 can be allowed to escape or pushed by the flow of blood from the aorta 104 into the bladder, enclosure, or the bath of saline, for de-airing. Similarly, the outflow end of the pump 8 with the blockage is also submerged into the saline bath. Once the hemostatic outflow graft clamp 131 is removed from the outflow graft and the blockage is removed from the outflow end of the pump 8, any air remaining in either the outflow graft or in the pump 8 will be allowed to escape into the saline bath or enclosure. If the balloon 135 had previously been inserted into the pump outflow connector, the de-airing can occur by releasing the hemostatic clamp 131 from the outflow graft 2 resulting in blood from the aorta 104 flooding and bleeding out the outflow graft 2. The outflow graft 2 can then be connected to the pump outflow connector. The balloon 135 can be deflated and the balloon catheter 132 can then be pulled out from outflow graft 2. The hole in the site of the outflow graft 2 used for introducing the balloon catheter 132 can then be closed with a purse string suture. The outflow graft 2 is connected to the outflow end of the pump 8 after air is removed from the system.

A tunnel can be formed for the percutaneous lead 5 to extend from the pump 8 out of the body. The pump 8 can then be turned on to run and assist the blood flow from the left ventricle. The surgical wounds on the patient can then be closed.

Figure 32:
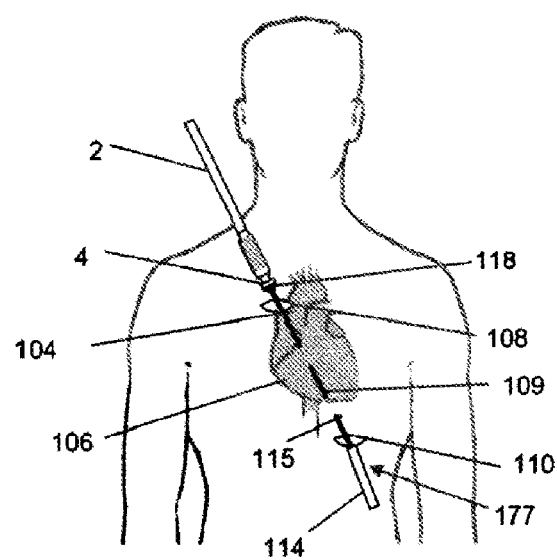
FIG. 32 illustrates a variation of inserting the outflow conduit in the target site.
Figure 35:
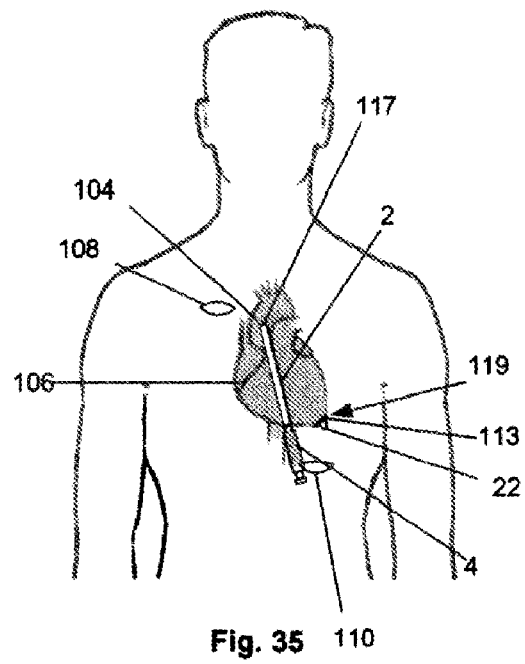
FIG. 35 illustrates a variation of a method of attaching the attachment ring to the apex of the heart.

FIGS. 28 to 35 will collectively illustrate the process of accessing the heart 106 and target implantation vasculature and the tools used to create a tunnel for an outflow conduit 2. FIGS. 28, 32 and 35 illustrate the process of creating a tunnel and implanting an outflow conduit 2 in the tunnel, and FIGS. 29a through 31 illustrate the variations of tools used for this tunnel creation process. FIGS. 33a through 33c illustrate the process and tools for creating an aortotomy 128 in the target vasculature for an anastomotic connection with the outflow conduit 2. FIGS. 34a through 34b illustrate the processes and tools for preventing blood from spilling out of the outflow conduit 2 after it is connected to the target vasculature.

Figure 28A:
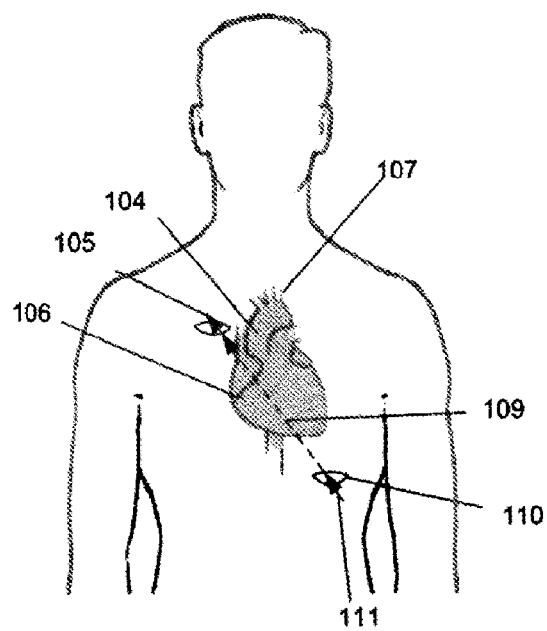
FIGS. 28a and 28b illustrate variations of a method for accessing the target site.
Figure 28B:
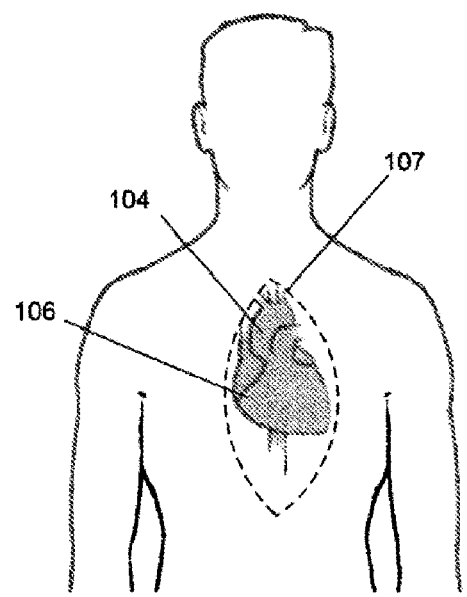

FIG. 28a illustrates the creation of a tunnel for the outflow conduit 2 without a sternotomy. FIG. 28b illustrates that when a sternotomy is performed, creating a sternotomy opening 107, there is no need to tunnel.

In a less invasive variation of the procedure, as shown in FIG. 28a, the target site can be accessed by making a first incision 110 caudally or inferior to the target site, for example just below the apex on the left side of the heart 106. A second incision 108 can be made cranial to the target site, on an opposite side of the target site from the first incision 110. The second incision 108 can be made near the right second intercostal to provide access to the aorta 104. The tunneler 177 can then be inserted, as shown by arrow 111, into the first incision 110 and tunneled between the first and second incision 110 and 108, as shown by arrow 109. The end of the tunneler 177 can then exit, as shown by arrow 105, from the patient at the second incision 108, or be inside the patient but accessible from the second incision 108.

FIGS. 29a to 30b illustrate variations of a tunneler 177 that can be used for creating the outflow conduit tunnel FIG. 29a illustrates one example of a tunneler 177 that can have an elongated tunneler shaft 115. The tunneler 177 can have a tunneler handle 114 at a proximal end of the tunneler shaft 115. The tunneler shaft 115 can be straight when in a torsionally unstressed state. The tunneler shaft 115 is of a substantially smaller diameter than the distal attachment cone 118 so that it can be malleable or flexible for shaping into a configuration that fits the anatomy of the patient. The tunneler 177 can have a distal attachment cone 118 at the distal end of the tunneler shaft 115. In one variation, this distal attachment can be a bullet tip 124 at the distal end of the tunneler 177. The bullet tip 124 can have a smooth or flush seam with the distal attachment cone 118. The bullet tip 124 can be removed from the distal attachment cone 118 and expose or be replaced with different distal attachment interface configurations. For example, the bullet tip 124 can be attached to, or replaced with, a distal attachment collet 123 extending distally from the distal attachment cone 118, as shown in FIG. 29b. Similarly, the bullet tip 124 can be attached to, or replaced with, a distal attachment bolt 122 extending distally from the distal attachment cone 118, as shown in FIG. 29c. The distal attachment bolt 122 can have helical thread 121. The objective of the distal attachment bolt 122 and the distal attachment collet 123 are for attachment with a proximal end of the outflow graft as will be illustrated further below.

FIGS. 30a and 30b illustrate another variation of the tunneler 177 that can have an outer sheath 125 attached to the distal attachment cone 118. The tunneler shaft 115 can be separate from the outer sheath 125 and distal attachment cone 118. The outer sheath 125 can be of a diameter that is similar to the diameter of the distal attachment cone 118 and can be hollow. While the diameter of the tunneler shaft 115 and the outer sheath 125 differs, the outer sheath 125 and the tunneler shaft 115 can have substantially equal radii of curvature. The tunneler shaft 115 and outer sheath 125 can be rigid. The tunneler shaft 115 can be slidably received by the outer sheath 125.

The tunneler 177 can be inserted through the first incision 110 at a desired location in the abdomen and/or thorax to create the tunnel for ultimate placement of the outflow conduit 2. The bullet tip 124 can be configured with a blunt tip to atraumatically separate or create a path through tissue when the tunneler 177 is being inserted through the patient.

FIG. 31 illustrates that the bullet tip 124 can be removed and the outflow conduit coupler 4 can be attached to the distal attachment interface. The outflow conduit 2 can extend from the terminus of the tunneler 177. The tunneler 177 can be used to manipulate the location and orientation (i.e., rotate, twist, translate, steer) of the outflow conduit 2.

The outflow conduit 2 can be attached to the tunneler 177 after the distal end of the tunneler 177 is passed through the patient and out of, or adjacent to, the second incision site, such as a surgical opening near the aorta 104 like a right anterior mini thoracotomy or a mini sternotomy near the aorta 104. FIG. 32 illustrates that when the distal attachment interface is positioned at the distal end of the tunnel or out of the second incision 108, the bullet tip 124 can be removed from the distal attachment interface and the outflow conduit coupler 4 can be attached to the distal attachment interface. The tunneler handle 114 can then be pulled to draw the outflow conduit coupler 4 and outflow conduit 2 through the tunnel.

Figure 33A:
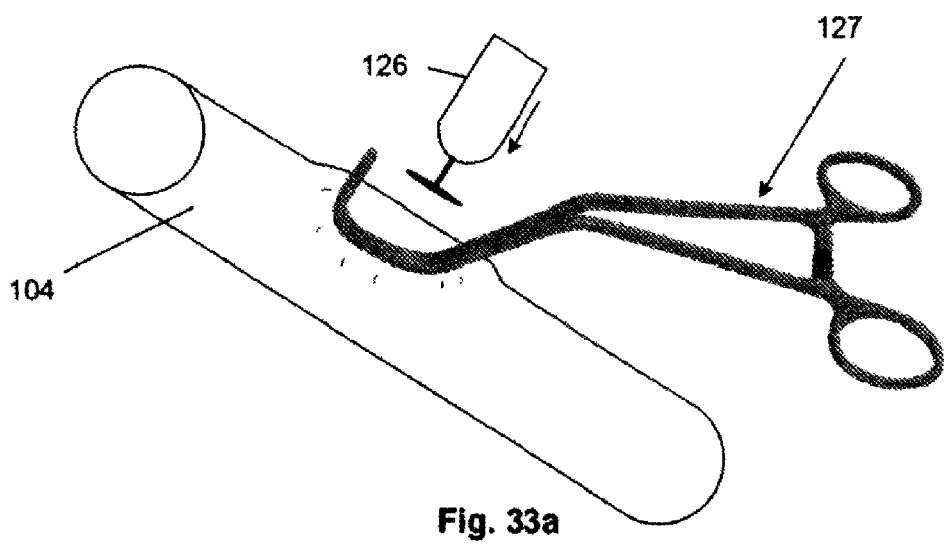
FIG. 33a through 33c illustrate a variation of a method for anastomosing the aorta to the outflow conduit.
Figure 33B:
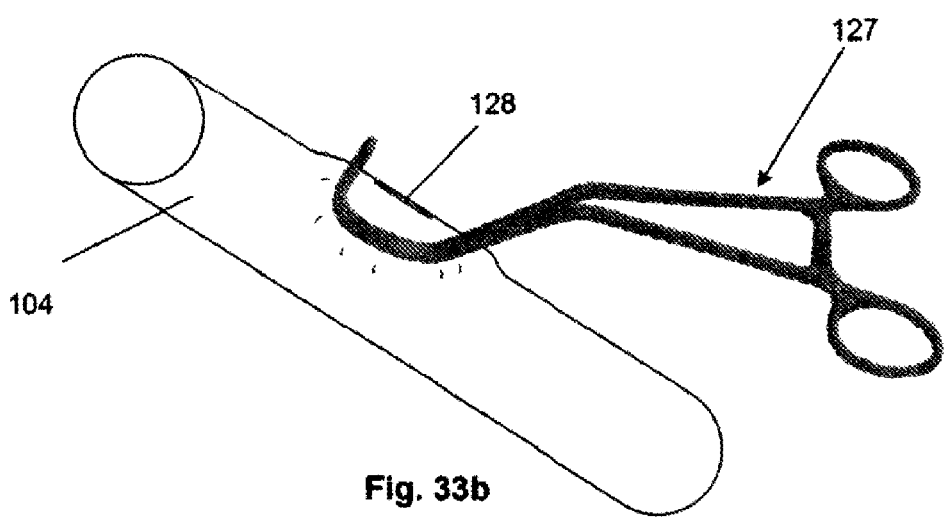
Figure 33C:
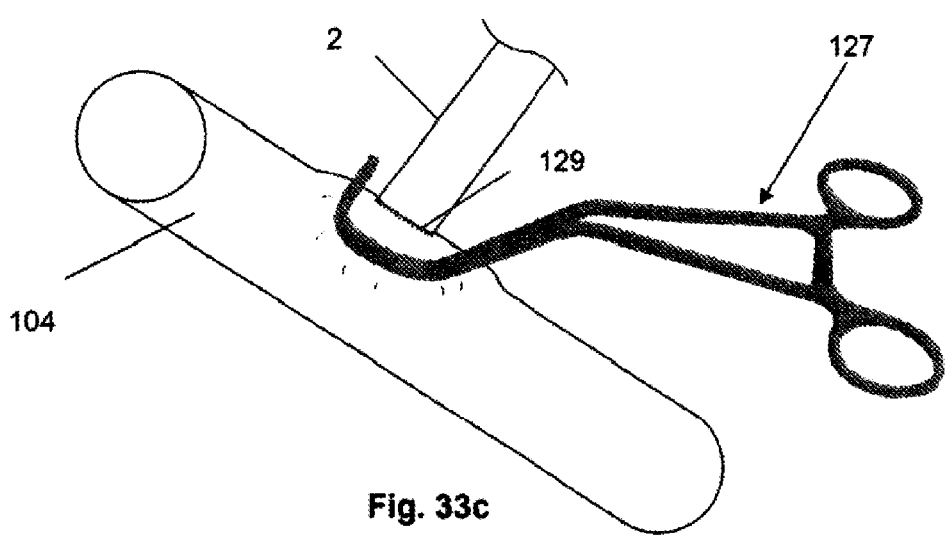

FIG. 33a illustrates the use of an aortic clamp 127 to clamp a portion of the wall of the aorta 104. This aortic clamp 127 can be a side-biting clamp of any shape, and is typically used when the vasculature (e.g., aorta 104) is still filled with blood, for example, when a heart-lung by-pass machine is not used. An aortic punch 126, or scalpel or other tool can be applied to the clamped portion of the aorta 104 to create a small opening in the vasculature or target vessel (e.g., aorta 104), as shown in FIG. 33b. FIG. 33c illustrates that the outflow conduit 2 can then be attached to the target vessel by attaching the circumferential edge of the distal end of the outflow graft/conduit around the opening with sutures (as shown), staples, clips, brads, glue, or combinations thereof.

Figure 34A:
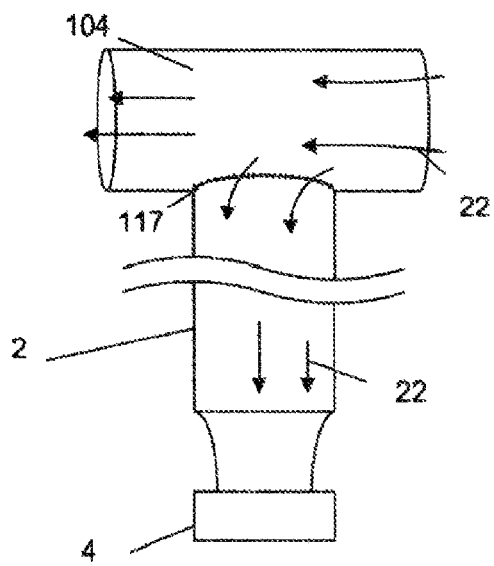
FIG. 34a illustrates blood flow through the outflow conduit after aortic anastomosis.

FIG. 34a illustrates removal of the aortic clamp 127 from the aorta 104. Once the aortic clamp 127 is removed, blood flow 130 through the aorta 104 will branch off and flow through the outflow conduit 2, as shown by arrows. If the outflow conduit 2 is not obstructed, the blood flow 130 from the aorta 104 can flow through the outflow conduit 2 and exit through the (proximal) open end of the outflow conduit 2.

Figure 34B:
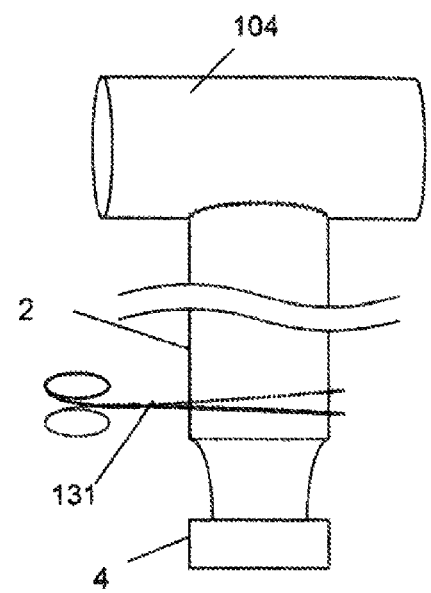
FIGS. 34b through 34d illustrate variations of methods for stanching blood flow through the outflow conduit.

FIG. 34b illustrates a variation of a method for stanching the blood flow 130 through the outflow conduit 2. A vascular clamp 131 can be placed on the outflow conduit 2 to compress the outflow conduit 2, closing and obstructing the outflow conduit 2 and stanching the flow of blood from the aorta 104 through the outflow conduit 2.

Figure 34C:
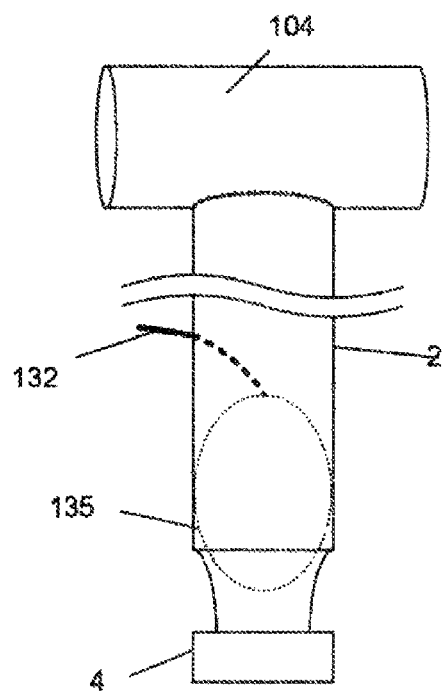

FIG. 34c illustrates another variation of a method for stanching blood flow 130 through the outflow conduit 2. An inflatable balloon 135, similar to an angioplasty balloon, can be inserted through the wall of the outflow conduit 2. The balloon 135 can be in fluid communication with a catheter 132. The balloon 135 can be inflated with a gas (e.g., carbon dioxide) or liquid (e.g., saline.) The balloon 135 can be inflated when in the outflow conduit 2, closing the outflow conduit 2 and stanching the flow of blood from the aorta 104 through the outflow conduit 2. The balloon 135 can be made of a single material along the entire surface of the balloon 135.

Figure 34D:
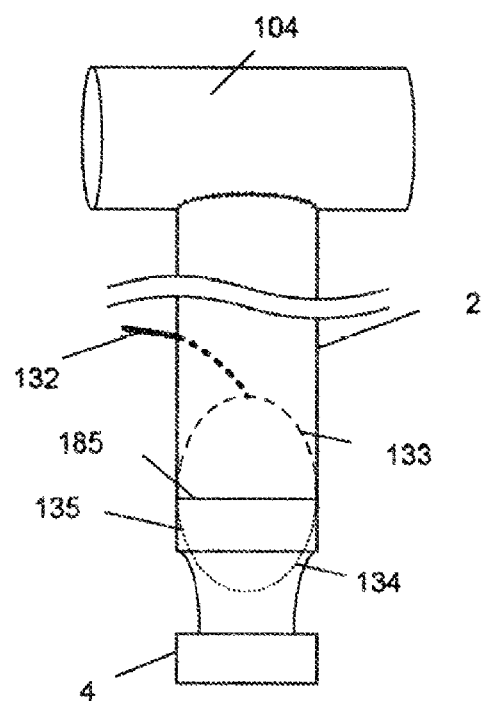

FIG. 34d illustrates yet another variation of a method for stanching blood flow 130 through the outflow conduit 2. The balloon 135 can be covered with two or more materials. In a first variation, the balloon 135 can be a composite balloon made of two sub-balloons, the first sub-balloon covered with a first material and having a first volume, and the second sub-balloon covered with the second material and having a second volume. In a second variation, the balloon 135 cave have a first volume covered by the first material and separated by a balloon septum 185 from the second volume covered in the second material. The first volume can be in fluid communication with a first channel in the catheter 132, and the second volume can be in fluid communication with a second channel in the catheter 132 or a second catheter. The first material can be on the balloon distal surface 133 and the second material can be on the balloon proximal surface 134. The first material on the balloon distal surface 133 can be gas impermeable. The second material on the balloon proximal surface 134 can be made from a material that can be gas permeable, but not liquid permeable (i.e., a breathable membrane such as PTFE or acrylic copolymer). The balloon distal surface 133 can face the aorta 104 and the balloon proximal surface 134 can face away from the aorta 104 when the balloon 135 is inserted in the outflow conduit 2 and inflated.

When de-airing the outflow conduit 2, fluid (e.g., blood and residual air) can be pumped from the pump 8 through the outflow conduit coupler 4. Air in the VAD can pass through the balloon proximal surface 134 and into the balloon 135. The balloon distal surface 133 and first volume can be inflated to obstruct the air from flowing through the vessel and force the air into the balloon proximal surface 134 while allowing the blood and/or saline to flow through the outflow conduit 2 and into the aorta 104. The air captured in the balloon 135 can be withdrawn through the catheter 132.

FIG. 35 illustrates that the outflow conduit 2 can be drawn through the tunnel, for example, positioning the outflow conduit coupler 4 near the first incision 110 or otherwise at or adjacent to the target site for the pump 8. As described above, the outflow conduit 2 can be connected to the aorta 104 (i.e., aortic anastomosis) with an aortic attachment device, such as aortic sutures 117. The aortic anastomosis can occur before or after the outflow conduit 2 is drawn into and/or through the thorax, for example, by the tunneler 177.

After the outflow conduit 2 is drawn through the thorax, the attachment ring 22 can be sutured to the heart apex 119 with an apical attachment device, such as apical sutures 113. The attachment ring 22 can be placed against, and attached to, either the left (e.g., at the apex) or right ventricles or the left or right atria. The apical sutures 113 can be the same or different suture material and size as the aortic sutures 117. The attachment ring 22 can be attached to the apex with or without the valvular structure 12 attached to the attachment ring 22.

Figure 37A:
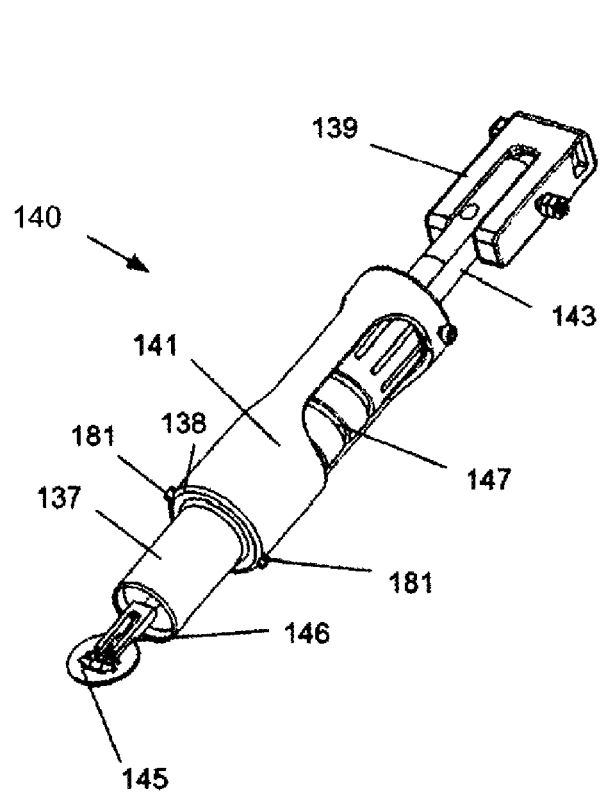
FIGS. 37a and 37b are perspective and sectional views, respectively, of a variation of the coring knife.
Figure 37B:
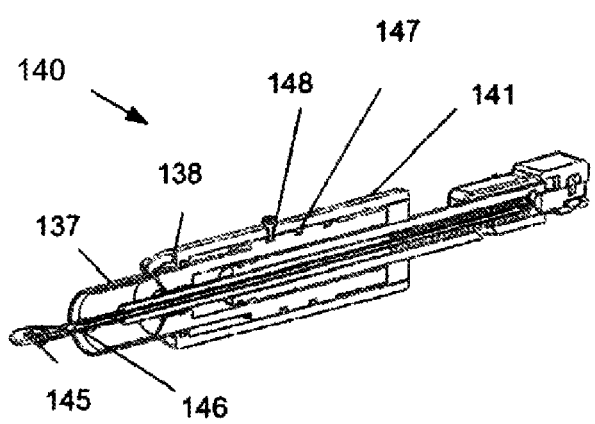
Figure 37C:
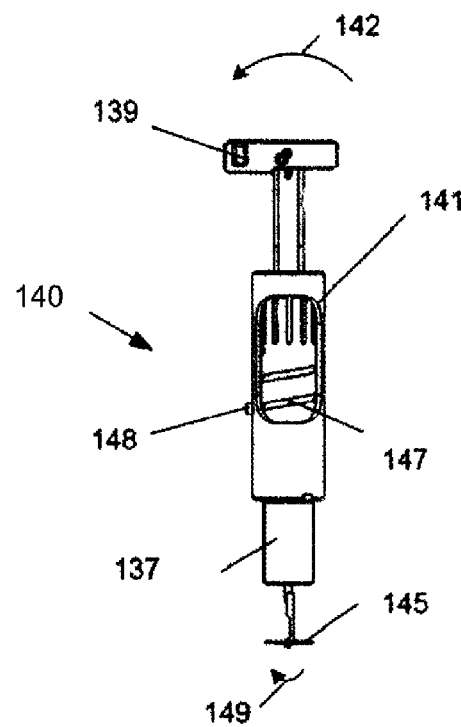
FIGS. 37c and 37d are front views of the coring knife with the coring abutment in a rotated configuration, and the coring blade in an extended configuration, respectively.
Figure 37D:
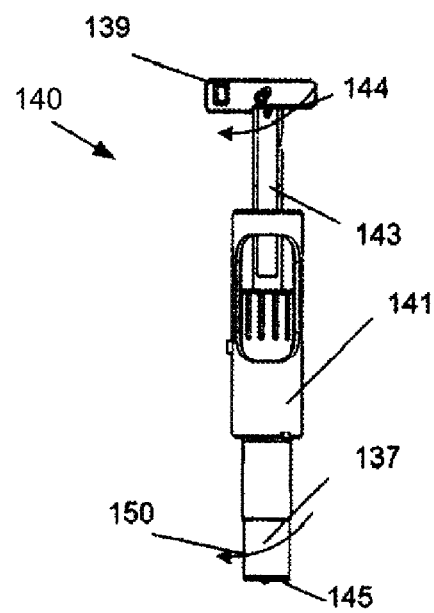
Figure 38:
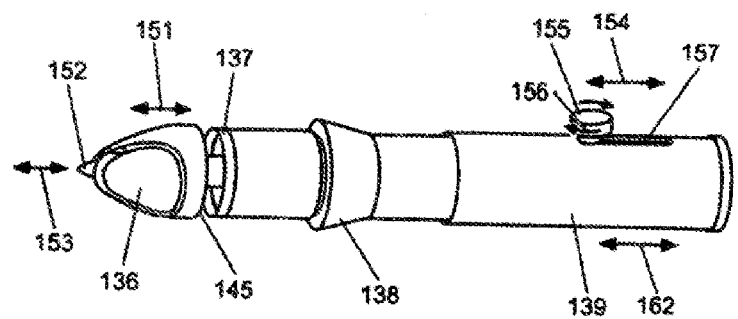
FIG. 38 illustrates a variation of the coring knife.

FIGS. 36a through 38 illustrate variations of a cutting tool, such as the coring knife 140, that can be used to core a piece of the epicardial tissue while the heart 106 is beating. FIGS. 36a through 36e illustrate a variation of the coring knife 140 with a cylindrical coring blade 137 configured to chop or shear heart tissue against an abutment surface on the proximal side of a conical knife head 136. FIGS. 37a through 37d illustrate another variation of the coring knife 140 that can have a rotatable coring abutment 145 to insert through a small slit in the heart 106 and then rotate to squeeze against and compress the heart tissue which is desired to be cored. FIG. 38 illustrates a yet another variation of the coring knife 140 that has a foreblade 152 that is independently deployable from the knife head 136.

FIGS. 36a through 36d illustrate a variation of the coring knife 140. The coring knife 140 can have a hollow cylindrical coring blade 137. The coring knife 140 can have a conical or bullet-shaped knife head 136. The knife head 136 can be shaped to push apart a pre-cut slit in epicardial tissue to introduce the knife head 136 into the left ventricle. The proximal surface of the knife head 136 can be a coring abutment 145 that the coring blade 137 can cut against.

The coring knife 140 can have a knife handle 139 at the proximal end of the coring knife 140. The knife handle 139 can be fixed to a coring control shaft 143. The coring control shaft 143 can be fixed to the knife head 136. Translation of the knife handle 139 can directly control translation of the knife head 136. The knife can have a knife stop 138 radially extending from the body of the coring knife 140. The knife stop 138 can limit the extent of the translation of the knife handle 139, and therefore the knife head 136, with respect to the coring blade 137. The knife stop 138 can prevent over insertion of the coring blade 137 into tissue. For example, in use the knife stop 138 can abut the attachment ring 22 or valvular structure housing 18 preventing or minimizing the risk of inserting the coring blade 137 through the heart wall and into the septum.

FIG. 36e illustrates that the knife handle 139 can be translated distally, as shown by arrow, to translate the knife head 136 distally (i.e., extend), as shown by arrow, away from the coring blade 137. The knife handle 139 can be translated proximally, as shown by arrow, to translate the knife head 136 proximally (i.e., retract), as shown by arrow, toward the coring blade 137. The coring abutment 145 can interference fit against the distal cutting edge of the coring blade 137. The coring abutment 145 can move within and adjacent to the coring blade 137, for example when the outer diameter of the coring abutment 145 is smaller than the inner diameter of the distal end of the coring blade 137. In this configuration, the coring abutment 145 can shear tissue against the coring blade 137.

FIGS. 37a and 37b illustrate a variation of the coring knife 140 that can have a rotatable coring abutment 145 that can be passed through a slit in the heart wall and then rotated to face the coring blade 137. The coring abutment 145 can be a circular disc. If the slit in the heart wall is not already created when the coring abutment 145 is passed through the heart wall and/or the slit is not large enough for the coring abutment 145 to pass, the circular disc of the coring abutment 145 can be used to create the slit in the heart wall. The coring abutment 145 can be rotatably attached to a control arm 146. The control arm 146 can be attached to the knife handle 139 in a configuration allowing the knife handle 139 to rotate the coring abutment 145 through manipulation of the control arm 146. The knife handle 139 can be rotatably attached to the proximal end of the coring control shaft 143.

The outside surface of the coring control shaft 143 can have a helical coring groove, for example along the length of the coring control shaft 143 that passes through the coring knife case 141. The coring knife case 141 can have a guide peg 148 that extends radially inward from the coring knife case 141. The guide peg 148 can be fixed to the coring knife case 141. The guide peg 148 can seat in the helical coring groove, controlling the movement of the coring control shaft 143 with respect to the coring knife case 141. For example, the coring blade 137 can be rotated helically with respect to the coring knife case 141.

FIG. 37c illustrates that the knife handle 139 can be rotated, as shown by arrow 142, rotating the coring abutment 145, as shown by arrow 149. The plane defined by the coring abutment 145 in a rotated configuration can be parallel to the plane defined by the cutting edge of the coring blade 137.

FIG. 37d illustrates that the knife handle 139 can be moved in a helical motion, as shown by arrow 144, helically moving the coring control shaft 143 and coring blade 137, as shown by arrow 150. The helical motion of the knife handle 139 can be constrained by the guide peg 148 slidably fitting into the helical coring guide 147. The coring blade 137 can be helically rotated and translated to abut the proximal surface of the coring abutment 145. The coring blade 137 can be rotated and translated until the coring blade 137 abuts the coring abutment 145.

FIG. 38 illustrates that the coring knife 140 can have a foreblade 152 that can be used to create a slit in the epicardial tissue through which the coring knife 140 can be inserted into the ventricle. The coring knife 140 with a rotatable coring abutment 145 can also be configured with an integral foreblade 152. The foreblade 152 can be controllably extended distally out of the distal surface of the knife head 136. The coring knife 140 can have a foreblade control knob 155 that can be used to extend and retract the foreblade 152. The foreblade control knob 155 can be fixed to the foreblade 152 by a foreblade control shaft 174, shown in FIGS. 41b through 41d. The foreblade control knob 155 can be translated proximally and distally, as shown by arrows 154, within a knob port 157 to translate the foreblade 152 proximally and distally, respectively, as shown by arrows 153, with respect to the knife head 136.

Translating the knife handle 139, as shown by arrows 162, can translate the knife head 136, as shown by arrows 151, independently of the foreblade 152. Translating the knife handle 139 can extend and retract the coring blade 137. The foreblade control knob 155 can be rotated, shown by arrows 156, to lock or unlock the translation of the foreblade 152 to the translation of the knife handle 139.

The knife head 136 can have a chisel-tipped configuration. The distal end of the knife head 136 can be traumatic or atraumatic.

Figure 39A:
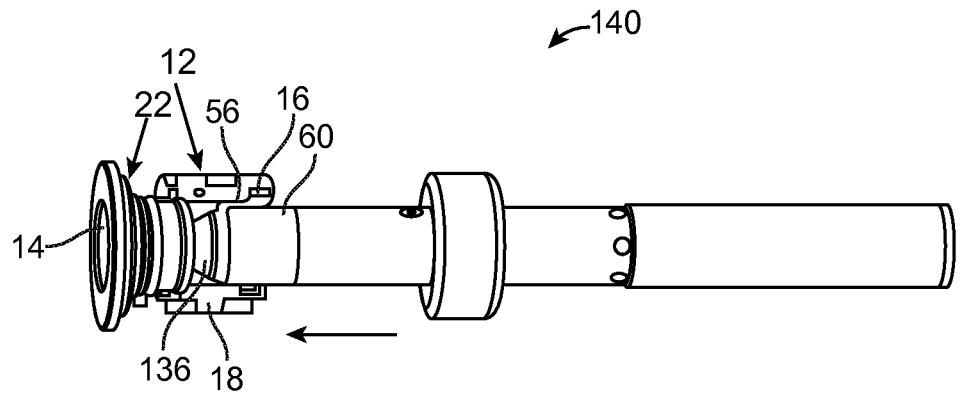
FIG. 39a is a side view with the valvular structure shown in cut-away, of a variation of a method of using the coring knife with the valvular structure.
Figure 39B:
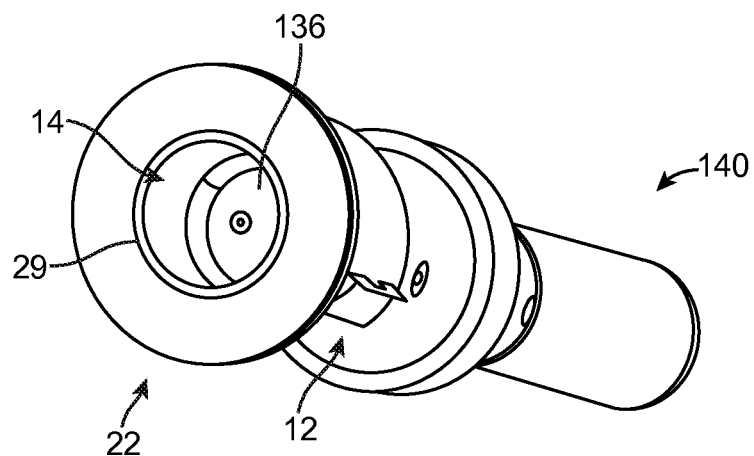

FIGS. 39a and 39b illustrate that the coring knife 140 can be inserted, as shown by arrow, through the housing 18 of the valvular structure 12 and the attachment ring 22. The leaflets 56 of the valve 16 can resiliently deform away from the coring knife 140. The leaflets 56, valve seal 60, housing seal 47, or combinations thereof, can form fluid-tight seals around the coring knife 140, for example to prevent or minimize the flow of blood from the heart 106 and out of the valvular structure 12 during use of the coring knife 140.

Figure 40A:
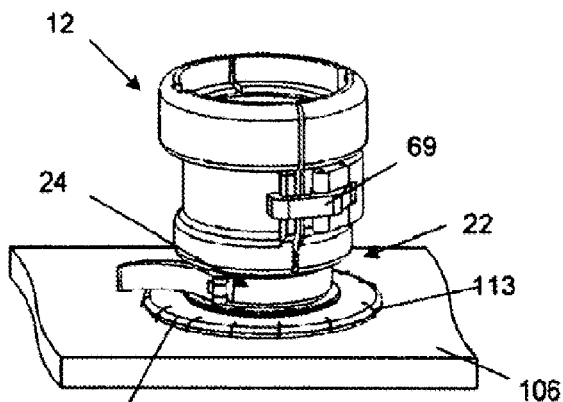
Figure 40B:
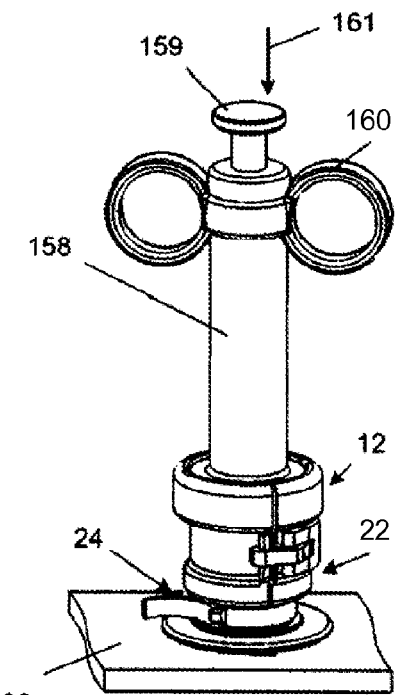
Figure 40C:
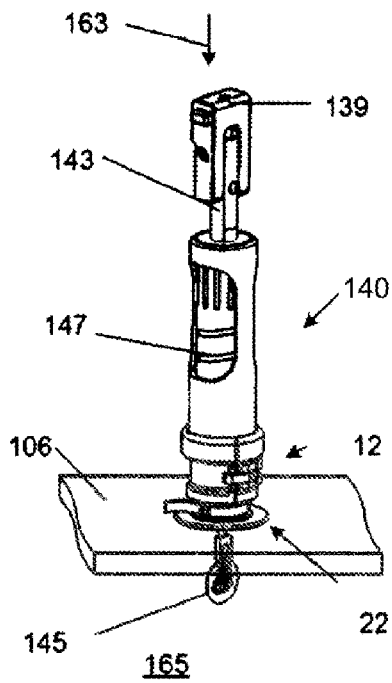

FIGS. 40a through 40i illustrate a variation of a method for coring the heart 106 and attaching the inflow conduit 10 to the heart 106 while the heart 106 is beating. FIG. 40a illustrates that the attachment ring 22 can be placed against the wall of the heart 106. One or more sutures 113 can be sewn through the cuff 35 and the heart 106, fixing the attachment ring 22 to the heart 106. The clamp 24 can be attached to the attachment ring 22 in an open configuration, as shown. The valvular structure 12 can be attached to the attachment ring 22 before or after the attachment ring 22 is attached to the heart 106. The air can be removed from the attachment ring channel 14 and/or housing channel 58 at any time by inserting blood and/or saline into the de-airing port 62 and/or by applying suction to the de-airing port 62, for example before slitting or coring an opening into the heart wall.

FIG. 40b illustrates that the initial slit in the heart wall can be made by a slitting blade. The slitting blade can be contained in a slitting blade case 158 and configured to extend from and retract into the slitting blade case 158. The slitting blade case 158 can be inserted through the valvular structure 12 and attachment ring 22. The slitting blade case 158 can have slitting blade handles 160 and a slitting blade plunger 159. The slitting blade plunger 159 can control a sharp, linear slitting blade (not shown) at the distal end of the slitting blade case 158. The slitting blade plunger 159 can be translated, as shown by arrow 161, inserting the slitting blade through the heart 106 and forming a slit in the heart 106. The valve 16 and seals in the valvular structure 12 can form a fluid-tight seal against the slitting blade case 158, preventing blood from flowing out of the heart 106 through the valvular structure 12. The slitting blade case 158 can be removed from the valvular structure 12 and the procedure site after the slit is formed. Instead of a slitting blade, the slit can be formed by a foreblade 152 extended from a coring knife 140, as shown and described in FIGS. 41a through 41d.

FIG. 40c illustrates that the coring knife 140 can be translated, as shown by arrow 163, into the valvular structure 12 and attachment ring 22. The coring knife 140 engages with the valvular structure 12 with locking tabs 181 and locking slots or coupling grooves 71 to provide a reliable connection and a depth marker and locator. The coring abutment 145 can be inserted through the slit in the heart 106 formed by the slitting blade. The coring abutment 145 can be pushed into the left ventricle 165 while the heart 106 continues to beat. The seals and valve 16 can produce a seal around the coring knife 140 preventing blood from flowing out of the beating heart 106 through the valvular structure 12.

Figure 40D:
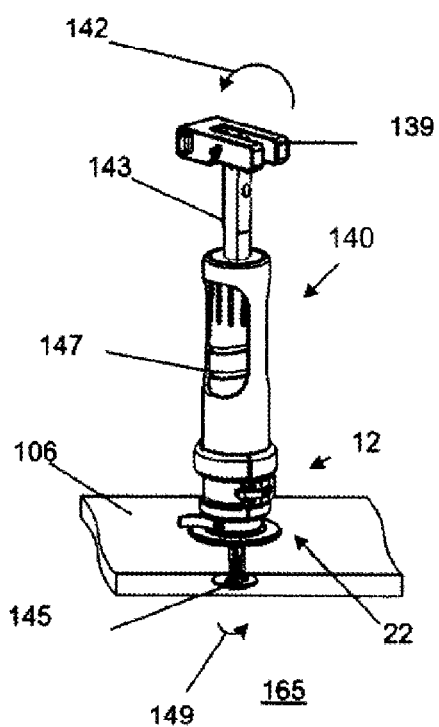

FIG. 40d illustrates that the knife handle 139 can be rotated, as shown by arrow 142, rotating the coring abutment 145, as shown by arrow 149, for example, to prepare the coring knife 140 to core a portion of the heart 106. The coring abutment 145 can be in a plane substantially parallel with, and adjacent to, the internal side of the adjacent heart wall in the left ventricle 165.

Figure 40E:
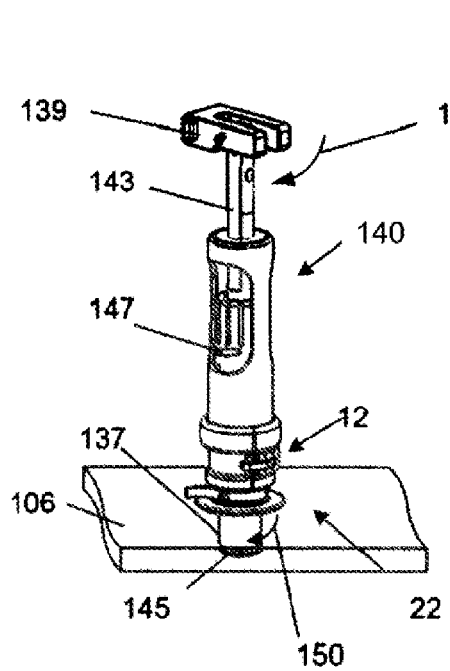

FIG. 40e illustrates twisting the coring blade 137 to cut a cylinder of the heart wall away from the rest of the heart wall. The handle can be helically moved, as shown by arrow 144, helically extending the coring blade 137, as shown by arrow 150, through the heart wall. The distal edge of the coring blade 137 can be sharpened and/or serrated and can cut the heart wall as the coring blade 137 moves through the heart wall. The coring abutment 145 can resist motion of the heart wall away from the coring blade 137, compressing the heart wall between the coring blade 137 and the coring abutment 145. The coring blade 137 can be extended until the coring blade 137 contacts the coring abutment 145, coring the heart wall. The heart wall can be cored coaxial (i.e., along substantially the same longitudinal axis) with the valvular structure 12 and/or attachment ring 22.

In an alternative variation of the coring knife 140 with the coring abutment 145 having a smaller outer diameter than the inner diameter of the cutting edge of the coring blade 137, the coring blade 137 can be extended until the coring blade 137 passes adjacent to the coring abutment 145, shearing the cored tissue 175 between the coring blade 137 and the outer circumference of the coring abutment 145.

The coring knife 140 can be withdrawn and removed from the heart 106, attachment ring 22 and valvular structure 12 with the coring blade 137 pressed against the coring abutment 145 to form a closed volume in the coring blade 137. The core of heart tissue formed by the coring blade 137 can be stored within the coring blade 137 and removed from the target site with the coring knife 140.

Figure 40F:
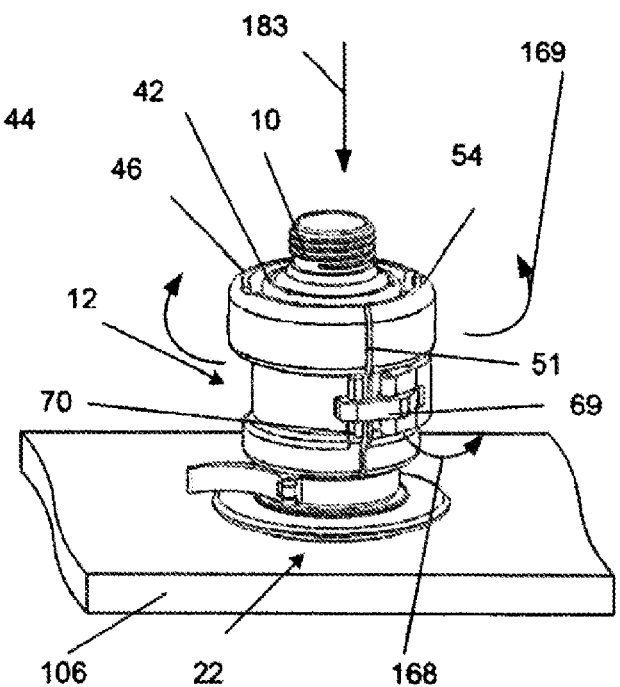

FIG. 40f illustrates that the inflow conduit 10 of the pump 8 (pump 8 not shown in FIG. 40f) can be translated, as shown by arrow 183, into the valvular structure 12 and the attachment ring 22. The inflow conduit stop 42 can abut and interference fit against the housing 18, stopping translation of the inflow conduit 10.

The valvular structure 12 and attachment ring 22 can be de-aired by applying suction to the de-airing port 62 of the valvular structure 12 and/or injecting saline or blood into the de-airing port 62. The valvular structure 12 can be de-aired once during the implantation of the ventricular assist system or multiple times throughout the implantation, for example immediately before and/or after insertion of the inflow conduit 10 through the valvular structure 12.

After the inflow port 7 of the inflow conduit 10 is located in the heart 106 and/or past a fluid tight seal formed against the attachment ring 22 (e.g., with the attachment ring seal 34) and/or the valvular structure 12 (e.g., with the housing seal 47 and/or valve 16), the valvular structure 12 can be removed from the attachment ring 22. For example, the first joint latch 69 can be opened, as shown by arrows 168. The housing first portion 46 and housing second portion 54 can then be rotated open and removed from the attachment ring 22, as shown by arrows 169.

Figure 40G:
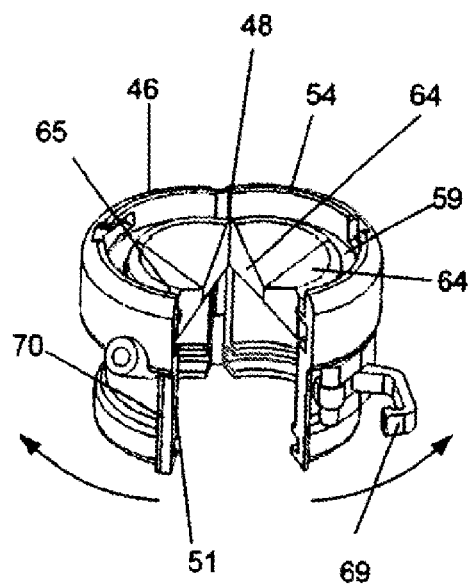
Figure 40H:
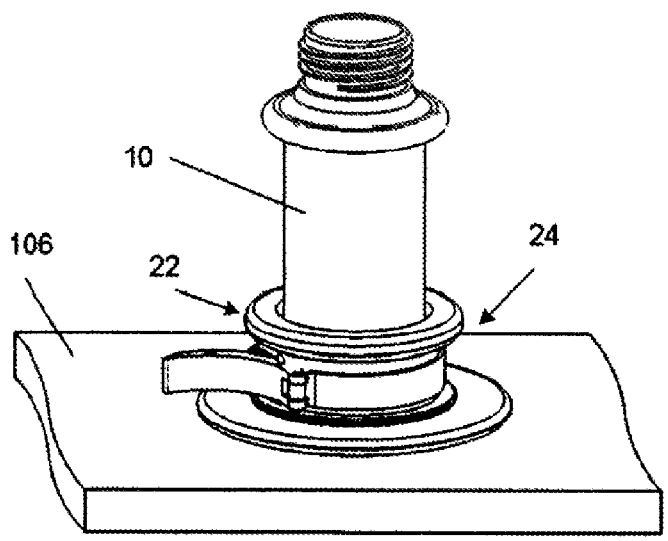

FIG. 40g illustrates the valvular structure 12 in a configuration when being opened and in the process of being removed from the inflow conduit 10. A first portion of the valvular structure 12 can be rotated away from a second portion of the valvular structure 12. For example, the interleaflet seam 64 can open at a lateral perimeter surface of the valve 16, splitting open the valve 16 along the respective housing seam 51 or 49, and the housing first portion 46 can rotate open away from the housing second portion 54 at a hinge at the housing second seam 48. When the housing 18 is removed, the valve 16 can separate from the housing 18 and remain on the inflow conduit 10. The valve 16 can then be rotated open at the end of an interleaf seam that extends to but not through the valve shoulder 59 (with the valve shoulder 59 acting as a hinge), as shown in FIG. 40g, and/or cut or torn at the interleaf seam and pulled away from the inflow conduit 10. The valve 16 can be removed with the housing 18 from the inflow conduit 10, as shown in FIG. 40g, or after the housing 18 is removed from the inflow conduit 10. FIG. 40h illustrates the inflow conduit 10 and attachment ring 22 following the removal of the valvular structure 12. The pump 8 is not shown but is attached to the distal end of the inflow conduit 10. The inflow conduit 10 can have an indicator that the pump 8 should be attached to the distal end of the inflow conduit 10.

FIG. 40i illustrates that the inflow conduit 10 can be further translated, as shown by arrows, into the left ventricle 165. The inflow conduit 10 can be translated until the inflow conduit stop 42 interference fits against the ring wall interference lip. The clamp handle 36 can then be closed, as shown by arrow 170, reducing the diameter of the clamp 24 and pressure fitting or compressing the inside of the attachment ring 22 against the outside of the inflow conduit 10, reducing or preventing translation of the inflow conduit 10 with respect to the attachment ring 22. The outside surface of the inflow conduit 10 can form a fluid-tight seal against the inside surface of the attachment ring 22 for example at the attachment ring seal 34. The inflow conduit 10 can be removed or repositioned, for example, by opening the clamp handle 36, removing or repositioning the inflow conduit 10, and then closing the clamp handle 36.

The heart 106 can pump blood during the creation of the slit, insertion of the coring abutment 145 into the ventricle, coring, insertion of the inflow conduit 10 into the heart 106, removal of the valvular structure 12, tightening of the clamp 24 around the attachment ring 22, or combinations or all of the above.

FIGS. 41a through 41d illustrate a method of coring a portion of the heart wall using a variation of the coring knife 140 similar to the variation shown in FIG. 38. FIG. 41a illustrates that the coring knife 140 can be placed adjacent to a valvular structure 12 with a diaphragm valve 16. FIG. 41b illustrates that the coring knife 140 can be inserted through the diaphragm port 83. The diaphragm port can elastically deform to accommodate the coring knife 140 passing through the diaphragm port. The diaphragm can form a fluid-tight seal around the coring knife 140 as the coring knife 140 is inserted into the diaphragm port. The foreblade 152 can be extended out of the distal end of the knife head 136 and pressed into the heart wall, as shown by arrow. The foreblade 152 can cut or slit the heart 106. The knife head 136 can be pushed into the slit or cut in the heart wall made by the foreblade 152.

FIG. 41c illustrates that the knife handle 139 can be translated toward the heart 106, extending the knife head 136 into the left ventricle 165, as shown by arrow. The coring abutment 145 can be facing the inner surface of the heart wall. The foreblade 152 can be retracted to be atraumatically covered by the knife head 136.

FIG. 41d illustrates that the knife handle 139 can be translated away from the heart 106, retracting the knife head 136 toward the coring abutment 145, as shown by arrow. The coring abutment 145 and coring blade 137 can cut tissue away from the heart wall. The coring abutment 145 and coring blade 137 can shear (if the coring abutment 145 has a smaller diameter than the diameter of the coring blade 137) or chop (if the coring abutment 145 has a diameter larger than or equal to the diameter of the coring blade 137) the tissue. Cored tissue 175 can be stored within the internal volume of the coring blade 137 until after the coring knife 140 is removed from the valvular structure 12. When the coring knife 140 is removed from the valvular structure 12, the diaphragm can close, preventing or minimizing blood flow from the heart 106 from exiting the valvular structure 12.

Figure 42B:
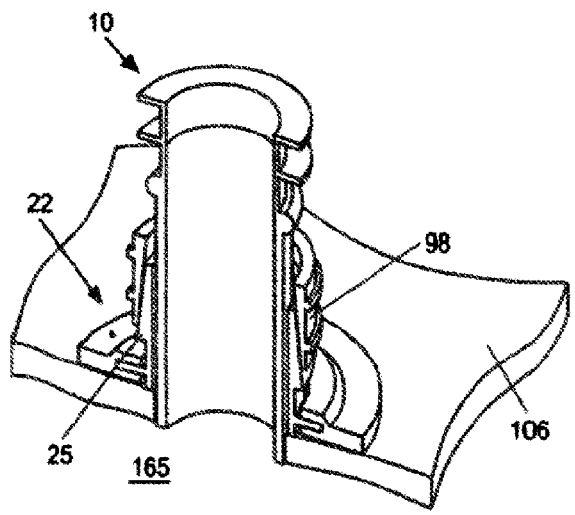
Figure 42C:
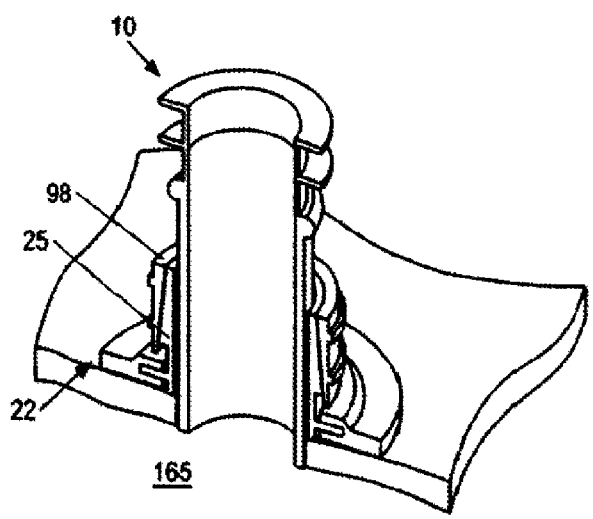

FIGS. 42a through 42c illustrate a method of using a valvular structure 12 having a locking ring 98 to clamp the attachment ring 22 to the inflow conduit 10. FIG. 42a illustrates that the inflow conduit 10 can be inserted, as shown by arrow, through the valvular structure 12 having a diaphragm valve 16 (the diaphragm can be elastically deformed out of the way of the inflow conduit 10 but is not shown for illustrative purposes). The diaphragm port 83 can elastically expand to accommodate the inflow conduit 10. The diaphragm port 83 can form a fluid-tight seal around the inflow conduit 10, preventing blood from flowing from the heart 106 out the valvular structure 12.

FIG. 42b illustrates that the tape 89 can then be removed from the valvular structure 12. The housing 18 can then be separated into the housing first portion 46 and the housing second portion 54 components and removed from the target site. The diaphragm valve 16 can then be removed, such as by being torn or cut away from the inflow conduit 10 or removed with the housing 18 when the diaphragm seam 88 opens.

FIG. 42c illustrates that the locking ring 98 can be forced toward the heart 106, as shown by arrow. In the configuration shown in FIG. 42c, the locking ring 98 can compress the ring wall 29. The inner diameter of the ring wall 29 can be reduced by the compressive pressure from the locking ring 98. The radially inner surface of the attachment ring wall 29 can compress against and press-fit to the radially outer wall of the inflow conduit 10, forming a fluid-tight seal. The locking ring 98 can be pulled away from the heart 106, relaxing and expanding the attachment ring wall 29, for example reducing the force of or completely eliminating the press fit between the radially inner surface of the attachment ring wall 29 and the radially outer surface of the inflow conduit 10.

Figure 43A:
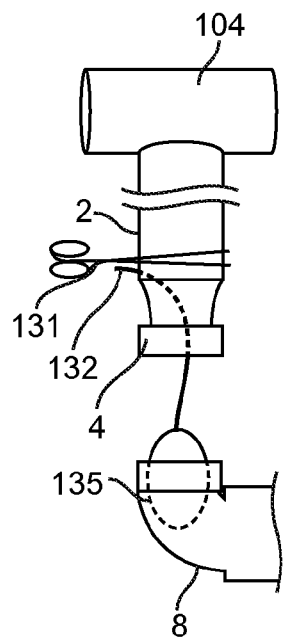
FIGS. 43a and 43b illustrate a variation of a method for stanching blood flow through the pump outflow elbow and de-airing the pump.
Figure 43B:
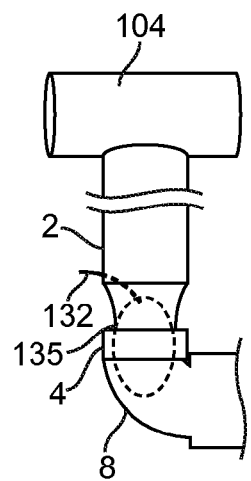

FIGS. 43a and 43b illustrate a variation of a method for de-airing the outflow conduit 2. FIG. 43a illustrates that when the blood flow in the outflow conduit 2 is stanched by a clamp 131 (as shown) or balloon 135, a balloon catheter 132 can be inserted through the wall of the outflow conduit 2. The pump 8 can be de-aired, for example the pump 8 can be run when in fluid communication with the ventricle, or the pump 8 can be pre-loaded with saline or blood. The balloon 135 can then be inserted into the terminal outflow end of the pump 8 and inflated, for example maintaining the pump 8 and inflow conduit 10 in a de-aired condition (i.e., with no air within the fluid channel of the pump 8 or the inflow conduit 10).

FIG. 43b illustrates that the outflow conduit 2 can be joined to the pump 8 at the outflow conduit coupler 4. The clamp 131 can be removed from the outflow conduit 2 before coupling the outflow conduit 2 to the pump 8, allowing blood from the aorta 104 to de-air the outflow conduit 2 and then the outflow conduit 2 can be joined to the pump 8.

Alternatively, the outflow conduit clamp 131 can remain on the outflow conduit 2 after the outflow conduit 2 is joined to the pump 8. The balloon 135 can then be removed from the pump 8 and outflow conduit 2, and the pump 8 can be run. The air from the outflow conduit 2 between the outflow conduit clamp 131 and the pump 8 can be forced out through the hole in the side wall of the outflow conduit 2 directly or drawn out via a needle inserted into the outflow conduit 2. If a balloon catheter with side ports is used, the catheter ports can be used to withdraw air instead of using the hole in the graft or an additional needle.

Once the outflow conduit 2 and the remainder of the system is de-aired, the balloon 135 (as shown) and/or outflow conduit clamp 131 can be removed from the outflow conduit 2. If a catheter 132 was removed from the wall of the outflow conduit 2, a suture can be sewn if needed, such as by a purse stitch, into the outflow conduit 2 to close the hole in the outflow conduit wall.

Alternatively, when the outflow conduit 2 is occluded by the balloon 135 or clamp 131, the pump 8 can be attached to the outflow conduit 2 and operated. Excess air in the ventricular assist system can be withdrawn with a catheter 132 or the bi-material balloon described herein.

Figure 44:
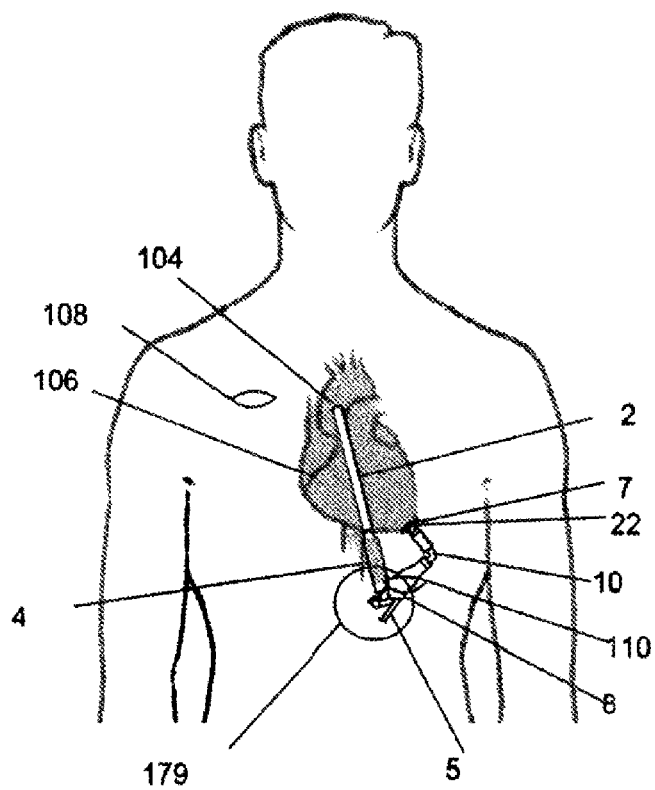
FIG. 44 illustrates a variation of a method for de-airing the ventricular assist device.

FIG. 44 illustrates another variation of a method for de-airing the system using a liquid-filled de-airing bladder, enclosure or pouch to prevent air from entering the VAD components during assembly of the outflow conduit 2 and the pump 8. The outflow conduit coupler 4, outflow end of the pump 8 and the end of the outflow conduit 2 to be attached to the pump 8 can be placed in the de-airing pouch 179. The de-airing pouch 179 can be filled with saline before or after placing the VAD components in the de-airing pouch 179. The attachment ring 22 can be previously de-aired through the de-airing port 62 on the valvular structure 12. The outflow conduit 2 can be previously de-aired with blood flow from the aorta 104 and stanching, for example, with an outflow conduit clamp 131 or balloon 135. The pump 8 and inflow conduit 10 can be pre-filled with saline or blood before delivery into the target site. The outflow port of the pump 8 can be plugged before the pump 8 is delivered into the target site.

Figure 45:
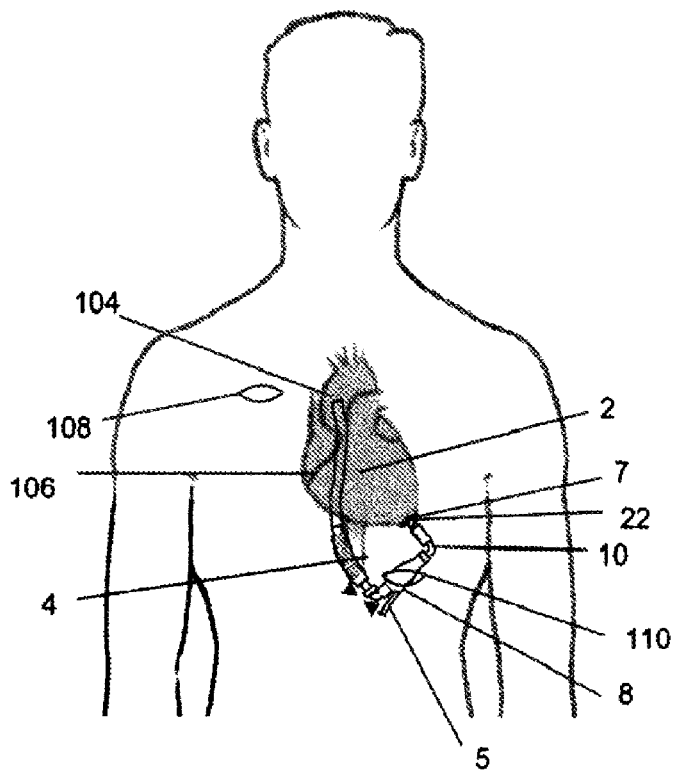
FIG. 45 illustrates a variation of attaching the pump to the outflow conduit.

When the outflow end of the pump 8 and the inflow end of the conduit are located in the de-airing pouch 179, the balloon 135 in the outflow conduit 2 can be deflated and removed or the outflow conduit clamp 131 on the outflow conduit 2 can be removed. The blood flowing from the aorta 104 can de-air the outflow conduit 2, purging air in the outflow conduit 2 into the de-airing pouch 179. The purged air can then escape from the de-airing pouch 179 or travel to a portion of the de-airing pouch 179 away from the openings of the VAD components. The pump 8 can be driven to pump blood through the inflow conduit 10 and pump 8 to drain any additional air from the pump 8 and inflow conduit 10. The outflow conduit 2 can then be attached to the pump 8 in the de-airing pouch 179 or without a de-airing pouch 179, as shown in FIG. 43b or 45.

The percutaneous lead 5 can be attached to the pump 8 and to external power, control and data transmission devices as known in the art.

The system can be implanted when the heart 106 is beating and the patient is not on cardio-pulmonary bypass. However, the system can be implanted with the patent on cardio-pulmonary bypass and the heart 106 slowed or stopped. The system can be implanted using less invasive techniques described herein, but can be implanted with a full thoracotomy and sternotomy.

In FIGS. 46a and 46b, another embodiment of attachment ring 22 is formed by injection molding a polymer in a mold containing reinforcement elements which are to be imbedded or encased within the polymer. The mold cavity includes geometric features that simultaneously form interface lip 25, cylindrical ring wall 29 which forms a tubular fluid passageway, distal band 31, and ring seal 34 as a single, unitary structure. Ring seal 34 forms the circular, inner edge of the proximal opening to ring channel 14.

Attachment ring 22 is flexible. The polymer used for molding can be silicone rubber, although other polymers suitable for implantation may be used. When completely cooled and/or cured after molding, the polymer is flexible and elastic to allow ring seal 34 to flex, conform, and seal against a cylindrical object that is inserted through ring channel 14. The reinforcement elements include proximal reinforcement band 202, distal reinforcement band 204, and fiber mesh 206. Proximal and distal reinforcement bands 202, 204 can be made of a material that is more rigid than the polymer injected into the mold and which forms the remainder of attachment ring 22. The additional rigidity provided proximal and distal reinforcement bands 202, 204 help openings at the opposite ends of ring channel 14 maintain a circular shape. Proximal and distal reinforcement bands 202, 204 can be made of Nylon, acetal, polycarbonate, HDPE, PP, PET, PEEK, titanium or stainless steel. Fiber mesh 206 can be made of polyester fibers that have been braided to form a mesh tube which is then placed in the mold as part of the molding process. Other types of fibers and mesh configurations can be used. Fiber mesh 206 can be distributed within distal band 31 and ring wall 29. Fiber mesh 206 helps prevent the polymer from tearing due to mechanical stress, such as may be arise from sutures used later to attach cuff 35 to distal band 31. Flared ends of fiber mesh 206 provide positive fixation of sutures to the polymer substrate of distal band 31.

Attachment ring 22 can be rotationally symmetric about longitudinal axis 200, so that interface lip 25, ring wall 29, distal band 31, ring seal 34, proximal reinforcement band 200, and distal reinforcement band 202 are each annular in shape.

After molding, cuff 35 can be attached to distal band 31 by passing a needle with suture 208 through cuff 35 and distal band 31. Suture 208 can be a continuous, non-bioerodable fiber or thread that is looped in a helical manner through the outer perimeter of distal band 31. Opposite ends of suture 208 can be tied in a knot 208a to prevent loosening. Portion 29a of ring wall 29 extends distally beyond distal band 31. Portion 29a helps to center the hole in cuff 35 with ring channel 14 so that no portion of cuff 35 obstructs ring channel 14. In subsequent clinical use of attachment ring 22, cuff 35 is attached to a patient's heart and ring clamp 24 can be used to secure inflow conduit 10 within ring channel 14.

The molding process allows ring seal 34 to be formed, in a consistent manner, with a diameter and round shape that corresponds to the size of inflow conduit 10, so that a fluid-tight seal between attachment ring 22 and exterior surfaces of inflow conduit 10 results when inflow conduit 10 is disposed within attachment ring 22

Figure 47A:
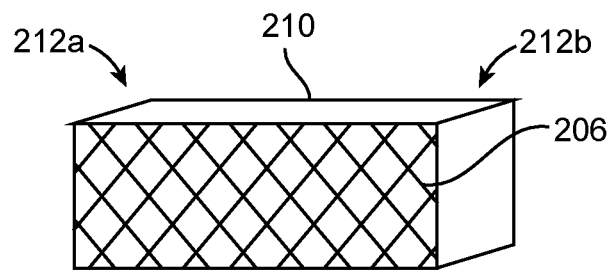
FIGS. 47a-47c show an attachment ring, FIG. 47a showing a flat sheet of material used for making the attachment ring.
Figure 47B:
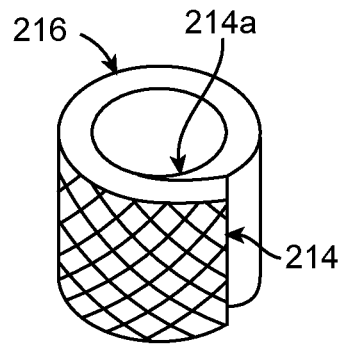
Figure 47C:
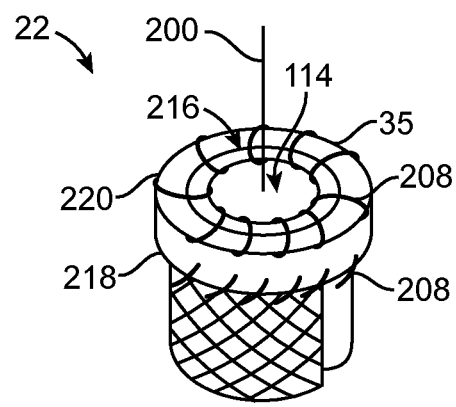

In FIGS. 47a-47c, another embodiment of attachment ring 22 is formed by molding a polymer into a sheet in which fiber mesh 206 is embedded or encased. Suitable materials for the polymer and fiber mesh can be as described for FIGS. 46a-46d. As shown in FIGS. 47a and 47b, attachment ring 22 can be made by cutting out a rectangular strip 210 from the flat sheet, rolling strip 210 so that opposite ends 212 of the strip overlap, and bonding ends 212 together to form a fluid-tight seam 214.

Next, cuff 35 can be attached around distal portion 216 of the rolled strip by passing a needle with suture 208 through cuff 35 and distal portion 216. A single, continuous piece or several pieces of suture 208 can be used to secure proximal edge 218 and distal edge 220 of cuff 35 to distal portion 216 of the rolled strip. In subsequent clinical use of attachment ring 22, cuff 35 is attached to a patient's heart and ring clamp 24 can be used to secure inflow conduit 10 within ring channel 14. Interior edge 214a of seam 214 extends through the entire length of ring channel 14. End 212a of the strip which forms interior edge 214a can be tapered in cross-section so as to form a smooth interface with opposite end 212b. Material can also be added at interior edge 214a to form the smooth interface. The smooth interface allows the inner surface of ring channel 14 to form a fluid-tight seal against inflow conduit 10.

Figure 48A:
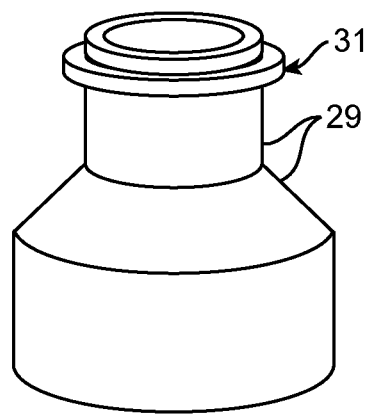
FIGS. 48a-48d show an embodiment an attachment ring with an integral valve.
Figure 48B:
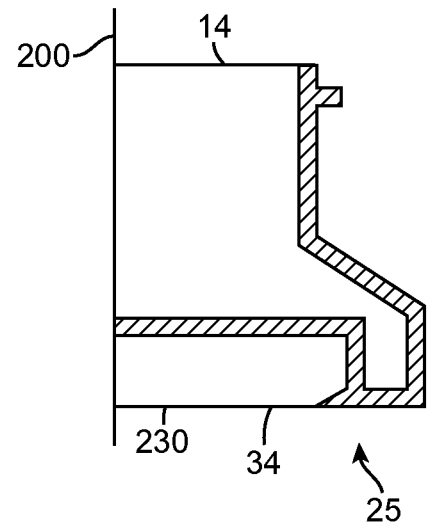
Figure 48C:
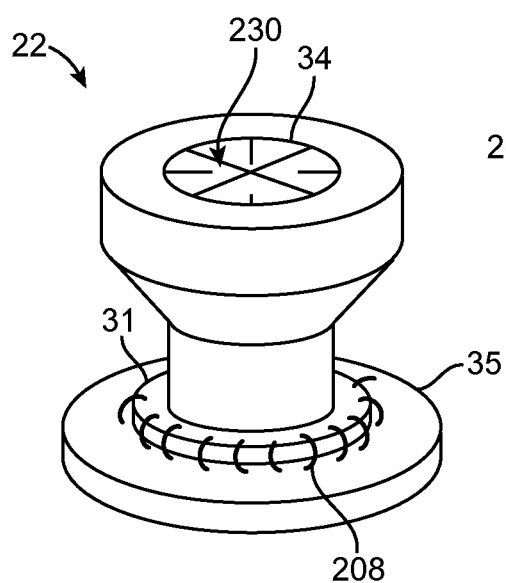
Figure 48D:
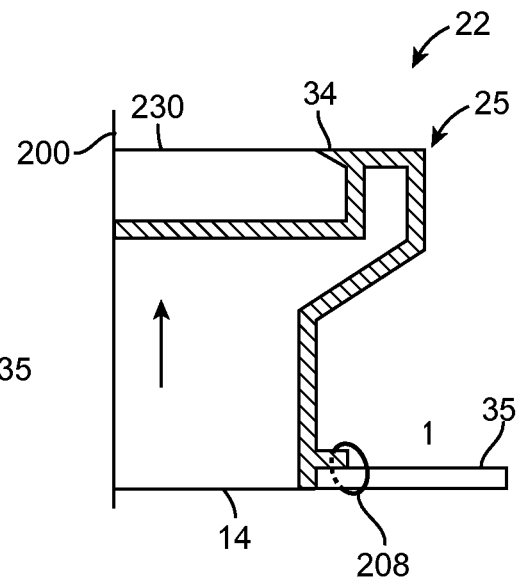

In FIGS. 48a and 48d, another embodiment of attachment ring 22 is formed by injection molding a polymer in a mold cavity having geometric features that simultaneously form ring wall 29, distal band 31, ring seal 34, and ring valve 230 as a single, unitary structure. Suitable materials for the polymer can be as described for FIGS. 46a-46d. FIGS. 48a and 48c show views of the distal end and proximal end, respectively. FIGS. 48a and 48b show attachment ring 22 without cuff to better show features of distal band 31.

Attachment ring 22 can be rotationally symmetric about longitudinal axis 200, so ring wall 29, distal band 31, and ring seal 34 are each annular in shape. In the illustrated embodiment, ring valve 230 is a quadcuspid (i.e., four-leaflet) valve similar in configuration to valve 16 described in connection with FIGS. 12a and 15c. Other configurations for valve 230 can be implemented, for example and without limitation a tricuspid valve (similar to FIG. 14a), a bicuspid valve (similar to FIG. 15a), a dome valve, a diaphragm valve (similar to FIG. 15f), and combinations thereof. Ring seal 34 forms the circular, inner edge of the proximal opening of ring channel 14. When a cylindrical object (for example, slitting tool 300 and coring knife 140) is inserted into the proximal opening of ring channel 14, ring seal 34 seals against the cylindrical object and ring valve 230 flexes open. When the cylindrical object is removed, ring valve 230 closes autonomously to reduce, prevent or inhibit fluid from flowing distally through ring valve 230 in the direction of arrow 231. With attachment ring 22 attached to the heart, ring valve 230 can allow slitting and coring of heart tissue while the heart is beating and pumping without the use of valvular structure 12.

After molding, cuff 35 can be attached to distal band 31 by passing a needle with suture 208 through cuff 35 and distal band 31, such as described for FIGS. 46c and 46d. In subsequent clinical use of attachment ring 22, cuff 35 is attached to a patient's heart and ring clamp 24 can be used to secure inflow conduit 10 within ring channel 14.

Figure 52A:
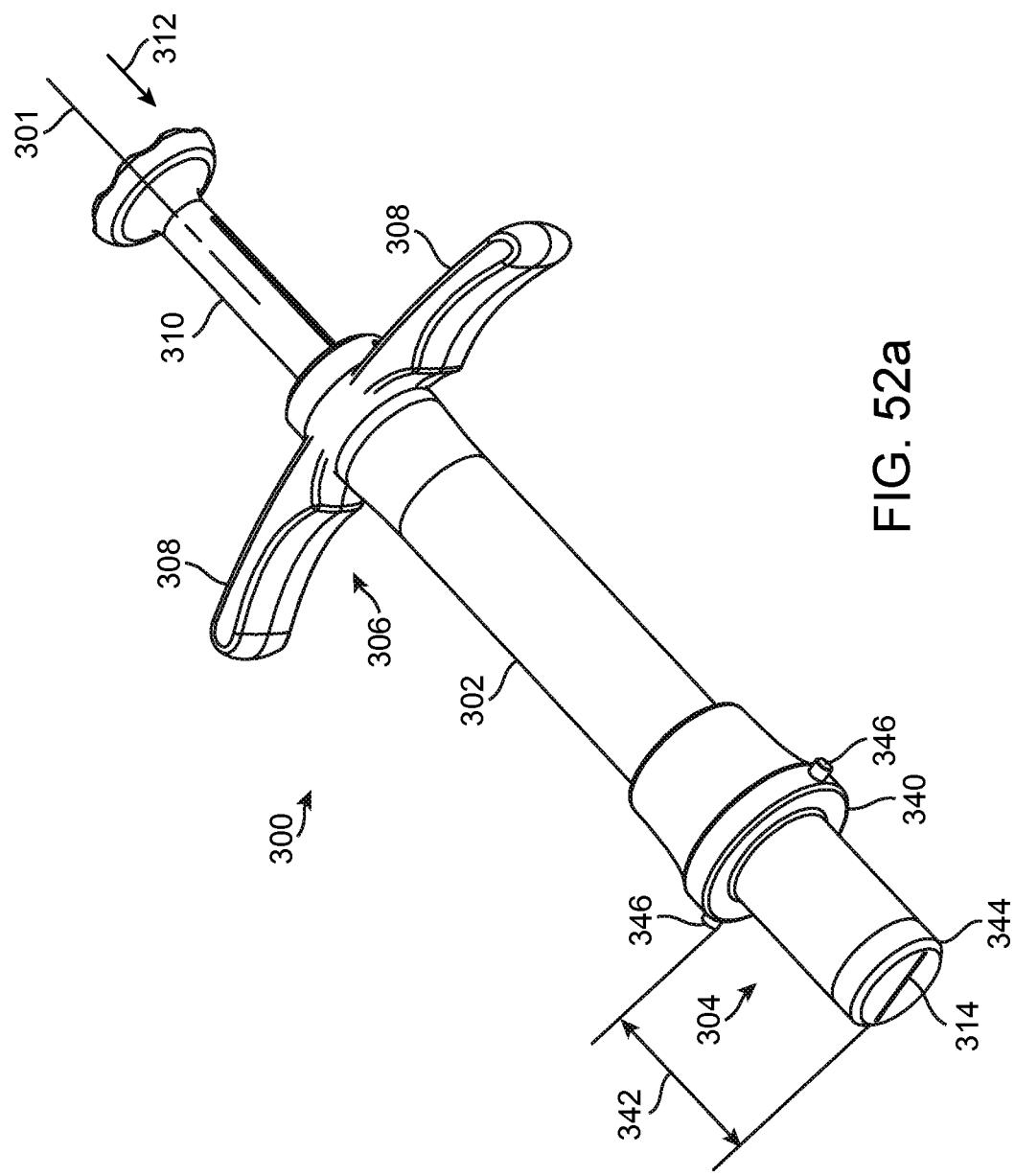
FIGS. 52a-52c are perspective and cross-sectional views of a slitting tool for making a linear incision in the heart, the linear incision allow for a subsequent circular incision.
Figure 52B:
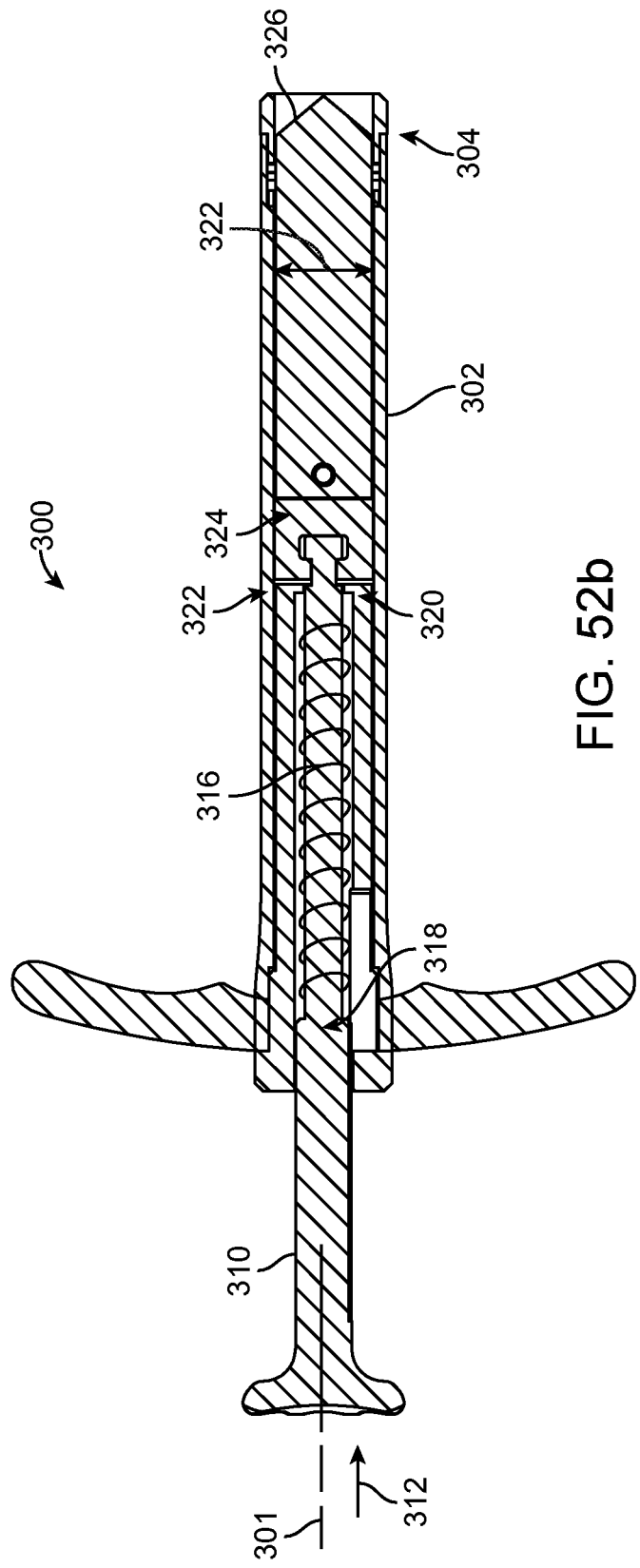
Figure 52C:
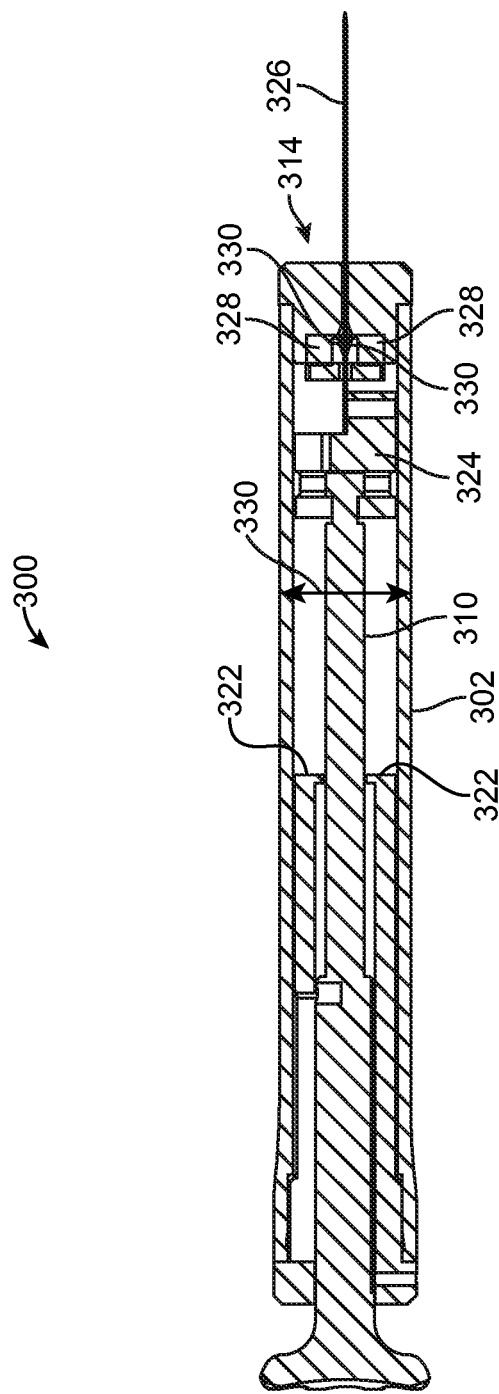

Attachment ring 22, in any of the embodiments described above, may include an alignment feature that allows a slitting tool and coring knife 140 to share common alignment. A slitting tool is shown in FIGS. 52a-52c. In use, the slitting tool can be inserted into attachment ring 22. When inserting the slitting tool into attachment ring 22, the alignment feature ensures that the flat blade of the slitting tool is oriented in a particular way, as will be described in more detail below. Once aligned, the flat blade extends to form a slit in the heart tissue, then the slitting tool is removed from attachment ring 22. The slit functions as a passage through which elements of coring knife 140 can be inserted. When inserting coring knife 140 into attachment ring 22, the alignment feature ensures that rotatable coring abutment 145, such as shown in FIGS. 37a-37d, is oriented along the same line as the slit previously formed by the slitting tool and thereby allows of easy entry of coring abutment 145 into the heart cavity.

Alignment feature can take the form of a structural feature, such as two indentations 230 (FIG. 4a) formed into interface lip 25 at the proximal end of attachment ring 22. Indentations 230 can be shaped and sized to receive protrusions 346 on the exterior surface of the slitting tool (see FIG. 52a) and protrusions 411 on the exterior surface of the coring knife (see FIG. 54). Indentations 230 allow for "blind" alignment whereby engagement of indentations and protrusions provide tactile feedback to the surgeon or other user which indicates proper alignment. Alignment feature can also take the form of a visual indicator, such as indelible markings 232 (FIG. 46c) in a contrasting color and/or an embossed marking applied on interface lip 25. In use, a pair of protrusions or markings on the exterior surface of the slitting tool can be aligned with markings 232 during insertion of the slitting tool into attachment ring 22. Subsequently, a pair of protrusions or markings on the exterior surface of coring knife 140 can be aligned with markings 232 during insertion of coring knife 140 into attachment ring 22.

Referring again back to FIG. 7a, clamp 24 can be disposed around the central portion of attachment ring wall 29 located between interface lip 25 and cuff 35. Clamp 24 can be installed and removed from attachment ring 25 by translating it axially, in a direction along longitudinal axis 200, onto attachment ring 22 until it reaches the central portion of attachment ring wall 29. However, in cases where clamp 24 has limited ability enlarge its clamp diameter 38, interface lip 25 and cuff 35 could interfere with axial translation of attachment ring 22, making installation and removal of attachment ring 22 difficult especially after attachment ring 22 has been secured to heart tissue.

In FIGS. 49a-49d, another embodiment of clamp 24 is shown having multiple linkages that allow clamp 24 to be easily installed and removed from attachment ring 22, either before or after attachment ring 22 has been secured to heart tissue. The linkages are in the form of first curved piece 240, second curved piece 242, lever 244, and third curved piece 246. When clamp 24 is closed (FIG. 49a), inner surfaces of first, second and third curved pieces 240, 242, 246 form a circle having diameter 247 needed to allow the curved pieces to apply pressure to attachment ring wall 29 in order to secure inflow conduit 10 to attachment ring 22. Diameter 247 can be about the same as or slightly smaller (for example, 5%, 10%, or 20% smaller) than the outer diameter of attachment ring wall 29. The linkages can be pivoted relative to each other so as to create an opening that is larger that the outer diameter of attachment ring wall 29. With this ability, attachment ring 22 can be installed and removed from attachment ring 22 in a manner that avoids interference from interface lip 25 and cuff 35.

Figure 49A:
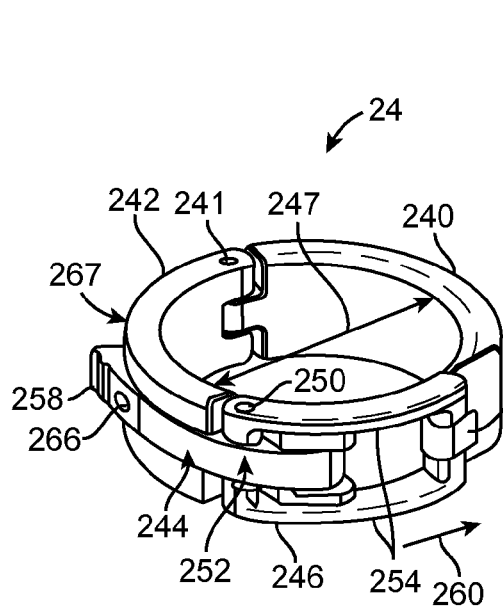
FIGS. 49a-49d are perspective views of a clamp for use on an attachment ring, FIG. 49d showing clamp closed on an attachment ring.
Figure 49B:
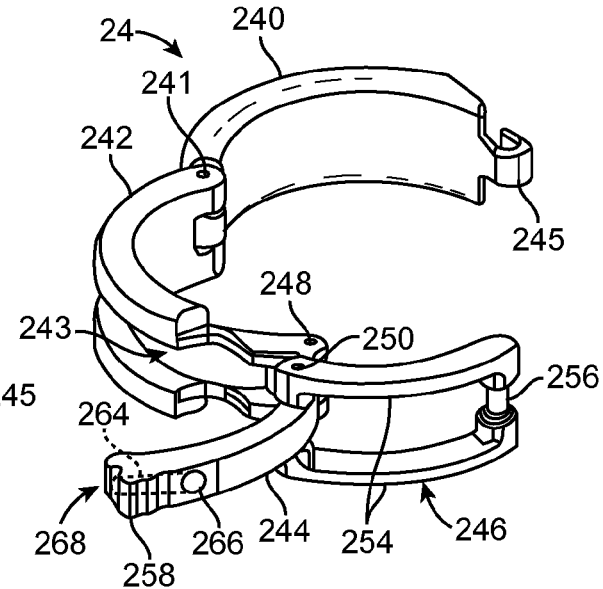

Referring to FIG. 49b, the ends of first curved piece 240 and second curved piece 242 are pivotally connected to each other by primary hinge 241. The opposite end of first curved piece 240 has hook 245. The opposite end of second curved piece 242 is connected to lever 244 by first lever hinge 248. Second lever hinge 250 connects medial part 252 of lever 244 to one end of third curved piece 246. Medial part 252 is disposed between two legs 254 of third curved piece 246. The opposite end of curved piece 246 has cylindrical catch 256. Cylindrical catch 256 connects legs 254 together and is sized and shaped to fit within hook 245.

FIG. 49a shows clamp 24 when closed. Lever 244 is disposed within groove 243 (FIG. 49b) formed within second curved piece 242 and between legs 254 of third curved piece 246. Cylindrical catch 256 is seated within hook 245. First lever hinge 248 is positioned adjacent hook 245.

When clamp 24 is closed, movement of third curve piece 246 along the direction of arrow 260 is prevented by the presence of attachment ring wall 29 and inflow conduit 10 within clamp 24. That is, attachment ring wall 29 and inflow conduit 10 prevent inner diameter 247 of clamp 24 from getting smaller.

Figure 49C:
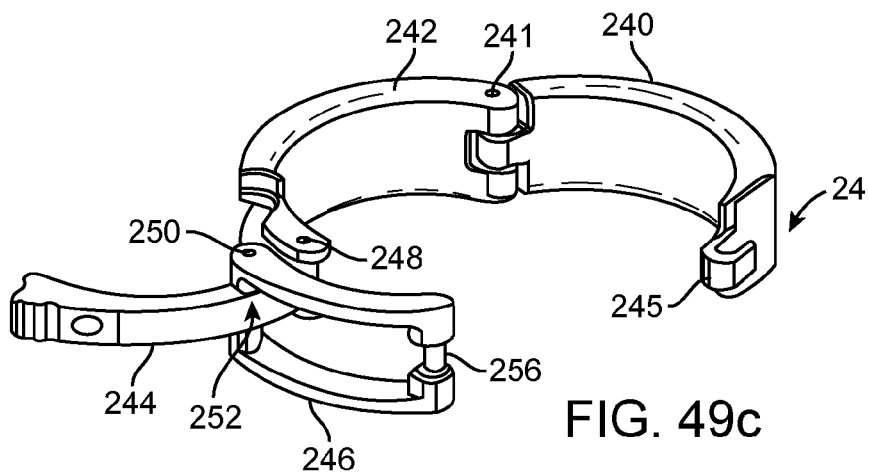
Figure 49D:
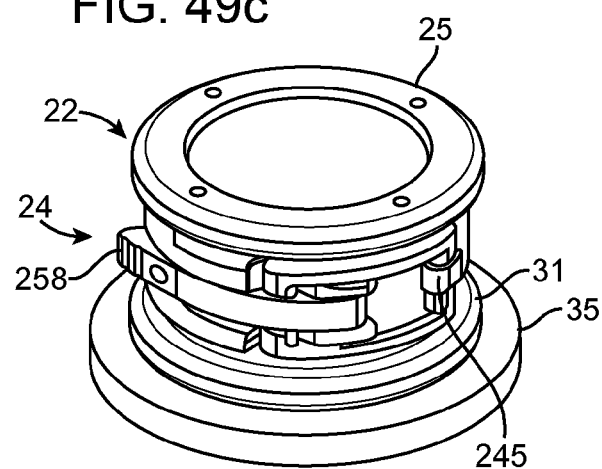

To open clamp 24, a person can pull protrusion 258 at the free end of lever 244 radially outward in the direction of arrow 262, as shown in FIG. 49b. Movement of protrusion 258 along arrow 260 causes cylindrical catch 256 to move along arrow 260, without requiring inner diameter 247 to get smaller. Thus, the presence of attachment ring wall 29 and inflow conduit 10 within clamp 24 does not prevent cylindrical catch 256 from disengaging hook 245 when protrusion 258 is pulled along arrow 260. Once disengaged first curve piece 240 can be pivoted about primary hinge 241 to create an opening that is substantially larger than diameter 247, as shown in FIG. 49c.

Clamp 24 can have a provision for locking lever 244 in the closed position. Through hole 264 is formed through the free end of lever 244. When in the closed position, as shown in FIG. 49a, first opening 266 of the through hole is exposed and second opening 268 (FIG. 49b) is disposed within groove 243 in second curved piece 242. Second opening 268 faces the opening of through hole 267 in second curved piece 242 which extends to the outer surface of second curved piece 242. Through hole 264 and through hole 267 can be aligned so as to be coaxial, which allows a suture to be looped through both through holes. The suture prevents lever 244 from moving out in direction of arrow 262 and thereby keeps clamp 24 closed. Opposite ends of the suture can be tied together in a knot to keep the suture in place. The suture can be cut to allow its removal and to allow clamp 24 to be opened.

In FIGS. 50a and 50b, another embodiment of clamp 24 is shown having a single, unitary structure in the form of ring 270 with detachable ends. The ends have ratchet features that interlock with each other and allow inner diameter 272 of ring 270 to become smaller. First end 274 includes guard member 276 and ratchet member 278 with a plurality of radially inward facing teeth 280. Second end 282 includes ratchet member 284 with a plurality of radially outward facing teeth 286. Ratchet member 284 is disposed within an open channel between guard member 276 and ratchet member 278. When clamp 24 is open, as shown in FIGS. 50a and 50b, gap 280 exists between the free end of ratchet member 284 and the end of the open channel between guard member 276 and ratchet member 278. Gap 280 allows first end 274 and second end 282 to pushed together, which causes teeth 280 and teeth 286 to engage each other. Teeth 280 and teeth 286 are configured to slip past each other when first end 274 and second end 282 are pushed together and are configured to engage each other to prevent first end 274 and second end 282 from subsequently moving apart from each other. In use, clamp 24 can be disposed around attachment ring wall 29 of attachment ring 22. Guard member 276 prevents attachment ring wall 29 from being pinched within gap 280.

Ring 270 functions like a spring in that it stores spring energy when first end 274 and second end 282 are pushed together. Ring 270 can be formed by injecting a polymer into a mold cavity that includes geometric features that simultaneously form guard member 276, ratchet member 278, teeth 280, ratchet member 284, and teeth 286 as a single, unitary structure. Through hole 288 is formed in first end 274. Through hole 290 is formed in second end 282. Through hole 288 and through hole 290 can receive tips of a tool for pushing first end 274 and second end 282 together. Through hole 300 is formed in ratchet member 278. Opposing teeth 280, 286 can be disengaged from each other by inserting a tool in through hole 300 and pulling radially outward. When opposing teeth 280, 286 disengage, first end 274 and second end 282 autonomously move apart from each other due to the spring energy stored in ring 270.

After pushing first end 274 and second end 282 together, a suture can be looped into through hole 300 and through hole 290 as a security measure to prevent the ratchet members from inadvertently disengaging. Opposite ends of the suture can be tied together in a knot to keep the suture in place. The suture can be cut to allow its removal and to allow ratchet members to disengage and inner diameter 272 to enlarge.

When clamp 24 is open, as shown in FIGS. 50a and 50b, inner diameter 272 is larger than the outer diameter of attachment ring wall 29 of attachment ring 22. When clamp 24 is closed by pushing the first end 274 and second end 282 together, inner diameter 272 corresponds to the size of inflow conduit 10 plus the thickness of attachment ring wall 29, so that a fluid-tight seal between attachment ring 22 and exterior surfaces of inflow conduit 10 results when inflow conduit 10 is disposed within attachment ring 22.

In FIG. 51, another embodiment of clamp 24 is shown having ratchet members 278, 284, each with only one tooth 286, 280. Other embodiments may have any number of teeth, as may be needed, to provide additional engagement and/or to allow clamp 24 to be used with attachment rings 22 and inflow conduits 10 of different sizes.

After attachment ring 22 is attached to heart apex 119, foreblade 152 of coring knife 140 of FIG. 38 can be used to form a slit through the epicardium and into the myocardium at heart apex 119. Alternatively, slitting tool 300 of FIGS. 52a-52c can be used to form the slit into the heart.

As shown in FIG. 52a, cylindrical housing 302 has front end 304 and rear end 306. Rear end 306 includes radially protruding handles 308. Spring-loaded actuator 310 protrudes axially out of rear end 306 and is connected to a flat blade contained within housing 302. Pushing actuator 310 axially forward in the direction of arrow 312 causes the flat blade to extend out of slit opening 314 at front end 304.

As shown in FIG. 52b, spring 316 is contained within a rear segment of housing 302. Rear end 318 of spring 316 is attached to a medial segment of actuator 310. Forward end 320 of spring 316 abuts wall 322 within housing 302. Spring 316 and flat blade 326 are contained within housing 302 at opposite sides of wall 322. Spring 316 is under compression and keeps the flat blade completely retracted within housing 302 until a user pushes actuator 310. Actuator 310 extends through a hole in wall 322. Forward end 324 of actuator 310 is connected to flat blade 326. As actuator 310 is translated forward in the direction of arrow 312, actuator 310 compresses spring 316 against wall 322 and forward end 324 pushes blade 326 out of front end 304 of housing 302.

FIG. 52c shows flat blade 326 extending out of slit opening 314 after actuator 310 has been pushed forward. Blade seal 328 is contained within housing 302 and is located adjacent slit opening 314 at front end 304. Flat blade 326 passes through blade seal 328 which includes a pair of flexible wipers 330 that face each other. Wipers 330 extend across the entire blade width 332 (FIG. 52b) and press against opposite sides of flat blade 326, thereby preventing blood from flowing into the rear segment of housing 302. Blade seal 328 can be made of silicone rubber or other resilient polymer. In other embodiments, blade seal 328 is a strip of polymer foam with a slit equivalent in size to blade width 332.

In use, front end 304 of housing 302 is inserted into attachment ring 22 or the combination of valvular structure 12 and attachment ring 22. Outer diameter 331 of housing 302 and ring seal 34 of attachment ring 22 can be sized such that a substantially fluid-tight seal is formed between the exterior surface of housing 302 and ring seal 304 when front end 304 is inserted into through attachment ring 22. When flat blade 326 punctures a beating heart and is retracted, blood from the heart may flow into attachment ring 22 and into slit opening 314 of housing 302. Blade seal 328 minimizes blood loss by preventing or inhibiting blood from flowing through and out of slitting tool 300.

In some embodiments, outer diameter 331 of housing 302 and housing seal 47 (FIG. 10a) of valvular structure 12 can be sized such that a substantially fluid-tight seal is formed between the exterior surface of housing 302 and housing seal 47 when front end 304 is inserted into valvular structure 12 which has been attached to attachment ring 22. When flat blade 326 punctures a beating heart and is retracted, blood from the heart may flow into attachment ring 22, valvular structure 12, and slit opening 314 of housing 302. Blade seal 328 minimizes blood loss by preventing or inhibiting blood from flowing through and out of slitting tool 300.

Referring again to FIG. 52a, stop feature 340 is located on housing 320 at a predetermined distance 342 from the forward most tip 344 of slitting tool 300. Stop feature 340 prevents tip 344 from pushing into the heart when slitting tool 340 is being positioned within attachment ring. Stop feature 340 includes a pair of protrusions 346 sized and shaped to fit within alignment features on attachment ring 22 and/or valvular structure 12.

In some embodiments, predetermined distance 342 is equivalent to or a few millimeters less than the longitudinal height of attachment ring 22. The longitudinal height can be the maximum dimension as measured along the longitudinal axis of attachment ring 22. The longitudinal height of an exemplary attachment ring is indicated by arrow 348 in FIG. 46d. In use, slitting tool 300 can be inserted by a surgeon or other user into attachment ring 22 secured to the heart, with no valvular structure 12 attached to attachment ring 22. When stop feature 304 abuts interface lip 25 of attachment ring 22, the user will know that tip 344 of slitting tool 300 is located at the proper position just above the heart. The user can twist slitting tool 300 about its central axis 301 until protrusions 346 become seated within indentations 230 (FIG. 4a) formed into interface lip 25. When protrusions 346 engage indentations 230, the user will know from tactile feed back that slitting tool 300 is in proper rotational alignment. Thereafter, the user can extend flat blade 326 to make a slit through the heart, and then use coring knife 140 under the same rotational alignment as slitting tool 300 to form a circular hole around the slit.

In some embodiments, predetermined distance 342 is equivalent to or a few millimeters less than the longitudinal stack height of valvular structure 12 and attachment ring 22. The longitudinal stack height of an exemplary assembly of valvular structure 12 and attachment ring 22 is indicated by arrow 350 in FIG. 2b. In use, slitting tool 300 can be inserted by a surgeon or other user into valvular structure 12 and attachment ring 22 which has been attached to the heart. When stop feature 304 abuts the proximal end of valvular structure 12, the user will know that tip 344 of slitting tool 300 is located at the proper position just above the heart. The user can twist slitting tool 300 about its central axis 301 until protrusions 346 become seated within alignment features (for example, coupling grooves 71 (FIG. 11a) formed into the proximal end of valvular structure 12. When protrusions 346 engage the alignment features, the user will know from tactile feed back that slitting tool 300 is in proper rotational alignment. Thereafter, the user can extend flat blade 326 to make a slit through the heart, and then use coring knife 140 under the same rotational alignment as slitting tool 300 to form a circular hole around the slit.

Stop feature 340 can be an annular flange, as illustrated, which can be an integral part of or permanently affixed to housing 320. Protrusions 346 can be spaced 180 degrees apart from each other on the circumference of stop feature 340. Alternatively, stop feature 304 can be movable along housing 302 to allow predetermined distance 342 to be adjusted if desired.

Figure 53B:
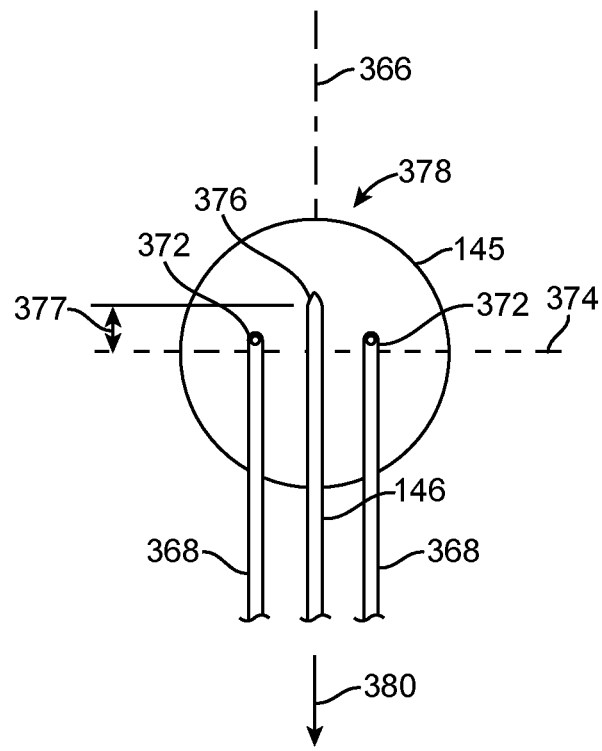

In FIGS. 53a-53f, another embodiment of coring knife 140 is shown having pistol-type grip 360, release trigger 362, and abutment control lever 364. FIG. 53a shows coring knife 140 in its starting configuration, in which the plane of coring abutment 145 is in line with longitudinal axis 366 of coring knife 140, and coring blade 137 is completely contained within coring knife case 141. The plane of the coring abutment 145 is defined by a plurality of points on the outer perimeter of coring abutment 145. Coring abutment 145 is held in position by two support rods 368. Control arm 146 is disposed between support rods 368. Support rods 368 and control arm 146 extend into the forward end of slide assembly 370 and into central shaft 372 (FIG. 53d) which is fixedly attached to grip 360. The forward ends of support rods 368 and control arm 146 are pivotally connected to different points on coring abutment 145. Control arm 146 is operatively coupled to abutment control lever 364.

Figure 53C:
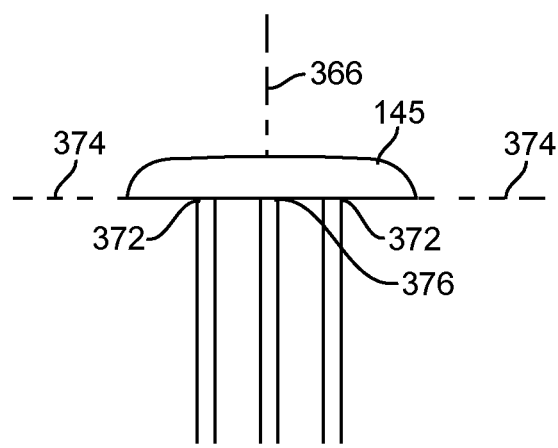

As shown in FIG. 53b, the forward ends of support rods 368 are attached to coring abutment 145 at points 372 that form pivot line 374 that is substantially perpendicular to longitudinal axis 366. The forward ends of support rods 368 can be attached to coring abutment 145 by a slender pin that extends within coring abutment 145. Control arm 146 is attached to coring abutment 145 at point 376 which is longitudinally offset by offset distance 377 from points 372 so as to be closer to forward most tip 378 of coring abutment 145. The forward end of control arm 146 can be attached to coring abutment 145 by another slender pin that extends within coring abutment 145. Due to offset distance 377, movement of control arm 146 rearward in the direction of arrow 380, while support rods 368 remain stationary, causes coring abutment 145 to rotate about pivot line 374. As shown in FIG. 53c, when point 376 has moved rearward by a distance equivalent to offset distance 377, the plane of coring abutment 145 is substantially perpendicular to longitudinal axis 366. Control arm 146 is operatively coupled to control lever 364 which is pivotally attached to grip 360. As shown in FIG. 53d, pivoting control lever 364 upward in a direction along arrow 382 causes control arm 146 to move rearward along arrow 380 until the plane of abutment surface 145 is substantially perpendicular to longitudinal axis 366. Control lever 364 includes safety latch 384. When control lever 364 is in a lowered position (FIG. 53a), safety latch 384 is in front of knob 385 of slide assembly 370 where it prevents slide assembly 370 from inadvertently sliding toward coring abutment 145. When control lever 364 is in a raised position (FIG. 53d), safety latch 384 has moved away from knob 385 and slide assembly 370 can slide toward coring abutment 145 when release trigger 362 is pressed by the user.

Slide assembly 370 comprises coring blade 137, coring knife case 141, and internal sleeve 386. Internal sleeve 386 (FIG. 53f) is disposed around and slides longitudinally over central shaft 372. Coring knife case 141 is fixedly attached to internal sleeve 386. Internal sleeve 386 includes a pair of linear slots 388 (FIG. 530 which extend substantially parallel to longitudinal axis 366. Pin 390 (FIG. 53e) protrudes from central shaft 372 into linear slots 388 and thereby prevents internal sleeve 386 from rotating relative to central shaft 372 and grip 360. Pin 390 prevents internal sleeve 386 from rotating relative to central shaft 372. Internal sleeve 386 also includes a series of holes 392 arranged along one or more lines substantially parallel to longitudinal axis 366. A ball detent mechanism within central shaft 372 engages one or more of the holes 392 to prevent slide assembly 370 from sliding freely on central shaft 372. Ball detent mechanism is operatively coupled to release trigger 362. Release trigger 362 is spring loaded in such a way that ball detent mechanism prevents slide assembly 370 from sliding when no force is applied to release trigger 362.

When a force is applied by a user to depress release trigger 362, ball detent mechanism disengages holes 392. The user may then grasp slide assembly 370 and slide it forward toward coring abutment 145, as shown in FIG. 53e. In use, slide assembly 370 is preferably moved forward to a point where forward edge 396 of coring knife case 141 touches or is just above the heart tissue 398. It is understood that coring knife case 141 is now located within the ring channel 14 of attachment ring 22 or valvular structure 12 combined with attachment ring 22. It is also understood that the coring abutment 145 is located within the heart cavity and abuts the heart tissue from the side opposite coring knife case 141. When forward edge 396 of coring knife case 141 is at the desired position, the user may let go of release trigger 362 so that ball detent mechanism engages holes 392 and locks in the longitudinal position of coring knife case 141.

At this stage, coring blade 137 remains completely retracted within coring knife case 141. Coring blade 137 is a hollow cylinder the forward end of which forms sharp circular tip 400. The rear end of coring blade 137 is fixedly attached to the front end of rotatable control sleeve 402. Helical coring guide or slot 147 is formed into the rear segment of rotatable control sleeve 402. Knob 385 is fixedly attached to the rear end of control sleeve 402. Manual rotation of knob 385 by the user causes control sleeve 402 and coring blade 137 to rotate relative to coring knife case 141 and internal sleeve 386 which are held stationary by ball detent mechanism and pin 390. Guide peg 148 protrudes from coring knife case 141 into helical slot 147 of control sleeve 402. Thus, rotation of knob 385 simultaneously causes control sleeve 402 and coring blade 137 to translate longitudinally toward coring abutment 145. Rotation in the reverse direction causes control sleeve 402 and coring blade 137 to translate longitudinally away from coring abutment 145. It is understood that knob 385 allows the user to have complete control of the force applied by coring blade and complete control of coring blade advancement by each turn of knob 385. In this embodiment, there is no spring loading on coring blade 137 that might otherwise remove complete control of applied force from the user.

In FIG. 53f, knob 385 has been rotated until circular tip 400 of coring blade 137 has pressed against coring abutment 145. In use, coring blade 137 would have made a circular cut entirely through the myocardium. A round piece of polymer foam, absorbent material, or resilient material, can be disposed within the rear end of the coring blade 137 to seal access holes for support rods 368 and control arm 146, and thereby stop or soak up blood and prevent blood from rushing into the rear portions of coring knife 140. A cylindrical portion of the myocardium would be completely detached from the remainder of the heart and contained within coring blade 137. The user may then pull coring knife 140 rearward, in a direction substantially parallel to longitudinal axis 366, thereby extracting the cylindrical portion of the myocardium out from beneath attachment ring 22 or the combination of valvular structure 12 and attachment ring 22. If the procedure is performed while the heart is beating, either ring valve 230 (FIG. 48b) of attachment ring 22 or valve 16 (FIG. 2a) of valvular structure 12 autonomously close after coring knife 140 is pulled out and thereby prevents significant loss of blood.

Use of coring knife 140 can begin by inserting coring abutment 145 oriented as shown in FIG. 53a into the slit previously formed by slitting tool 300. To facilitate insertion into the slit, the plane of the coring abutment 145 should be aligned in the same direction as the slit. Establishing the proper alignment can be difficult because the visual line of sight to the slit could be obstructed by the coring knife itself, by ring valve 230 (FIG. 48b) of attachment ring 22, or by valve 16 (FIG. 2a) of valvular structure 12. An alignment feature on the proximal end of attachment ring 22 or valvular structure 12 can be used by the user to align coring abutment 145 to the slit in the heart. The alignment feature can be in the form of indentations 230 (FIG. 4a) formed into interface lip 25 at the proximal end of attachment ring 22 and/or indelible markings 232 (FIG. 46c) in a contrasting color applied on interface lip 25. The alignment feature can be in the form of coupling grooves 71 (FIG. 11a) or alignment groove 497 formed into the proximal end of valvular structure 12 or be in the form of indelible markings applied to the proximal end of valvular structure 12. A corresponding feature on coring knife case 141, such as a protrusion and/or indelible markings, can be visually aligned or physically engaged with the alignment feature on attachment ring 22 or valvular structure 12.

As previously discussed, while the user depresses release trigger 362, slide assembly 370 can be moved forward to a point where forward edge 396 of coring knife case 141 touches or is just above the heart tissue 398. Positioning forward edge 396 to the desired position relative to the surface of the heart may be difficult to perform visually if the line of sight to the heart surface is obstructed by coring knife 140, valvular structure 12, and/or attachment ring 22.

Figure 54:
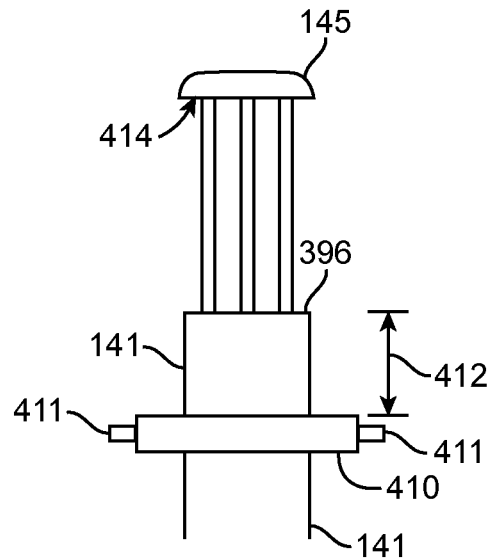
FIG. 54 is a partial plan view of a portion of a coring knife, showing a variation on the coring knife casing.

As shown in FIG. 54, stop feature 410 can be located on coring knife casing 141 at a predetermined distance 412 from forward edge 396 of coring knife case 141. Stop feature 410 prevents forward edge 396 from pushing into the heart when slide assembly 370 is being positioned within attachment ring 22. Stop feature 410 can include protrusions 411 sized and shape to fit within the alignment feature on attachment ring 22 or valvular structure 12, and/or can include indelible markings for aligning coring abutment 145 with the slit in the heart.

In some embodiments, predetermined distance 412 is equivalent to or a few millimeters less than the longitudinal height of attachment ring 22. The longitudinal height of an exemplary attachment ring is indicated by arrow 348 in FIG. 46d. In use, coring knife 140 can be inserted by a surgeon or other user into attachment ring 22 secured to the heart, with no valvular structure 12 attached to attachment ring 22. When stop feature 410 abuts interface lip 25 of attachment ring 22, the user will know that forward edge 396 of coring knife case 141 is located at the proper position. Thereafter, the user can let go of release trigger 362 to lock coring knife case 141 in place, then rotate knob 385 to extend coring blade 137 out of coring knife case 141 and into the heart.

In some embodiments, predetermined distance 412 is equivalent to or a few millimeters less than the longitudinal stack height of valvular structure 12 and attachment ring 22. The longitudinal stack height of an exemplary assembly of valvular structure 12 and attachment ring 22 is indicated by arrow 350 in FIG. 2b. In use, coring knife 140 can be inserted by a user into valvular structure 12 and attachment ring 22 which has been attached to the heart. When stop feature 410 abuts the proximal end of valvular structure 12, the user will know that forward edge 396 of coring knife case 141 is located at the proper position. Thereafter, the user can let go of release trigger 362 to lock coring knife case 141 in place, then rotate knob 385 to extend coring blade 137 out of coring knife case 141 and into the heart.

Stop feature 410 can be an annular flange which can be an integral part of or permanently affixed to coring knife casing 141. Alternatively, stop feature 410 can be movable along coring knife casing 141 to allow predetermined distance 412 to be adjusted if desired.

Referring again to FIG. 54, coring abutment 145 has abutment surface 414 that is substantially flat or planar. Abutment surface 414 faces coring knife case 141 after control lever 364 has been pivoted upward. In use, abutment surface 414 supports the interior surface of the heart as coring blade 137 rotates, extends out of coring knife case 141, and cuts from the exterior surface of the heart. Coring blade 137 ultimately presses against abutment surface 414 when cutting is complete.

Figure 55:
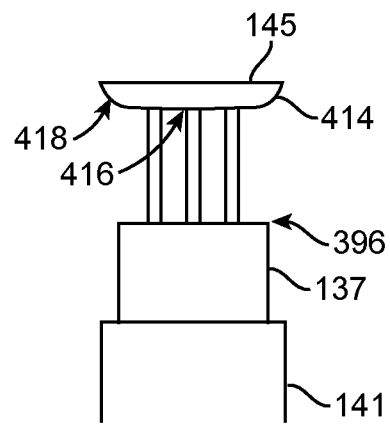
FIG. 55 is a partial plan view of a portion of a coring knife, showing a variation on the coring knife abutment.

In other embodiments, such as shown in FIG. 55, abutment surface 414 has a raised central portion 416 and tapered edges 418 at the outer circumference of coring abutment 145. As coring blade 137 rotates and moves closer to abutment surface 414, raised central portion 416 enters into coring blade 137 and tapered edges 418 abut forward edge 396 of coring blade. Raised central portion 416 and tapered edges 418 align the center of abutment surface 414 with the center of forward edge 396 of coring blade 137. Raised central portion 416 and tapered edges 418 prevent misalignment in which a portion of forward edge 396 extends beyond the outer circumference of coring abutment 145 and fails to press against abutment surface 414. Abutment surface 414 can be convex, spherical, conical or other shape having raised central portion and tapered edges.

In FIGS. 56a-56d, an embodiment of coring knife 140 is shown having an in-line grip configuration instead of a pistol-type grip. The coring knife of FIGS. 56a-56d has structural elements that are labeled with the same reference numerals as those of FIGS. 53a-53f and 54. Those structural elements have the same function as those described in connection with FIGS. 53a-53f and 54. The operational steps of FIGS. 56a-56d correspond to those of FIGS. 53a and 53d-53f.

Referring to FIGS. 56a-56d, the controls of coring knife 140 include numbers visible on the exterior surface of its controls to indicate to the user the sequence in which the controls are to be actuated. In surgical use, the first control to be actuated is control lever 364 in the form of a key. Turning or twisting of key 364 in the direction of arrow 365 causes coring abutment to pivot from its initial position in FIG. 56a to its next position in FIG. 56b. This is done while coring abutment 145 is inside the heart cavity and the remainder of coring knife 154 is outside, on the other side of the heart wall. The second control to be actuated is release trigger 362 in the form of a push button. Pressing down on push button 362, in the direction of arrow 363 (FIG. 56b), unlocks slide assembly 370 so that the user can take up any slack between heart tissue 398 and coring abutment 145 (inside the heart cavity) and/or coring knife case 141 (outside the heart cavity). Taking up the slack is performed by reducing the longitudinal distance between coring abutment 145 and coring knife case 141, as shown from FIGS. 56b-56c. The third control to be actuated is knob 385. Twisting of knob 385 in the direction of arrow 382 (FIG. 56c) causes coring blade 137 to extend out of coring knife case 141 toward coring abutment 145. The coring blade 137 cuts a circular hole through the portion of the heart wall 398 between coring knife case 141 and coring abutment 145.

Push button 362 is spring loaded and configured to be pressed down in direction 363 that is perpendicular or about perpendicular to longitudinal axis 366. Push button 362 is connected to a ball detent mechanism within central shaft 372. When push button 362 is in its natural state (not pressed down), the ball detent mechanism engages slide assembly 370 and prevents slide assembly 370 from inadvertently sliding toward coring abutment 145. In particular, the ball detent mechanism engages one or more of holes 392 to prevent slide assembly 370 from sliding freely on central shaft 372. When push button 362 is in its actuated state (pressed down with the application of downward force on push button), the ball detent mechanism disengages slide assembly 370, allowing slide assembly 370 to slide freely toward coring abutment 145. In particular, the ball detent mechanism disengages holes 392 to allow slide assembly 370 to slide freely on central shaft 372. When push button 362 is released (upon removal of the downward force), a spring acting on bush button 362 causes it to return to its natural state and thereby cause the ball detent mechanism to lock the slide assembly 370 at its present longitudinal position. More specifically, the ball detent mechanism locks internal sleeve 386 and coring knife case 141 at their present longitudinal position, and subsequent rotation of knob 385 causes coring blade 137 to extend out of coring knife case 141.

Key socket 420 is secured to the rear end of central shaft 372 by pins 422 (FIG. 56a) passing through central shaft 372 and key socket 420. Key 364 is disposed within key socket 420 and is connected to control arm 146 which extends into central shaft 372. The other end of control arm 146 is attached to coring abutment 142. Control arm 142 is able to slide longitudinally within central shaft 372. As explained below, twisting of key 364 causes longitudinal movement of control arm 146, which in turn causes coring abutment 145 to pivot between the positions shown in FIGS. 56a and 56b. The twist axis of key 364 is coaxial to longitudinal axis 366 of coring knife 140. In other embodiments, the twist axis of key 364 is offset from the longitudinal axis 366 and can be parallel or non-parallel to longitudinal axis 366.

Figure 57:
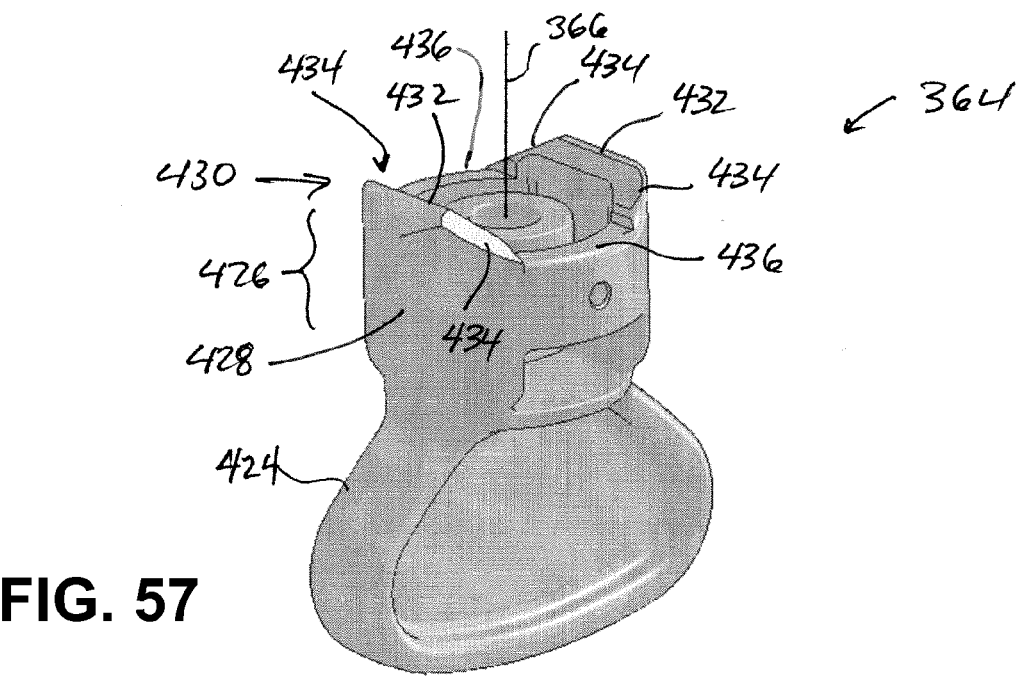
FIG. 57 is a perspective view of the key of FIGS. 56a-56d.

As shown in FIG. 57, key 364 includes paddle 424 attached to cylinder 426. When coring knife 140 is assembled, paddle 424 extends out of key socket 420 and is manipulated by the user to twist key 364. Cylinder 426 is contained within key socket 420. Outer surface 428 of cylinder 426 extends longitudinally and terminates at circular key edge 430. Key edge 430 appears as a circle when viewed along longitudinal axis 366 of coring knife 140. Key edge 430 defines the free end of cylinder 426. Key edge 430 has multiple segments that are uneven with each other. Key edge 430 includes two top segments 432, ramp segments 434, and two bottom segments 436. Top segments 432 are separated from each other by bottom segments 436. Ramp segments 434 connect top segments 432 to bottom segments 436. Top segments 432 form the outer-most tip of cylinder 426 and longitudinally extend further away from paddle 424 than bottom segments 436. In some embodiments, the difference in longitudinal position between top segments 432 and bottom segments 436 defines the longitudinal sliding distance of control arm 146 when key 364 is rotated.

Figure 58A:
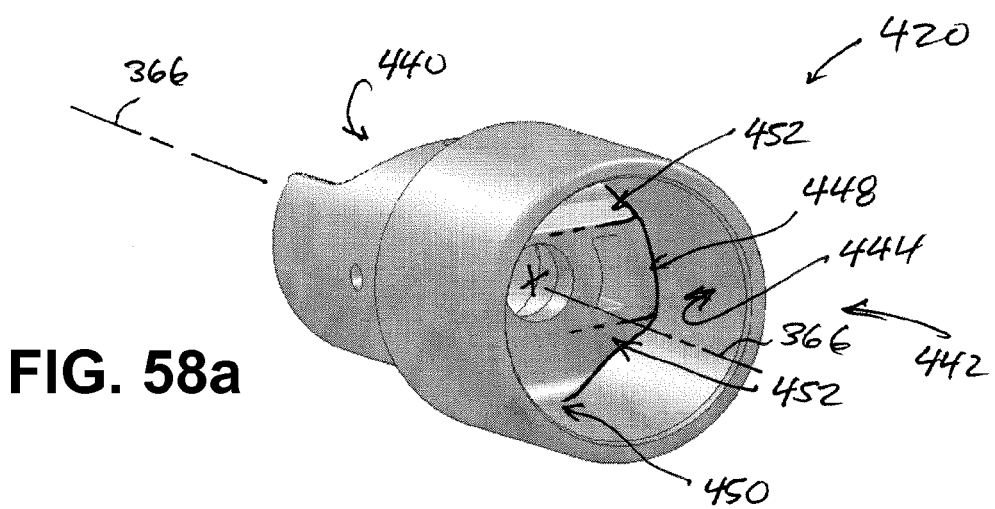
FIGS. 58a and 58b are a perspective and a perspective cut-away view of the key socket of FIGS. 56a-56d.
Figure 58B:
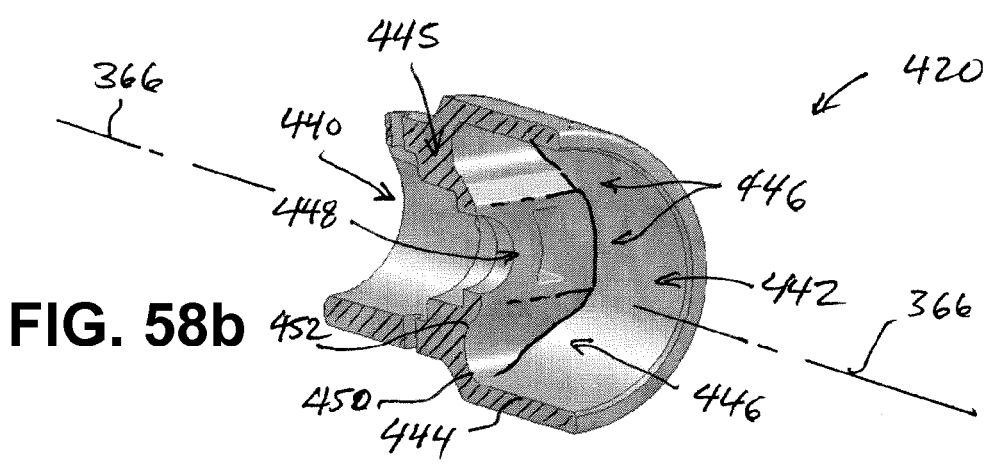

As shown in FIGS. 58a and 58b, key socket 420 includes forward cavity 440 and rear cavity 442 which are separated from each other by septum wall 445. When coring knife 140 is assembled, the rear end of central shaft 372 (FIG. 56d) is disposed within forward cavity 440, and cylinder 426 of key 364 is disposed within rear cavity 442. Central shaft 372 is attached to key socket 420 so that it cannot rotate or move longitudinally relative to key socket 420. Inner side surfaces 444 of rear cavity 442 terminate at bottom end surface 446 of rear cavity 442. Bottom end surface 446 forms one side of septum wall 445.

Bottom end surface 446 includes multiple areas that are uneven with each other. These uneven areas serve as bearing surfaces for key edge 430. When key 364 is twisted, contact between bottom end surface 446 of key socket 420 and key edge 430 of key 364 causes control arm 146 to slide longitudinally within central shaft 372 and thereby cause coring abutment 145 to pivot. The uneven areas of bottom end surface 446 are: top portion 448, two bottom portions 450, and ramp portions 452. Bottom portions 450 are located on opposite sides of top portion 448. Ramp portions 452 connect top portion 448 to bottom portions 450. Top portion 448 is located at the center of bottom end surface 446 and longitudinally extends further away from coring abutment 145 (FIG. 56d) than bottom portions 450. In some embodiments, the difference in longitudinal position between top portion 448 and bottom portions 450 defines the longitudinal sliding distance of control arm 146 when key 364 is rotated.

Figure 56A:
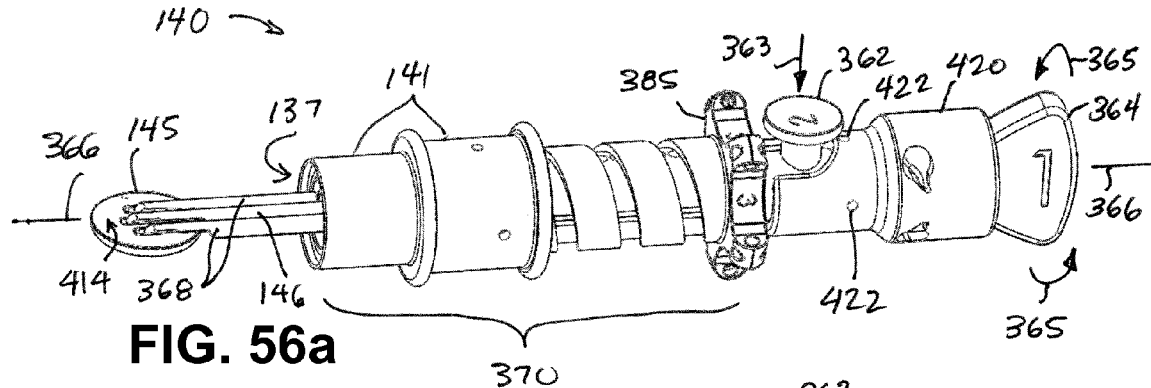
FIGS. 56a-56d are perspective views of a coring knife having an in-line grip configuration, showing a key within a key socket, the key for pivoting a coring abutment.
Figure 56B:
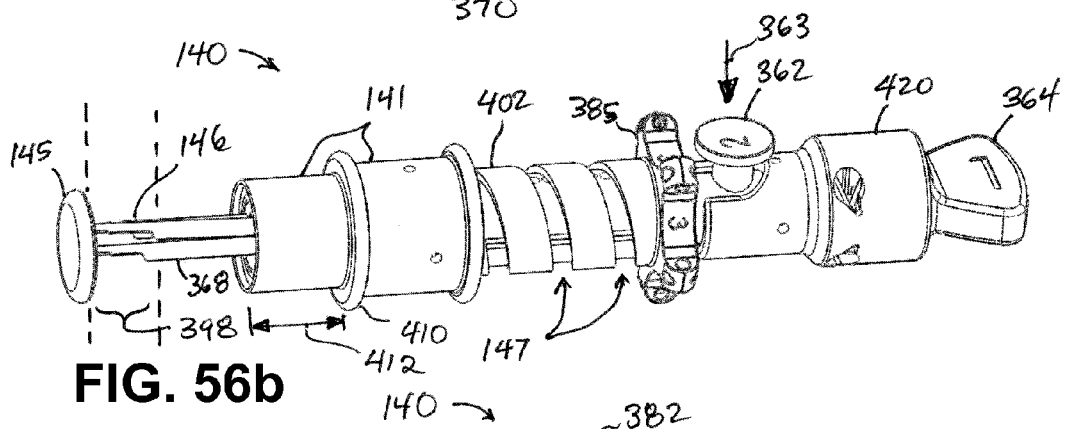
Figure 56C:
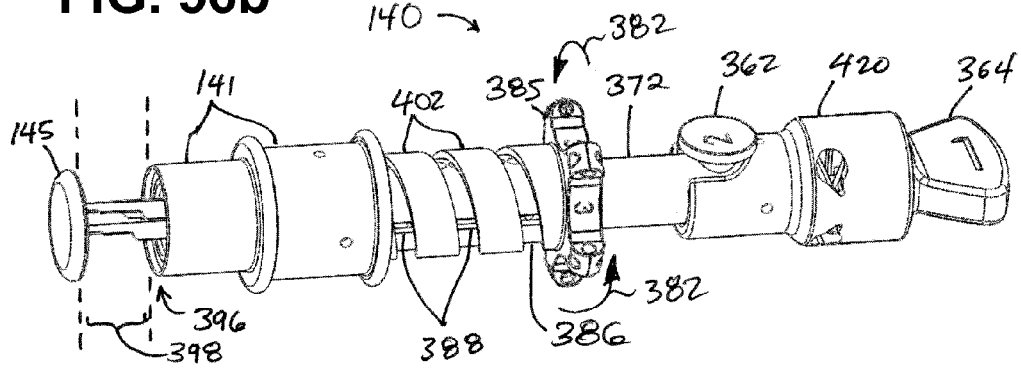
Figure 56D:
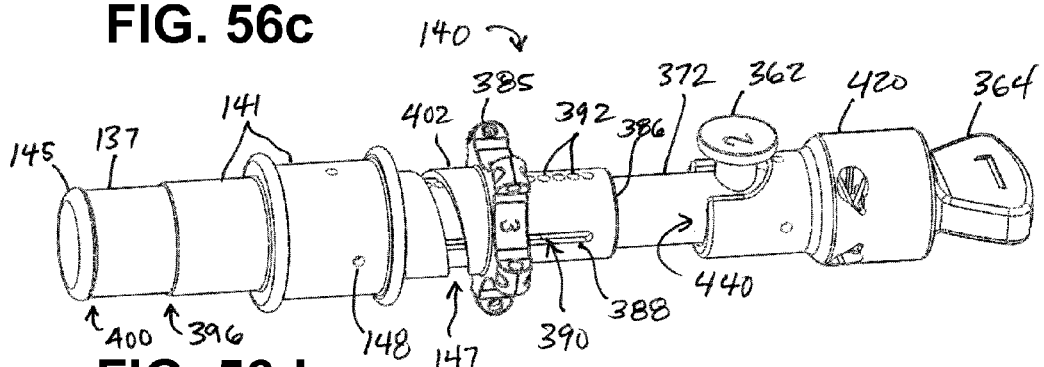
Figure 59A:
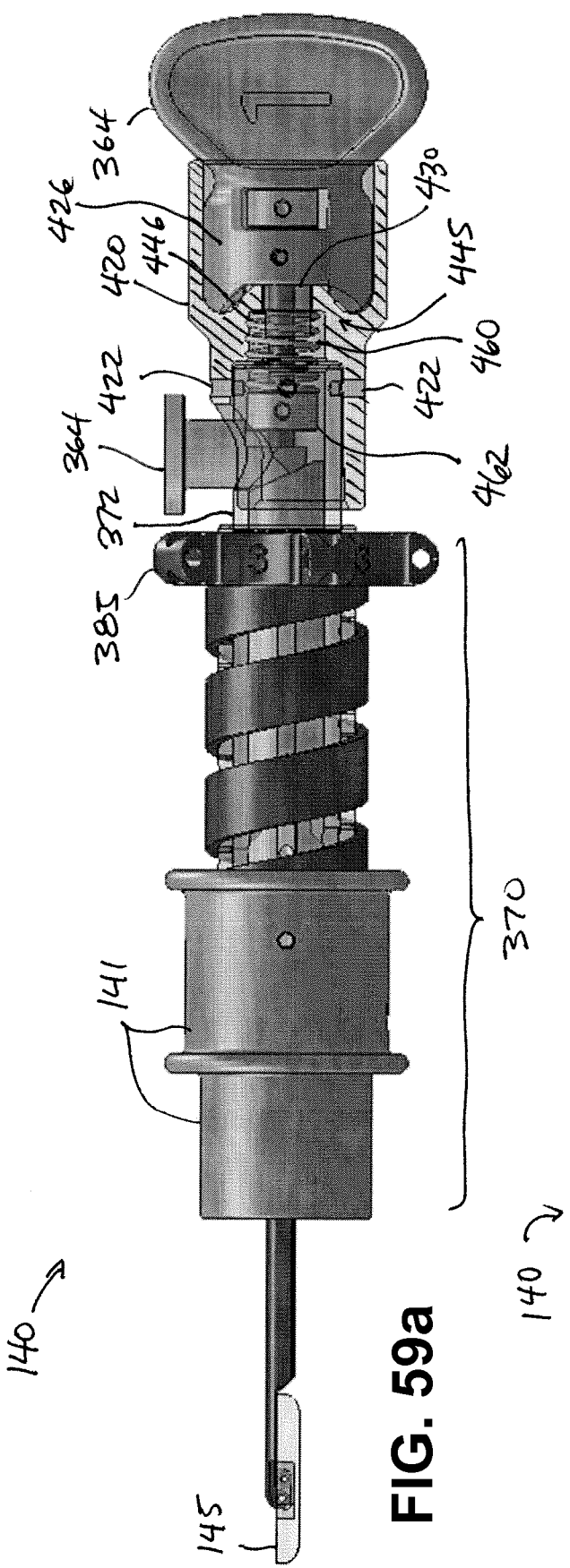
FIGS. 59a and 59b are elevation views of the coring knife of FIGS. 56a-56d, showing parts within the key socket.
Figure 59B:
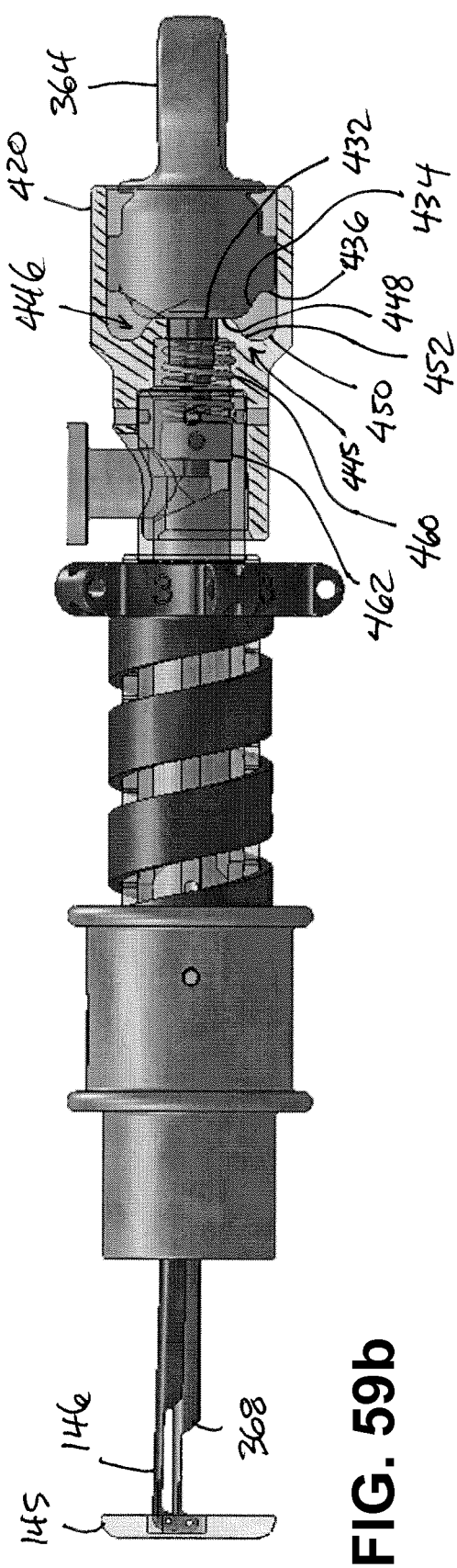

As shown in FIG. 59a, contours of bottom end surface 446 of key socket 420 mate with or correspond to contours of key edge 430 of key 364. When key 364 is in its initial position (as shown in FIGS. 59a and 56a), top segments 432 of key edge 430 face or make contact with bottom portions 450 of socket bottom end surface 446. Bottom segments 436 of key edge 430 face or make contact with top portion 448 of socket bottom end surface 446. When key 364 is twisted relative to key socket 420, ramp segments 434 of key edge 430 slide against ramp portions 452 of socket bottom end surface 446. As shown in FIG. 59b, further twisting of key 364 causes top segments 432 of key edge 430 to slide up and against ramp portions 452 until top segments 432 rest against top portion 448. As a result, key 364 moves rearward and away from coring abutment 145, pulls control arm 146 in the same direction, and pivots coring abutment 145. Control arm 146 and key 364 are longitudinally coupled in a way that key 364 and control arm 146 move longitudinally together. Control arm 146 and key 364 are not rotationally coupled so that control arm 146 does not twist when key 364 is twisted.

Contact between key 364 and the bottom end surface 446 of key socket 420 is maintained by compression spring 460 within forward cavity 440 of key socket 420. Compression spring 460 is compressed between bushing 462 on control arm 146 and septum wall 445 of key socket 420. Bushing 462 is an integral part of or fixedly attached to control arm 146. Thus, compression spring 460 causes control arm 146 to be biased in a forward longitudinal direction toward coring abutment 145. Since control arm 146 is connected to key 364, compression spring 460 also causes key 364 to be biased in a forward longitudinal direction against bottom end surface 446 of key socket 420.

In the illustrated embodiment, abutment surface 414 (FIG. 56a) is flat. In other embodiments, abutment surface 414 is not completely flat and includes a raised central portion and tapered edges, such as shown in FIG. 55.

Figure 60A:
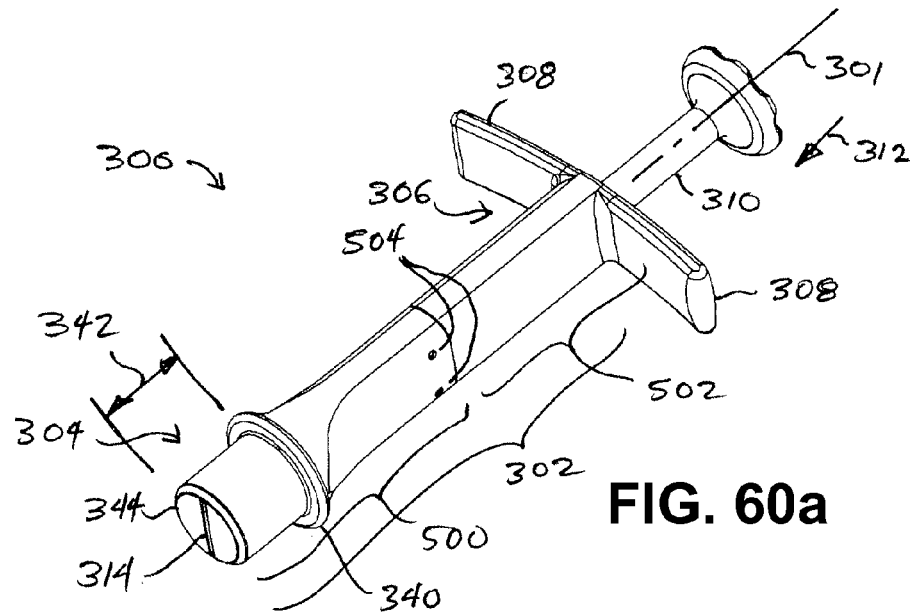
FIGS. 60a-60c are perspective and cross-sectional views of a slitting tool having a forward housing and a rear housing.
Figure 60B:
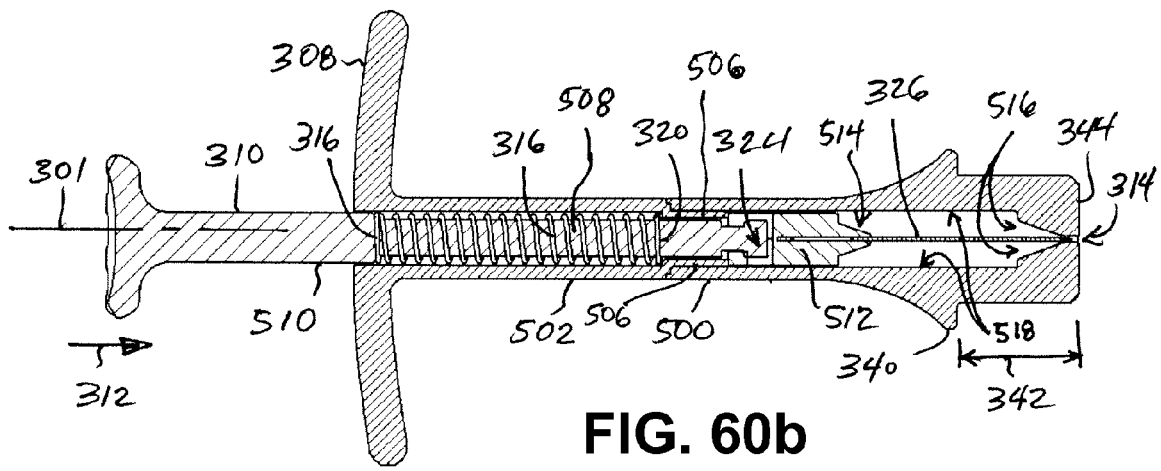
Figure 60C:
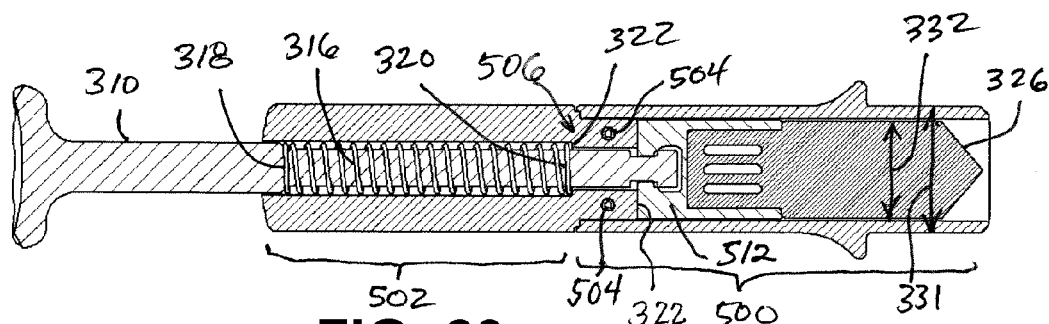

In FIGS. 60a-60c, another embodiment of slitting tool 300 is shown. The slitting tool of FIGS. 60a-60c has structural elements that are labeled with the same reference numerals as those of FIGS. 52a-52c. Those structural elements have the same function as those described in connection with FIGS. 52a-52c.

Referring to FIGS. 60a-60c, housing 302 includes forward housing 500 and rear housing 502 which are held together by pins 504. Front segment 506 of rear housing 502 is contained within forward housing 500. Pins 504 pass through front segment 506 and forward housing 500. Front segment 506 includes wall 322 having an aperture sized to receive forward end 324 of actuator 310. Spring 316 is coiled around middle segment 508 of actuator 310 and is compressed between rear segment 510 of actuator 310 and wall 322. Spring 316 keeps blade 326 housed completely within forward housing 500 until actuator 310 is pushed in the direction of arrow 312. Pushing actuator 310 causes the tip of blade 326 to protrude out of slit opening 314 and causes additional compression of spring 316. When actuator 310 is released by the user, spring 316 pushes rear segment 510 of actuator 310 so that blade 326 retracts into forward housing 500.

Forward end 324 of actuator 310 is coupled to blade holder 512 which is located on the opposite side of wall 322 as spring 316. Blade holder 512 secures blade 326 to forward end 324 of actuator 310. Blade 526 protrudes out of front end 514 of blade holder 512. Because blade holder 512 is wider than the aperture of wall 322, blade holder 512 abuts wall 322 and prevents forward end 324 of actuator 310 from being pulled by spring 316 into rear housing 502. When actuator 310 is pushed in the direction of arrow 312, blade holder 512 and blade 326 move forward until front end 514 abuts interior end surfaces 516 of forward housing 500. Interior end surfaces 516 are located within forward housing 500 and adjacent slit opening 314.

As shown in FIG. 60b, interior end surfaces 516 include two surfaces which are at a non-zero angle relative to each other so as to form a depression having a tapered cross sectional shape. Forward end 514 of blade holder 512 includes surfaces which are at a non-zero angle relative to each other so as to form a bump having a tapered cross sectional shape. In some embodiment, the depression formed by interior end surfaces 516 is configured to receive the bump on forward end 514 of blade holder 512 so as to form a fluid seal behind slit opening 314 that prevents blood within the heart from flowing into housing 302 when blade 326 is pushed forward completely.

In some embodiments, blade holder 512 makes contact with and slides against interior side surfaces 518 of forward housing 500 when actuator 312 is pushed. In some embodiments, contact between blade holder 512 and interior side surface 518 forms a fluid seal that prevents blood from flowing into rear housing 502 after blade 326 is retracted into forward housing 500.

In FIGS. 60a-60c, slitting tool 300 has no blade seal and no wiper at front end 304 of housing 302. In other embodiments, blade seal and wiper shown in FIG. 52c are incorporated into the slitting tool of FIGS. 60a-60c.

Any elements described herein as singular can be pluralized (i.e., anything described as "one" can be more than one). Attaching, coupling, and joining can be used interchangeably within this description. Any species element of a genus element can have the characteristics or elements of any other species element of that genus. The above-described configurations, elements or complete assemblies and methods and their elements for carrying out the invention, and variations of aspects of the invention can be combined and modified with each other in any combination.

What is claimed is:

1. A coring knife comprising:
   a coring blade including a circular cutting edge;
   a coring abutment located forward of the cutting edge;
   a key socket located to the rear of the coring blade, the key socket including a bearing surface; and
   a key connected to the coring abutment and including a key edge in contact with the bearing surface, the key configured to be moved relative the key socket,
   wherein when the key is moved relative the key socket, the key edge slips against the bearing surface and the key pivots the coring abutment relative to the coring blade,
   wherein when the coring abutment pivots, a portion of the coring abutment moves closer to the coring blade,
   wherein the key includes a cylinder having an outer surface that terminates at the key edge,
   wherein the key edge is disposed within a rear cavity of the key socket, and
   wherein the coring blade is mounted over a central shaft extending out of a forward cavity of the key socket, the coring blade is configured to be rotated around the central shaft, and wherein when the coring blade is rotated, the coring blade moves toward the coring abutment.

2. The coring knife of claim 1, further comprising a control arm connecting the coring abutment to the key, the control arm extending through the coring blade and the key socket.

3. The coring knife of claim 2, wherein the key is configured to be twisted about a twist axis, and wherein when the key is twisted, the key edge slips against the bearing surface and the key pivots the coring abutment relative to the coring blade.

4. The coring knife of claim 3, wherein when the key is twisted, the control arm moves along a longitudinal axis that is parallel to the twist axis.

5. The coring knife of claim 1, further comprising a coring knife case configured to be moved away from the key socket, wherein the coring blade is movable into and out of the coring knife case.

6. The coring knife of claim 5, wherein the coring blade is configured to move out of the coring knife case by rotating the coring blade relative to the coring knife case.

7. A coring knife comprising:
   a coring blade including a circular cutting edge;
   a coring abutment located forward of the cutting edge;
   a key socket located to the rear of the coring blade, the key socket including a bearing surface; and
   a key connected to the coring abutment and including a key edge in contact with the bearing surface, the key configured to be moved relative the key socket,
   wherein when the key is moved relative the key socket, the key edge slips against the bearing surface and the key pivots the coring abutment relative to the coring blade, wherein when the coring abutment pivots, a portion of the coring abutment moves closer to the coring blade,
   wherein the key includes a cylinder having an outer surface that terminates at the key edge,
   wherein the key edge is disposed within a rear cavity of the key socket, and
   wherein the coring blade is carried on an internal sleeve, the internal sleeve is carried on a central shaft extending out of a forward cavity of the key socket, the internal sleeve is configured to slide relative the central shaft in a direction toward the coring abutment, the coring blade is configured to be rotated relative the internal sleeve, and wherein when the coring blade is rotated, the coring blade moves toward the coring abutment.

8. The coring knife of claim 7, further comprising a control arm connecting the coring abutment to the key, the control arm extending through the coring blade and the key socket.

9. The coring knife of claim 8, wherein the key is configured to be twisted about a twist axis, and wherein when the key is twisted, the key edge slips against the bearing surface and the key pivots the coring abutment relative to the coring blade.

10. The coring knife of claim 9, wherein when the key is twisted, the control arm moves along a longitudinal axis that is parallel to the twist axis.

11. A coring knife comprising:
    a coring blade including a circular cutting edge;
    a coring abutment located forward of the cutting edge;
    a key socket located to the rear of the coring blade, the key socket including a bearing surface;
    a key connected to the coring abutment and including a key edge in contact with the bearing surface, the key configured to be moved relative the key socket, wherein when the key is moved relative the key socket, the key edge slips against the bearing surface and the key pivots the coring abutment relative to the coring blade, wherein when the coring abutment pivots, a portion of the coring abutment moves closer to the coring blade;
    a coring knife case configured to be moved away from the key socket, wherein the coring blade is movable into and out of the coring knife case; and
    a control sleeve attached to the coring blade, the control sleeve having a helical slot that extends into the coring knife case, wherein the coring knife case includes a guide peg that protrudes into the helical slot, and wherein rotation of the control sleeve causes the coring blade to move out of the coring knife case.

12. The coring knife of claim 11, wherein the key includes a cylinder having an outer surface that terminates at the key edge.

13. The coring knife of claim 12, wherein the key edge is disposed within a rear cavity of the key socket.

14. The coring knife of claim 13, wherein the key socket includes a forward cavity and a septum wall separating the forward cavity from the rear cavity, and the bearing surface forms a side of the of the septum wall within the rear cavity.

15. The coring knife of claim 13, wherein the coring blade is mounted over a central shaft extending out of a forward cavity of the key socket, the coring blade is configured to be rotated around the central shaft, and wherein when the coring blade is rotated, the coring blade moves toward the coring abutment.

16. The coring knife of claim 11, further comprising an internal sleeve and a central shaft, the central shaft fixedly attached to the key socket and extending into the internal sleeve, the internal sleeve carrying the control sleeve, the coring blade, and the coring knife case, and wherein the internal sleeve is configured to be selectively positioned and locked at any one of a plurality of locations on the central shaft.

17. A coring knife comprising:
a coring blade including a cylindrical wall defining a circular cutting edge and a hollow interior;
a coring abutment;
a coring knife case containing the coring blade, the coring blade configured to be extended out of the coring knife case and toward the coring abutment; and
a key coupled to the coring abutment by a control arm extending into the coring blade, the key disposed within a key socket and configured to be rotated relative to the key socket, wherein when the key is rotated relative the key socket, the key pulls the control arm in a manner that pivots the coring abutment relative to the coring blade.

18. The coring knife of claim 17, wherein the coring knife case includes a stop feature configured to fit in an alignment feature of a separate device for aligning the coring knife prior to extension of the coring blade out of the coring knife case.

19. The coring knife of claim 17, wherein the coring knife case is configured to be selectively positioned and locked at any one of a plurality of locations between the key socket and the coring abutment prior to extension of the coring blade out of the coring knife case.

20. The coring knife of claim 19, further comprising a detent mechanism that selectively locks and unlocks the coring knife case at any one of the plurality of locations between the key socket and the coring abutment.

21. The coring knife of claim 17, wherein when the coring abutment pivots, a portion of the coring abutment moves closer to the coring blade.

\* \* \* \* \*